United States Patent

Pages Santacana et al.

(10) Patent No.: US 6,683,096 B2
(45) Date of Patent: Jan. 27, 2004

(54) INDOLYLPIPERIDINE DERIVATIVES AS ANTIHISTAMINIC AND ANTIALLERGIC AGENTS

(75) Inventors: Lluis Pages Santacana, Barcelona (ES); Silvia Fonquerna Pou, Barcelona (ES); Carles Puig Duran, Barcelona (ES); Maria Dolors Fernandez Forner, Barcelona (ES)

(73) Assignee: Almirall Prodesfarma, S.A., Barcelona (ES)

( * ) Notice: Subject to any disclaimer, the term of this patent is extended or adjusted under 35 U.S.C. 154(b) by 0 days.

(21) Appl. No.: 10/006,416

(22) Filed: Dec. 4, 2001

(65) Prior Publication Data

US 2002/0147344 A1 Oct. 10, 2002

Related U.S. Application Data

(63) Continuation of application No. PCT/EP00/05010, filed on May 31, 2000.

(30) Foreign Application Priority Data

Jun. 4, 1999 (ES) ................................................ 9901232

(51) Int. Cl.$^7$ ..................... A61K 31/445; C07D 401/04
(52) U.S. Cl. ......................................... 514/323; 546/201
(58) Field of Search ............................ 514/323; 546/201

(56) References Cited

U.S. PATENT DOCUMENTS 5,650,416 A    7/1997   Carr et al. ................... 514/321

FOREIGN PATENT DOCUMENTS

| EP | 0 224 919 A2 | 6/1987 |
| EP | 0 324 431 A1 | 7/1989 |
| EP | 0 648 759 A1 | 4/1995 |
| EP | 0 722 942 A1 | 7/1996 |
| WO | WO 98/38189 A1 | 9/1998 |
| WO | WO 99/17773 A1 | 4/1999 |
| WO | WO 01/96328 | * 12/2001 |

OTHER PUBLICATIONS

Cross et al. "Imidazole derivatives . . . " CA 94:15731 (1980).*
Hamaguchi et al. "Preparation of acylpyrazole oximes . . . " CA 108:21882 (1987).*
Chang et al. (1979) "Heterogeneity of Histamine $H_1$–Receptors: Species Variations in [$^3$H]Mepyramine Binding of Brain Membranes" *Journal of Neurochemistry* 32:1653–1663.
Leysen et al. (1991) "Comparative Study of Central and Peripheral Histamine–$H_1$ Receptor Binding In Vitro and Ex Vivo of Non–Sedating Antihistamines and of Noberastine, a New Agent" *Drug Development Research* 22:165–178.
Perregaard et al. (1992). "Selective, Centrally Acting Serotonin 5–$HT_2$ Antagonists. 1.2–and 6–Substituted 1–Phenyl–3–(4–piperidinyl)–1 H–indoles," *J. Med. Chem.* 35:4813–4822.
Shigenaga et al. (1996). "(2E,4E)–N–(4–(1H–Indol–3–y1)piperidin–1–y1)alkyl–5–(substituted phenyl)–2,4–pentadienamides as Antiallergic Agents with Antihistaminic and Anti Slow–Reacting Substance (SRS) Activities," *Arch. Pharm.Pharm. Med. Chem.* 329(1), 3–10.

* cited by examiner

*Primary Examiner*—Ceila Chang
(74) *Attorney, Agent, or Firm*—Morrison & Foerster LLP

(57) ABSTRACT

Indolylpiperidine compounds of formula (I)

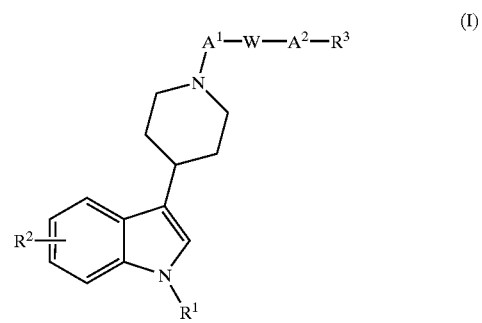

wherein:
$A^1$ represents an alkylene, alkyleneoxy, alkylenethio, alkanoyl or hydroxyalkylene group;
$A^2$ represents a single bond, an alkylene or alkenylene group;
W represents a single bond or a phenylene or furanylene group which is unsubstituted or substituted by one or more halogen atoms, alkoxy groups and/or alkyl groups;
$R^2$ represents a hydrogen or halogen atom or an alkyl or alkoxy group; and
$R^3$ represents a carboxyl group or a tetrazolyl group.

The present invention provides novel indolylpiperidine compounds having imporved antihistamine and antiallergic activity.

16 Claims, No Drawings

INDOLYLPIPERIDINE DERIVATIVES AS ANTIHISTAMINIC AND ANTIALLERGIC AGENTS

CROSS REFERENCE TO RELATED APPLICATIONS

This application is a continuation of International Application No. PCT/EP00/05010 filed May 31, 2000, and published in English on Dec. 14, 2000, which claims the benefit of Spanish Application No. 9901232 filed Jun. 4, 1999, the contents of each are incorporated herein by reference.

The present invention relates to novel indolylpiperidine compounds and pharmacologically acceptable salts thereof which have antihistaminic activity and antiallergic activity and are useful as medicaments for the treatment of bronchial asthma, allergic rhinitis, conjunctivitis, dermatosis, urticaria and the like.

The present invention also relates to a method for preparing the indolylpiperidine compounds, pharmaceutical compositions useful for the treatment of allergic diseases and bronchial asthma which comprises an effective amount of the indolylpiperidine compound.

Several antihistaminics and antiallergic agents are known which have indolylpiperidine structures. Examples of indolylpiperidine compounds represented by the following formula:

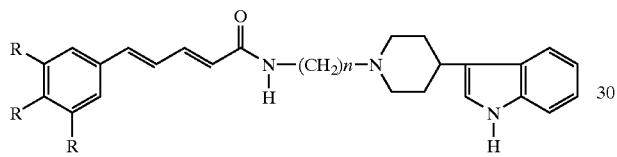

(where R=H, OH, OR' and n=2-6) are described in Shigenaga, S. et al., Arch. Pharm. Med. Chem.(1996) 329:3–10.

Furthermore, as compounds useful for the treatment of allergic diseases, EP 224919 discloses for example the compounds represented by the following formula:

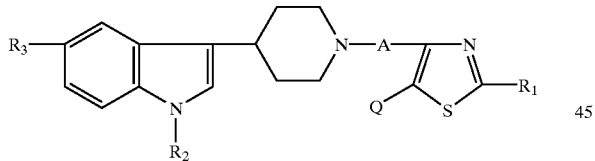

(where $R_1$=opt.subst.amino; $R_2$=H, lower alkyl or aryl; $R_3$=H, $NO_2$, opt.subst.amino, OH or lower alkoxy; A=lower alkylene; Q=H or halogen).

Most of these compounds are characterized as antiallergic agents useful for treating allergic asthma, rhinitis, conjunctivitis and urticaria.

Current antihistamines cannot be considered to be fully satisfactory from a safety point of view and problems remain with respect to adverse reactions such as sleepiness, sedation, hydrodipsia, mydriasis, palpitation and arrhythmia mediated through their undesirable penetration of the central nervous system, antiacetylcholinergic activity, activity against cardiovascular system or the like. Consequently, the clinical need exists for antihistamines and antiallergic agents which are largely devoid of sedative and cardiovascular side-effects.

The present invention provides novel indolylpiperidine compounds having improved antihistamine and antiallergic activity.

The present invention also provides novel indolylpiperidine compounds which due to their lack of lipophilic properties are almost totally unable to penetrate into the brain and hence lack sedative secondary effects. It can also be understood that the compounds of the present invention have reduced cardiovascular side effects.

A further objective of the present invention is to provide a method for preparing said compounds.

Yet another objective is to provide a pharmaceutical composition comprising an effective amount of said compounds.

In accordance with the present invention, novel indolylpiperidine compounds represented by the formula I are provided:

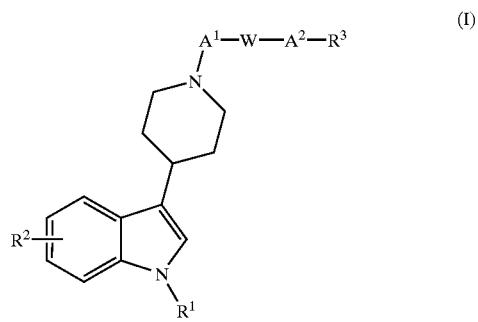

wherein:
$A^1$ represents an alkylene, alkyleneoxy, alkylenethio, alkanoyl or hydroxyalkylene group;

$A^2$ represents a single bond, an alkylene or alkenylene group;

W represents a single bond or a phenylene or furanylene group which is unsubstituted or substituted by one or more halogen atoms, alkoxy groups and/or alkyl groups;

$R^1$ represents a hydrogen atom or an alkyl, alkenyl, alkynyl, alkoxyalkyl, alkenyloxyalkyl, alkynyloxyalkyl alkoxy-alkoxyalkyl, phenylalkyl group wherein the phenyl ring is unsubstituted or substituted by one or more halogen atoms or alkyl, alkoxy or arylalkoxy (preferably phenylalkoxy) groups, or a cycloalkylalkyl group wherein the cycloalkyl group is unsubstituted or substituted by one or more halogen atoms, alkyl groups or alkoxy groups;

$R^2$ represents a hydrogen or halogen atom or an alkyl or alkoxy group; and $R^3$ represents a carboxyl group or a tetrazolyl group;
and pharmaceutically acceptable salts thereof.

In the above formula (I), the alkyl, alkylene, alkenyl, alkenylene, alkynyl, alkyleneoxy, alkylenethio, alkanoyl, hydroxyalkylene and alkoxy groups mentioned in relation to the groups $A^1$, $A^2$, $R^1$ and $R^2$ in the compounds of the invention, may be branched or straight and are preferably "lower" alkyl, alkenyl or alkynyl moieties, that is containing up to 7 and particularly up to 5 carbons atoms.

The cycloalkyl group mentioned in relation to $R^1$ may be mono or polycyclic, preferably mono or bicyclic and most preferably monocyclic. The cycloalkyl group preferably contains from 3 to 14, more preferably from 3 to 10 and most preferably from 3 to 7 carbon atoms.

In accordance with another embodiment of the present invention, the present invention provides a method for preparing the compound represented by formula I.

In accordance with yet another embodiment of the present invention, the present invention provides a pharmaceutical composition comprising an effective amount of the compound represented by formula I together with a pharmaceutically acceptable carrier or coating.

In accordance with a further embodiment, the present invention provides a method for treating an allergic disease or bronchial asthma comprising the step of administering an effective amount of the compound represented by formula I. Further features and advantages of the present invention will become apparent from the Description of the Preferred Embodiment which follows, when read in the light of the attached Examples and Reference Examples.

In preferred compounds of the invention $A^1$ represents an alkylene, alkyleneoxy, hydroxyalkylene or alkylenethio group.

In preferred compounds of the invention $A^2$ represents a single bond or a $C_{1-4}$ alkylene or $C_{2-5}$ alkenylene group.

In preferred compounds of the invention W represents a furanylene group or a phenylene group which is unsubstitued or substituted by one or two fluorine, chlorine or bromine atoms, methyl groups or methoxy groups. It will be understood that, in compounds of the invention wherein W is other than a single bond, the phenylene or furanylene group may be substituted by $A^1$ and $A^2$ or, in the case that $A^2$ is a single bond, $R^3$ at any combination of substitutable ring positions relative to each other, for example 1,2; 1,3; or 1,4. In compounds of the invention wherein the phenylene or furanylene ring is further substituted for example by halogen atoms, alkyl groups and/or alkoxy groups, then the further substituents may be attached at any of the remaining available positions on the ring.

In preferred compounds of the invention $R^1$ represents a $C_{1-7}$ alkyl, alkenyl or alkynyl group, a $C_{2-5}$ alkoxyalkyl group, a $C_{3-7}$ alkenoxy-alkyl group, a $C_{3-7}$ alkynoxy-alkyl group, a $C_{3-7}$ alkoxy-alkoxyalkyl group, a benzyl or phenylethyl group which is unsubstituted or substituted by one or more halogen atoms, $C_{1-4}$ alkyl, methoxy or benzyloxy groups or a cycloalkylalkyl group wherein the cycloalkyl group is cyclopropyl, cyclobutyl, cyclopentyl, cyclohexyl, cycloheptyl or decalinyl which is unsubstituted or substituted by one or more halogen atoms, $C_{1-4}$ alkyl or methoxy groups and the alkyl part of the cycloalkylalkyl group is methylene, ethylene, propylene or butylene.

In preferred compounds of the invention $R^2$ represents a hydrogen, fluorine, chlorine or bromine atom or a methyl or methoxy group. It will be understood that the substituent $R^2$ may be attached at the 4, 5, 6 or 7 position of the indolyl nucleus.

More preferred compounds of formula I are those in which $A^1$ represents a methylene, ethylene, propylene, butylene, pentylene, hexylene, ethyleneoxy, propyleneoxy, hydroxybutylene, ethylsulfanyl or butylsulfanyl group; $A^2$ represents a single bond or a methylene, ethylene, propylene, methylethylene, butylene or ethenylene group; W represents an unsubstituted furanylene, unsubstituted phenylene, fluorophenylene, dibromophenylene, methylphenylene or methoxyphenylene group; $R^1$ represents a hydrogen atom or a propyl, butyl, isobutyl pentyl, hexyl, heptyl, 2-methylpropyl, 3-methylbutyl, allyl, propenyl, propynyl, methoxyethyl, methoxypropyl, ethoxyethyl, propoxyethyl, iso-propoxyethyl, prop-2-ynyloxyethyl, prop-2-enyloxyethyl, methoxyethoxyethyl, 4-fluorobenzyl, 4-methoxybenzyl, 4-(tert-butyl)-benzyl, 4-benzyloxybenzyl, 4-methoxyphenylethyl, cyclopropylmethyl, cyclopropylethyl or cyclopropylpropyl group; $R^2$ represents a hydrogen, fluorine, chlorine or bromine atom or a methyl or methoxy group; and $R^3$ is a carboxyl or a tetrazolyl group.

The pharmacologically acceptable salts of the compounds of the present invention represented by formula I may be acid addition salts or alkali addition salts. Examples of the acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate, and p-toluenesulfonate.

Examples of the alkali addition salts include inorganic salts such as, for example sodium, potassium, calcium and ammonium salts and organic alkali salts such as, for example, ethylenediamine, ethanolamine, N,N-dialkylenethanolamine, triethanolamine and basic aminoacids salts.

The compounds of the present invention represented by the above-described formula (I) may include enantiomers depending on their asymmetry or diastereoisomers. The single isomers and mixtures of the isomers fall within the scope of the present invention.

Although the preferred indolylpiperidine compounds of the present invention include the following compounds, the present invention will not be limited to these examples, 1. 2-(2-{4-[1-(4-fluoro-benzyl)-1H-indol-3-yl]-piperidin-1-yl}-ethoxy)-benzoic acid
2. 2-{2-[4-(1-pentyl-1H-indol-3-yl)-piperidin-1-yl]-ethoxy}-benzoic acid
3. 4-{4-[1-(2-ethoxy-ethyl)-1H-indol-3-yl]-piperidin-1-yl}-butyric acid
4. 3-(3-{4-[1-(4-fluoro-benzyl)-1H-indol-3-yl]-piperidin-1-yl}-propoxy)-benzoic acid
5. 4-{3-[4-(1-pentyl-1H-indol-3-yl)-piperidin-1-yl]-propoxy)-benzoic acid
6. 2-[2-(4-{1-[2-(2-methoxy-ethoxy)-ethyl]-1H-indol-3-yl}-piperidin-1-yl)-ethoxy]-benzoic acid
7. 3-[2-(4-{1-[2-(2-methoxy-ethoxy)-ethyl]-1H-indol-3-yl}-piperidin-1-yl)-ethoxy]-benzoic acid
8. 3-(2-{4-[1-(4-fluoro-benzyl)-1H-indol-3-yl]-piperidin-1-yl}-ethoxy)-benzoic acid
9. 3-{2-[4-(1-pentyl-1H-indol-3-yl)-piperidin-1-yl]-ethoxy}-benzoic acid
10. 3-(2-{4-[1-(2-ethoxy-ethyl)-1H-indol-3-yl]-piperidin-1-yl-ethoxy)-benzoic acid
11. 4-[2-(4-{1-[2-(2-methoxy-ethoxy)-ethyl]-1H-indol-3-yl}-piperidin-1-yl)-ethoxy]-benzoic acid
12. 4-{2-[4-(1-pentyl-1H-indol-3-yl)-piperidin-1-yl]-ethoxy}-benzoic acid
13. 2-[3-(4-{1-[2-(2-methoxy-ethoxy)-ethyl]-1H-indol-3-yl}-piperidin-1-yl)-propoxy]-benzoic acid
14. 2-(3-{4-[1-(4-fluoro-benzyl)-1H-indol-3-yl]-piperidin-1-yl}-propoxy)-benzoic acid
15. 2-{3-[4-(1-pentyl-1H-indol-3-yl)-piperidin-1-yl]-propoxy}-benzoic acid
16. 2-(3-{4-[1-(2-ethoxy-ethyl)-1H-indol-3-yl]-piperidin-1-yl}-propoxy)-benzoic acid
17. 3-[3-(4-{1-[2-(2-methoxy-ethoxy)-ethyl]-1H-indol-3-yl}-piperidin-1-yl)-propoxy]-benzoic acid
18. 3-{3-[4-(1-pentyl-1H-indol-3-yl)-piperidin-1-yl]-propoxy}-benzoic acid
19. 3-(3-{4-[1-(2-ethoxy-ethyl)-1H-indol-3-yl]-piperidin-1-yl}-propoxy)-benzoic acid
20. 4-[3-(4-{1-[2-(2-methoxy-ethoxy)-ethyl]-1H-indol-3-yl}-piperidin-1-yl)-propoxy]-benzoic acid 21. 4-(3-{4-[1-(2-ethoxy-ethyl)-1H-indol-3-yl]-piperidin-1-yl}-propoxy)-benzoic acid
22. 3-(4-{1-[2-(2-methoxy-ethoxy)-ethyl]-1H-indol-3-yl}-piperidin-1-yl)-propionic acid
23. 3-[4-(1-pentyl-1H-indol-3-yl)-piperidin-1-yl]-propionic acid
24. 4-(4-{1-[2-(2-methoxy-ethoxy)-ethyl]-1H-indol-3-yl}-piperidin-1-yl)-butyric acid
25. 4-{4-[1-(4-fluoro-benzyl)-1H-indol-3-yl]-piperidin-1-yl}-butyric acid
26. 4-[4-(1-pentyl-1H-indol-3-yl)-piperidin-1-yl]-butyric acid
27. 3-{4-[2-(4-{1-[2-(2-methoxy-ethoxy)-ethyl]-1H-indol-3-yl}-piperidin-1-yl)-ethyl]-phenyl}-propionic acid
28. 3-{4-[1-(4-fluoro-benzyl)-1H-indol-3-yl]-piperidin-1-yl}-propionic acid
29. 3-[4-(2-{4-[1-(2-ethoxy-ethyl)-1H-indol-3-yl]-piperidin-1-yl}-ethyl)-phenyl]-propionic acid
30. 3-{4-[2-(4-{1-[2-(2-methoxy-ethoxy)-ethyl]-1H-indol-3-yl}-piperidin-1-yl)-ethyl]-phenyl}-acrylic acid
31. 3-(4-{2-[4-(1-pentyl-1H-indol-3-yl)-piperidin-1-yl]-ethyl}-phenyl)-acrylic acid
32. 3-[4-(2-{4-[1-(2-ethoxy-ethyl)-1H-indol-3-yl]-piperidin-1-yl}-ethyl)-phenyl]-acrylic acid
33. 2-{4-[1-hydroxy-4-(4-{1-[2-(2-methoxy-ethoxy)-ethyl]-1H-indol-3-yl}-piperidin-1-yl)-butyl]-phenyl}-2-methyl-propionic acid
34. 2-(4-{1-hydroxy-4-[4-(1-pentyl-1H-indol-3-yl)-piperidin-1-yl]-butyl}-phenyl)-2-methyl-propionic acid
35. 2-[4-(4-{4-[1-(2-ethoxy-ethyl)-1H-indol-3-yl]-piperidin-1-yl}-1-hydroxy-butyl)-phenyl]-2-methyl-propionic acid
36. [2-(4-{1-[2-(2-methoxy-ethoxy)-ethyl]-1H-indol-3-yl}-piperidin-1-yl)-ethoxy]-acetic acid
37. (2-{4-[1-(4-fluoro-benzyl)-1H-indol-3-yl]-piperidin-1-yl}-ethoxy)-acetic acid
38. {2-[4-(1-pentyl-1H-indol-3-yl)-piperidin-1-yl]-ethoxy}-acetic acid
39. (2-{4-[1-(2-ethoxy-ethyl)-1H-indol-3-yl]-piperidin-1-yl}-ethoxy)-acetic acid
40. 5-(4-{1-[2-(2-methoxy-ethoxy)-ethyl]-1H-indol-3-yl}-piperidin-1-yl-methyl)-furan-2-carboxylic acid
41. 5-[4-(1-pentyl-1H-indol-3-yl)-piperidin-1-yl-methyl]-furan-2-carboxylic acid
42. 5-{4-[1-(2-ethoxy-ethyl)-1H-indol-3-yl]-piperidin-1-yl-methyl}-furan-2-carboxylic acid
43. 5-{4-[1-(4-fluoro-benzyl)-1H-indol-3-yl]-piperidin-1-ylmethyl}-furan-2-carboxylic acid.
44. 2-[4-(4-{4-[1-(4-fluoro-benzyl)-1H-indol-3-yl]-piperidin-1-yl}-1-hydroxy-butyl)-phenyl]-2-methyl-propionic acid
45. 2-{2-[4-(1-heptyl-1H-indol-3-yl)-piperidin-1-yl]-ethoxy}-benzoic acid
46. 2-(2-{4-[1-(4-tert-butyl-benzyl)-1H-indol-3-yl]-piperidin-1-yl}-ethoxy)-benzoic acid
47. 2-(2-{4-[1-(4-methoxy-benzyl)-1H-indol-3-yl]-piperidin-1-yl}-ethoxy)-benzoic acid
48. 2-(2-{4-[1-(4-benzyloxy-benzyl)-1H-indol-3-yl]-piperidin-1-yl}-ethoxy)-benzoic acid
49. 2-{2-[4-(1-iso-butyl-1H-indol-3-yl)-piperidin-1-yl]-ethoxy}-benzoic acid
50. 2-[2-(4-{1-[2-(4-methoxy-phenyl)-ethyl]-1H-indol-3-yl}-piperidin-1-yl)-ethoxy]-benzoic acid
51. 2-(4-{2-[4-(1H-indol-3-yl)-piperidin-1-yl]-ethyl}-phenyl)-2-methyl-propionic acid
52. 2-(4-{4-[4-(1H-indol-3-yl)-piperidin-1-yl]-butyryl}-phenyl)-2-methyl-propionic acid
53. 2-[4-(1H-indol-3-yl)-piperidin-1-ylmethyl]-benzoic acid
54. 3-[4-(1H-indol-3-yl)-piperidin-1-ylmethyl]-benzoic acid
55. 4-[4-(1H-indol-3-yl)-piperidin-1-ylmethyl]-benzoic acid
56. (3-{2-[4-(1H-indol-3-yl)-piperidin-1-yl]-ethoxy}-phenyl)-acetic acid
57. (3-{3-[4-(1H-indol-3-yl)-piperidin-1-yl]-propoxy}-phenyl)-acetic acid
58. (4-{2-[4-(1H-indol-3-yl)-piperidin-1-yl]-ethoxy}-phenyl)-acetic acid
59. (4-{3-[4-(1H-indol-3-yl)-piperidin-1-yl]-propoxy}-phenyl)-acetic acid
60. 3-(1-{3-[3-(1H-tetrazol-5-yl)-phenoxy]-propyl}-piperidin-4-yl)-1H-indole
61. 2-methyl-2-[4-(2-{4-[1-(3-methyl-butyl)-1H-indol-3-yl]-piperidin-1-yl}-ethyl)-phenyl]-propionic acid
62. 2-[4-(2-{4-[1-(2-ethoxy-ethyl)-1H-indol-3-yl]-piperidin-1-yl}-ethyl)-phenyl]-2-methyl-propionic acid
63. 2-methyl-2-[4-(4-{4-[1-(3-methyl-butyl)-1H-indol-3-yl]-piperidin-1-yl}-butyryl)-phenyl]-propionic acid
64. 2-{4-[1-(3-methyl-butyl)-1H-indol-3-yl]-piperidin-1-ylmethyl}-benzoic acid
65. 2-{4-[1-(2-ethoxy-ethyl)-1H-indol-3-yl]-piperidin-1-ylmethyl}-benzoic acid
66. 3-{4-[1-(2-ethoxy-ethyl)-1H-indol-3-yl]-piperidin-1-ylmethyl}-benzoic acid
67. 4-{4-[1-(3-methyl-butyl)-1H-indol-3-yl]-piperidin-1-ylmethyl}-benzoic acid
68. [3-(2-{4-[1-(3-methyl-butyl)-1H-indol-3-yl]-piperidin-1-yl}-ethoxy)-phenyl]-acetic acid
69. [3-(2-{4-[1-(2-ethoxy-ethyl)-1H-indol-3-yl]-piperidin-1-yl}-ethoxy)-phenyl]-acetic acid
70. [3-(3-{4-[1-(3-methyl-butyl)-1H-indol-3-yl]-piperidin-1-yl}-propoxy)-phenyl]-acetic acid
71. [3-(3-{4-[1-(2-ethoxy-ethyl)-1H-indol-3-yl]-piperidin-1-yl}-propoxy)-phenyl]-acetic acid
72. [4-(2-{4-[1-(3-methyl-butyl)-1H-indol-3-yl]-piperidin-1-yl}-ethoxy)-phenyl]-acetic acid
73. [4-(2-{4-[1-(2-ethoxy-ethyl)-1H-indol-3-yl]-piperidin-1-yl}-ethoxy)-phenyl]-acetic acid
74. [4-(3-{4-[1-(3-methyl-butyl)-1H-indol-3-yl]-piperidin-1-yl}-propoxy)-phenyl]-acetic acid
75. [4-(3-{4-[1-(2-ethoxy-ethyl)-1H-indol-3-yl]-piperidin-1-yl}-propoxy)-phenyl]-acetic acid
76. 2-{2-[4-(1-prop-2-ynyl-1H-indol-3-yl)-piperidin-1-yl]-ethoxy}-benzoic acid
77. 2-methyl-2-[4-(4-{4-[1-(3-methyl-butyl)-1H-indol-3-yl]-piperidin-1-yl}-butyryl)-phenyl]-propionic acid
78. 1-(2-ethoxy-ethyl)-3-(1-{3-[2-(2H-tetrazol-5-yl)-phenoxy]-propyl}-piperidin-4-yl)-1H-indole
79. 1-(3-methyl-butyl)-3-(1-{3-[2-(2H-tetrazol-5-yl)-phenoxy]-propyl}-piperidin-4-yl)-1H-indole
80. 1-(3-methyl-butyl)-3-(1-{3-[4-(2H-tetrazol-5-yl)-phenoxy]-propyl}-piperidin-4-yl)-1H-indole 81. 2-(2-{4-[1-(2-ethoxy-ethyl)-5-methoxy-1H-indol-3-yl]-piperidin-1-yl}-ethoxy)-6-fluoro-benzoic acid
82. 2-(2-{4-[1-(2-ethoxy-ethyl)-5-fluoro-1H-indol-3-yl]-piperidin-1-yl}-ethoxy)-6-fluoro-benzoic acid
83. 2-(2-{4-[1-(2-ethoxy-ethyl)-6-fluoro-1H-indol-3-yl]-piperidin-1-yl}-ethoxy)-6-fluoro-benzoic acid
84. 2-(2-{4-[5-bromo-1-(2-ethoxy-ethyl)-1H-indol-3-yl]-piperidin-1-yl}-ethoxy)-6-fluoro-benzoic acid
85. 2-(2-{4-[7-bromo-1-(2-ethoxy-ethyl)-1H-indol-3-yl]-piperidin-1-yl}-ethoxy)-6-fluoro-benzoic acid
86. 2-(2-{4-[5-chloro-1-(2-ethoxy-ethyl)-1H-indol-3-yl]-piperidin-1-yl}-ethoxy)-6-fluoro-benzoic acid
87. 2-(2-{4-[1-(2-ethoxy-ethyl)-1H-indol-3-yl]-piperidin-1-yl}-ethoxy)-6-fluoro-benzoic acid
88. 3,5-dibromo-2-(2-{4-[1-(2-ethoxy-ethyl)-5-methoxy-1H-indol-3-yl]-piperidin-1-yl}-ethoxy)-benzoic acid
89. 3,5-dibromo-2-(2-{4-[1-(2-ethoxy-ethyl)-5-fluoro-1H-indol-3-yl]-piperidin-1-yl}-ethoxy)-benzoic acid
90. 3,5-dibromo-2-(2-{4-[1-(2-ethoxy-ethyl)-6-fluoro-1H-indol-3-yl]-piperidin-1-yl}-ethoxy)-benzoic acid
91. 3,5-dibromo-2-(2-{4-[5-bromo-1-(2-ethoxy-ethyl)-1H-indol-3-yl]-piperidin-1-yl}-ethoxy)-benzoic acid
92. 3,5-dibromo-2-(2-{4-[7-bromo-1-(2-ethoxy-ethyl)-1H-indol-3-yl]-piperidin-1-yl}-ethoxy)-benzoic acid
93. 3,5-dibromo-2-(2-{4-[1-(2-ethoxy-ethyl)-1H-indol-3-yl]-piperidin-1-yl}-ethoxy)-benzoic acid
94. 2-(2-{4-[1-(2-ethoxy-ethyl)-6-fluoro-1H-indol-3-yl]-piperidin-1-yl}-ethoxy)-5-methyl-benzoic acid
95. 2-(2-(4-[5-chloro-1-(2-ethoxy-ethyl)-1H-indol-3-yl]-piperidin-1-yl}-ethoxy)-5-methyl-benzoic acid
96. 2-(2-{4-[1-(2-ethoxy-ethyl)-5-methoxy-1H-indol-3-yl]-piperidin-1-yl}-ethoxy)-4-methoxy-benzoic acid
97. 2-(2-{4-[1-(2-ethoxy-ethyl)-6-fluoro-1H-indol-3-yl]-piperidin-1-yl}-ethoxy)-4-methoxy-benzoic acid
98. 2-(2-{4-[5-bromo-1-(2-ethoxy-ethyl)-1H-indol-3-yl]-piperidin-1-yl}-ethoxy)-4-methoxy-benzoic acid
99. 2-(2-{4-[7-bromo-1-(2-ethoxy-ethyl)-1H-indol-3-yl]-piperidin-1-yl}-ethoxy)-4-methoxy-benzoic acid
100. 2-(2-{4-[5-chloro-1-(2-ethoxy-ethyl)-1H-indol-3-yl]-piperidin-1-yl}-ethoxy)-4-methoxy-benzoic acid
101. 2-(2-{4-[1-(2-ethoxy-ethyl)-5-methoxy-1H-indol-3-yl]-piperidin-1-yl}-ethoxy)-benzoic acid
102. 2-(2-{4-[1-(2-ethoxy-ethyl)-5-fluoro-1H-indol-3-yl]-piperidin-1-yl}-ethoxy)-benzoic acid
103. 2-(2-{4-[1-(2-ethoxy-ethyl)-6-fluoro-1H-indol-3-yl]-piperidin-1-yl}-ethoxy)-benzoic acid
104. 2-(2-{4-[5-bromo-1-(2-ethoxy-ethyl)-1H-indol-3-yl]-piperidin-1-yl}-ethoxy)-benzoic acid
105. 2-(2-{4-[5-bromo-1-(2-ethoxy-ethyl)-1H-indol-3-yl]-piperidin-1-yl}-ethoxy)-5-methyl-benzoic acid
106. 2-(2-{4-[5-chloro-1-(2-ethoxy-ethyl)-1H-indol-3-yl]-piperidin-1-yl}-ethoxy)-benzoic acid
107. 2-{2-[4-(1-propyl-1H-indol-3-yl)-piperidin-1-yl]-ethoxy}-benzoic acid
108. 2-(2-{4-[1-(2-iso-propoxy-ethyl)-1H-indol-3-yl]-piperidin-1-yl}-ethoxy)-benzoic acid
109. 2-(2-{4-[1-(3-methoxy-propyl)-1H-indol-3-yl]-piperidin-1-yl}-ethoxy)-benzoic acid
110. 2-(2-{4-[1-(2-ethoxy-ethyl)-4-fluoro-1H-indol-3-yl]-piperidin-1-yl}-ethoxy)-benzoic acid
111. 2-(2-{4-[1-(2-ethoxy-ethyl)-4-fluoro-1H-indol-3-yl]-piperidin-1-yl}-ethoxy)-5-methyl-benzoic acid
112. 2-(2-{4-[1-(2-ethoxy-ethyl)-4-fluoro-1H-indol-3-yl]-piperidin-1-yl}-ethoxy)-4-methoxy-benzoic acid
113. 2-(2-{4-[4-fluoro-1-(2-methoxy-ethyl)-1H-indol-3-yl]-piperidin-1-yl}-ethoxy)-benzoic acid
114. 2-(2-{4-[4-fluoro-1-(2-methoxy-ethyl)-1H-indol-3-yl]-piperidin-1-yl}-ethoxy)-5-methyl-benzoic acid
115. 2-(2-{4-[4-fluoro-1-(2-methoxy-ethyl)-1H-indol-3-yl]-piperidin-1-yl}-ethoxy)-4-methoxy-benzoic acid
116. 5-{4-[1-(2-ethoxy-ethyl)-1H-indol-3-yl]-piperidin-1-yl}-pentanoic acid
117. 6-{4-[1-(2-ethoxy-ethyl)-1H-indol-3-yl]-piperidin-1-yl}-hexanoic acid
118. 7-{4-[1-(2-ethoxy-ethyl)-1H-indol-3-yl]-piperidin-1-yl}-heptanoic acid
119. 3-(3-{4-[1-(2-ethoxy-ethyl)-1H-indol-3-yl]-piperidin-1-yl}-propoxy)-propionic acid
120. 2-(2-{4-[1-(2-ethoxy-ethyl)-7-methyl-1H-indol-3-yl]-piperidin-1-yl}-ethoxy)-5-methyl-benzoic acid
121. 2-(2-{4-[6-bromo-1-(2-ethoxy-ethyl)-1H-indol-3-yl]-piperidin-1-yl}-ethoxy)-benzoic acid
122. 2-(2-{4-[6-bromo-1-(2-ethoxy-ethyl)-1H-indol-3-yl]-piperidin-1-yl}-ethoxy)-5-methyl-benzoic acid
123. (2-{4-[1-(2-ethoxy-ethyl)-1H-indol-3-yl]-piperidin-1-yl}-ethylsulfanyl)-acetic acid
124. (4-{4-[1-(2-ethoxy-ethyl)-1H-indol-3-yl]-piperidin-1-yl}-butylsulfanyl)-acetic acid
125. (3-{3-[4-(1-cyclopropylmethyl-1H-indol-3-yl)-piperidin-1-yl]-propoxy}-phenyl)-acetic acid
126. (4-{2-[4-(1-cyclopropylmethyl-1H-indol-3-yl)-piperidin-1-yl]-ethoxy}-phenyl)-acetic acid
127. (3-{2-[4-(1-cyclopropylmethyl-1H-indol-3-yl)-piperidin-1-yl]-ethoxy}-phenyl)-acetic acid
128. 3-[4-(1-pentyl-1H-indol-3-yl)-piperidin-1-ylmethyl]-benzoic acid
129. 5-[4-(6-fluoro-1-pentyl-1H-indol-3-yl)-piperidin-1-ylmethyl]-furan-2-carboxylic acid
130. 3-[4-(6-fluoro-1-pentyl-1H-indol-3-yl)-piperidin-1-ylmethyl]-benzoic acid
131. 2-(4-{4-[4-(1-cyclopropylmethyl-1H-indol-3-yl)-piperidin-1-yl]-butyryl}-phenyl)-2-methyl-propionic acid
132. 3-{3-[4-(1-cyclopropylmethyl-1H-indol-3-yl)-piperidin-1-yl]-propoxy}-benzoic acid
133. 2-{2-[4-(1-cyclohexylmethyl-1H-indol-3-yl)-piperidin-1-yl]ethoxy}-benzoic acid
134. 2-(2-{4-[1-(2-allyloxy-ethyl)-1H-indol-3-yl]-piperidin-1-yl}-ethoxy)-benzoic acid
135. 2-(2-{4-[1-(2-prop-2-ynyloxy-ethyl)-1H-indol-3-yl]-piperidin-1-yl}-ethoxy)-benzoic acid
136. 2-(2-{4-[1-(2-propoxy-ethyl)-1H-indol-3-yl]-piperidin-1-yl}-ethoxy)-benzoic acid
137. 4-(2-{4-[1-(2-ethoxy-ethyl)-1H-indol-3-yl]-piperidin-1-yl}-ethoxy)-benzoic acid
138. 2-(2-{4-[1-(2-ethoxy-ethyl)-1H-indol-3-yl]-piperidin-1-yl}-ethoxy)-benzoic acid
139. 2-(2-{4-[1-(3-methyl-butyl)-1H-indol-3-yl]-piperidin-1-yl}-ethoxy)-benzoic acid
140. 2-(2-{4-[1-(2-methoxy-ethyl)-1H-indol-3-yl]-piperidin-1-yl}-ethoxy)-benzoic acid
141. 2-{2-[4-(1-allyl-1H-indol-3-yl)-piperidin-1-yl]-ethoxy}-benzoic acid
142. 2-(2-{4-[1-(2-ethoxy-ethyl)-5-methoxy-1H-indol-3-yl]-piperidin-1-yl}-ethoxy)-5-methyl-benzoic acid 143. 2-(2-{4-[7-bromo-1-(2-ethoxy-ethyl)-1H-indol-3-yl]-piperidin-1-yl}-ethoxy)-5-methyl-benzoic acid
144. 2-(2-{4-[7- bromo-1-(2-ethoxy-ethyl)-1H-indol-3-yl]-piperidin-1-yl}-ethoxy)-benzoic acid
145. 2-(2-{4-[1-(2-ethoxy-ethyl)-5-fluoro-1H-indol-3-yl]-piperidin-1-yl}-ethoxy)-5-methyl-benzoic acid
146. 2-(2-{4-[1-(2-ethoxy-ethyl)-5-fluoro-1H-indol-3-yl]-piperidin-1-yl}-ethoxy)-4-methoxy-benzoic acid
147. 2-(2-{4-[1-(2-ethoxy-ethyl)-7-methyl-1H-indol-3-yl]-piperidin-1-yl}-ethoxy)-benzoic acid
148. 2-{2-[4-(1-butyl-1H-indol-3-yl)-piperidin-1-yl]-ethoxy}-benzoic acid
149. 2-{2-[4-(1-hexyl-1H-indol-3-yl)-piperidin-1-yl]-ethoxy}-benzoic acid
150. 2-{2-[4-(1-cyclopropylmethyl-6-fluoro-1H-indol-3-yl)-piperidin-1-yl]-ethoxy}-benzoic acid
151. 2-{2-[4-(1H-indol-3-yl)-piperidin-1-yl]-ethoxy}-benzoic acid
153. 3-{4-[1-(2-ethoxyethyl)-1H-indol-3-yl]-piperidin-1-yl}-propionic acid
154. 2-(2-{4-[1-(2-ethoxy-ethyl)-1H-indol-3-yl]-piperidin-1-yl}-ethoxy)-5-methyl-benzoic acid
155. 2-[4-(4-{4-[1-(2-ethoxy-ethyl)-1H-indol-3-yl]-piperidin-1-yl}-butyryl)-phenyl]-2-methyl-propionic acid
156. 1-(2-ethoxy-ethyl)-3-(1-{3-[4-(2H-tetrazol-5-yl)-phenoxy]-propyl}-piperidin-4-yl)-1H-indole
157. 2-{2-[4-(1-cyclopropylmethyl-1H-indol-3-yl)-piperidin-1-yl]-ethoxy}-benzoic acid
158. 3-[4-(1-cyclopropylmethyl-1H-indol-3-yl)-piperidin-1-ylmethyl]-benzoic acid
159. (4-{3-[4-(1-cyclopropylmethyl-1H-indol-3-yl)-piperidin-1-yl]-propoxy}-phenyl)-acetic acid The novel indolylpiperidine compounds of the present invention represented by formula I can be prepared according to Scheme 1 from the corresponding piperidine derivative of formula II:

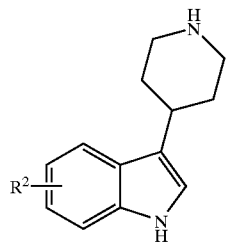

(II)

wherein $R^2$ is as defined above, with a reactive intermediate of general formula III:

$$X\text{---}A^1\text{---}W\text{---}A^2\text{---}R^4 \quad \text{(III)}$$

wherein $A^1$, $A^2$ and W are as defined above, $R^4$ is a nitrile group or a —$COOR^5$ group where $R^5$ is a C1-C4 alkyl group and X is a leaving group such as a chlorine or bromine atom, or a methane sulfonate, p-toluene sulfonate or benzene sulfonate group.

The reaction is preferably carried out in an inert organic solvent such as toluene, dioxane or methyl isobutyl ketone, at a temperature between 80° C. and 140° C. and in the presence of an inorganic base such as an alkali metal carbonate or bicarbonate. In the reaction, the corresponding alkylation product of general formula IV is formed:

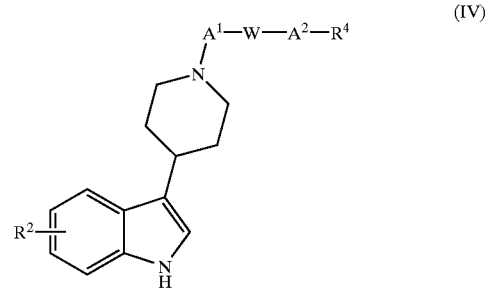

(IV)

Compound IV is alkylated on the indole nitrogen with a reactive intermediate of general formula V:

$$R^1\text{---}X \quad \text{(V)}$$

wherein X is a leaving group such as chlorine or bromine atom, or a methane sulfonate, p-toluene sulfonate or benzene sulfonate group and $R^1$ as defined above.

The reaction is preferably carried out in an inert organic solvent such as dimethylformamide, tetrahydrofuran or ethyl ether, at a temperature between 0° C. and 80° C. in the presence of an inorganic base such as sodium hydride or sodium amide. In the reaction, the corresponding alkylation product

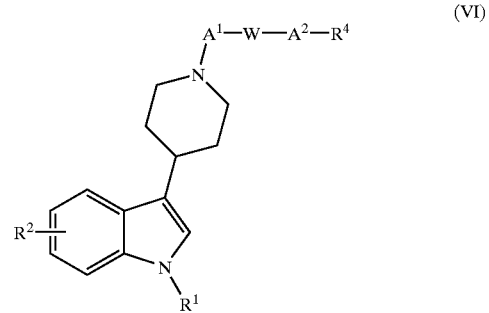

(VI)

of general formula VI is formed (see Scheme 1).

Alternatively, the alkylation sequence yielding intermediate VI can be reversed starting from the compound of general formula VII where $R^2$ is as defined above.

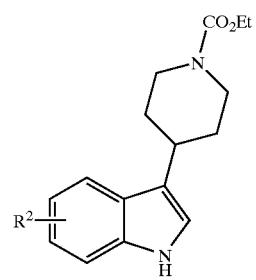

(VII)

Compound VII is alkylated on the indole nitrogen with a reactive intermediate of general formula V:

$$R^1\text{---}X \quad \text{(V)}$$

wherein X is a leaving group such as chlorine or bromine atom, or a methane sulfonate, p-toluene sulfonate or benzene sulfonate group and $R^1$ as defined above. This reaction leads to compound VIII (see Scheme 1), wherein $R^1$ and $R^2$ are defined

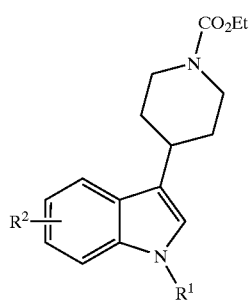

(VIII)

as above.

The reaction is preferably carried out in an inert organic solvent such as dimethylformamide, tetrahydrofurane or ethyl ether, at a temperature between 0° C. and 80° C. in the presence of an inorganic base such as sodium hydride or sodium amide.

Subsequent deprotection of compound VIII (see Scheme 1), first by boiling it in the presence of an excess of sodium or potassium hydroxide in a alcoholic solvent such as ethanol, isopropanol or n-butanol in a temperature between 80° C. and 180° C. and then neutralised with an inorganic acid such as hydrochloric or sulfuric acid, leads to the general structure IX (see Scheme 1), wherein $R^1$ and $R^2$ are defined as above.

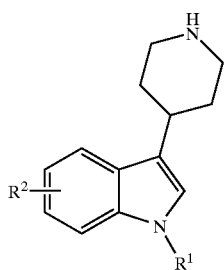

(IX)

Further alkylation of compound IX with a reactive intermediate of general formula (III)

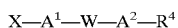

(III)

wherein $A^1$, $A^2$ and W are as defined above, $R^4$ is a nitrile group or a —$COOR^5$ group where $R^5$ is a C1-C4 alkyl group and X is a leaving group such as chlorine or bromine atom, or a methane sulfonate, p-toluene sulfonate or benzene sulfonate group. The reaction is preferably carried out in an inert organic solvent such as toluene, dioxane or methyl isobutyl ketone, at a temperature between 80° C. and 140° C. in the presence of an inorganic base such as an alkali metal carbonate or bicarbonate. In the reaction, the corresponding alkylation product of general formula VI is formed (see Scheme 1).

Compounds of general formula VI where $R^4$ represents an alkyl ester are treated with sodium or potassium hydroxide and further treatment with an inorganic acid such as hydrochloric or sulfuric acid provides the corresponding indole derivative of formula I where $R^3$ is a carboxylic acid. The reaction is preferably carried out in a solvent such as methanol, ethanol, tetrahydrofuran or an aqueous mixture of one of the above mentioned solvents at its boiling point.

When $R^4$ is a nitrile group, the reaction to yield the tetrazole is preferably carried out in presence of sodium azide in an organic solvent such as N,N-dimethyl formamide or N-methyl pyrrolidone, at a temperature between 60° C. and 180° C. for 10 to 20 hours, in presence of an inorganic acid such as hydrochloric acid. The corresponding compounds of general formula X are formed:

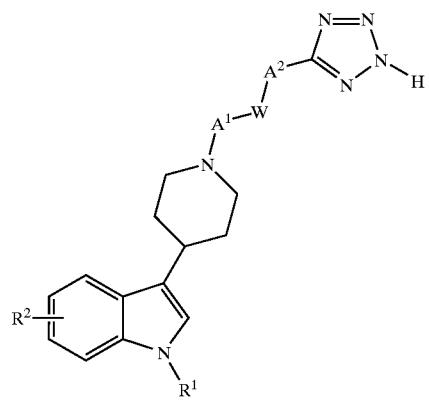

(X)

wherein $A^1$, $A^2$, $R^1$, $R^2$ and W are as defined above.

On the other hand, compounds of general formula IV are alkylated in the indol nitrogen with 2-(2-bromo-ethoxy)-tetrahydro-pyran to give compounds of general structure XI, wherein $A^1$, $A^2$, $R^2$ and $R^4$ are as defined above (see scheme 2). This reaction is preferably carried out in an inert solvent such as dimethylformamide, tetrahydrofuran or ethyl ether at a temperature between 0° C. and 80° C. in the presence of a inorganic base such as sodium hydride or sodium amide. Subsequent deprotection of compound XI boiling it in the presence of hydrogen chloride in a alcoholic solvent such as ethanol, methanol or isopropanol leads to a compound of general structure XII wherein $A^1$, $A^2$, $R^2$, $R^4$ and W are as defined above. Further alkylation of the compound XII with an intermediate of general formula $R^6$—X (XIII) where $R^6$ is a C1-C3 alkyl, alkenyl or alkynyl group and X is a leaving group such a chloride or a bromide atom or a methane sulfonate, p-toluenesulfonate or benzenesulfonate group, leads to a compound of general structure XIV, where $A^1$, $A^2$, $R^2$, $R^4$, $R^6$ and W are as defined above.

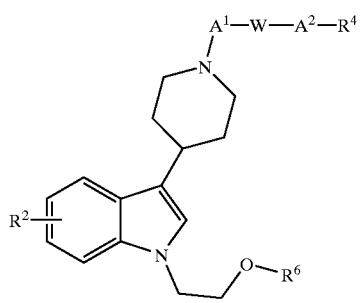

(XIV)

This reaction is preferably carried out in an inert solvent such as dimethylformamide, tetrahydrofuran or ethyl ether at a temperature between 0° C. and 80° C. in the presence of a inorganic base such as sodium hydride or sodium amide. Compounds of general formula XIV where $R^4$ represents an alkyl ester are treated with sodium or potassium hydroxide and further treatment with an inorganic acid provides the corresponding indole derivative of formule XV, wherein $A^1$, $A^2$, W, $R^2$, and $R^6$ are as defined above and $R^3$ is a carboxylic acid.

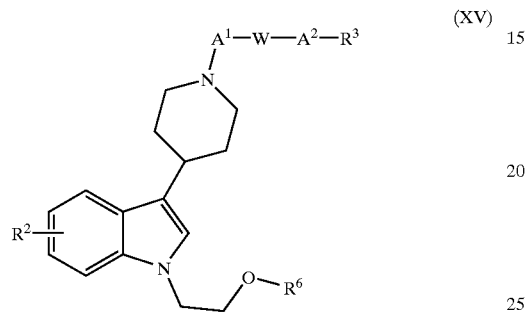

(XV)

This reaction is preferably carried out in a solvent such as methanol, ethanol, tetrahydrofuran or an aqueous mixture of the above mentioned solvents at its boiling point. The products are purified by chromatography or by crystallization. High yields, between 70% and 90%, are normally obtained.

If necessary, an excess of the reagent is employed to ensure complete reaction, and a polymer, such as a methyl isocyanate polystyrene or/and 3-(3-mercapto-phenyl)-propan-amido-methyl polystyrene may be conveniently added to react with the excess reagent. Isolation of products from reactions where a polymer bond reagent has been used is greatly simplified, requiring only filtration under reduced pressure.

The product from these reactions may be purified by solid phase extraction, using a suitable sorbent, such as Varian SCX, or Varian C18.

The piperidine derivatives of formula (II) can be prepared from the 4-piperidone as disclosed in the literature (J. Med. Chem. 1992, 35, 4813–4822). The reactive intermediates of general formula (III) can be prepared as disclosed in the literature.

Scheme 1

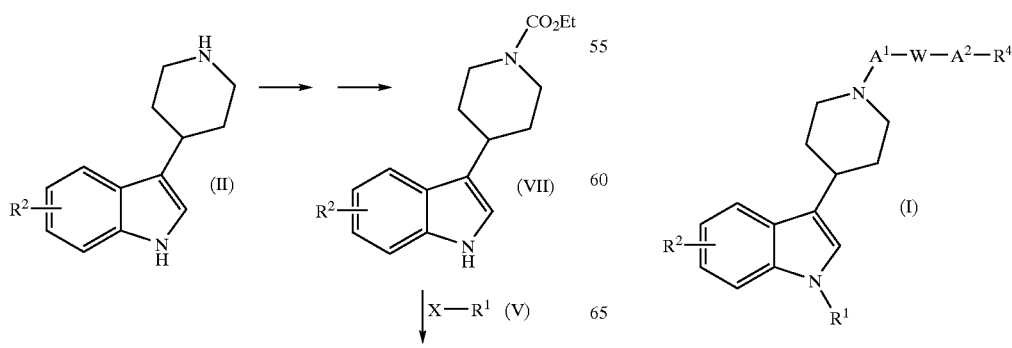

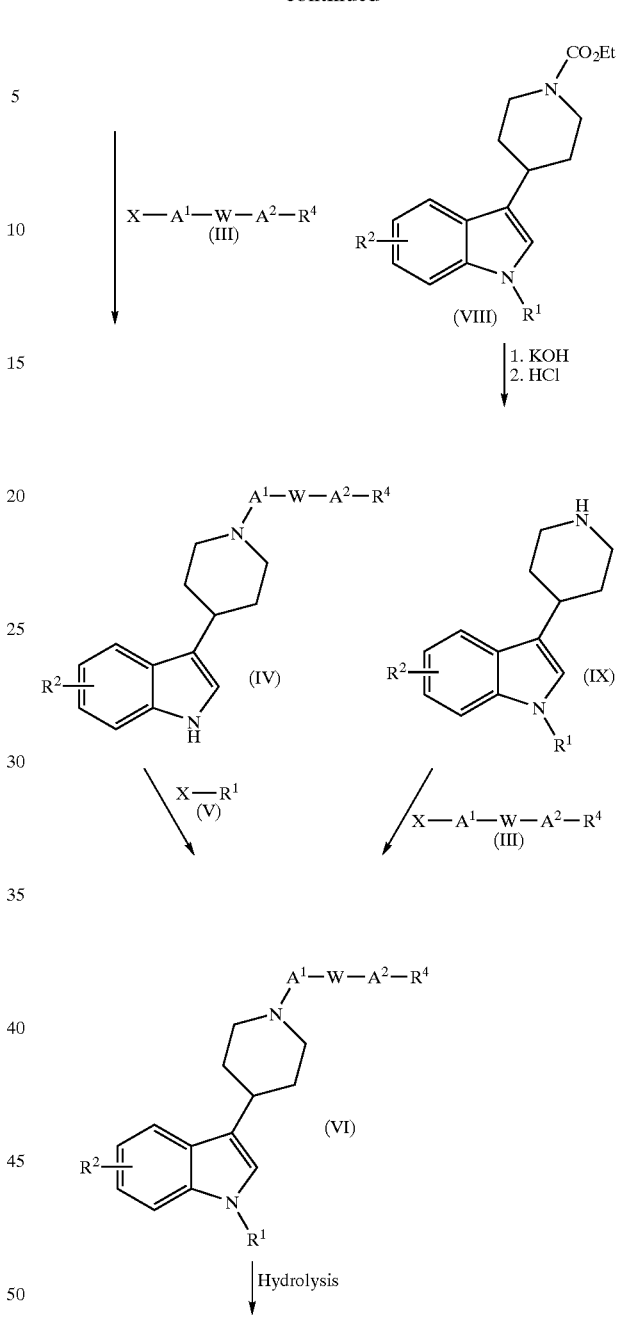

Scheme 2

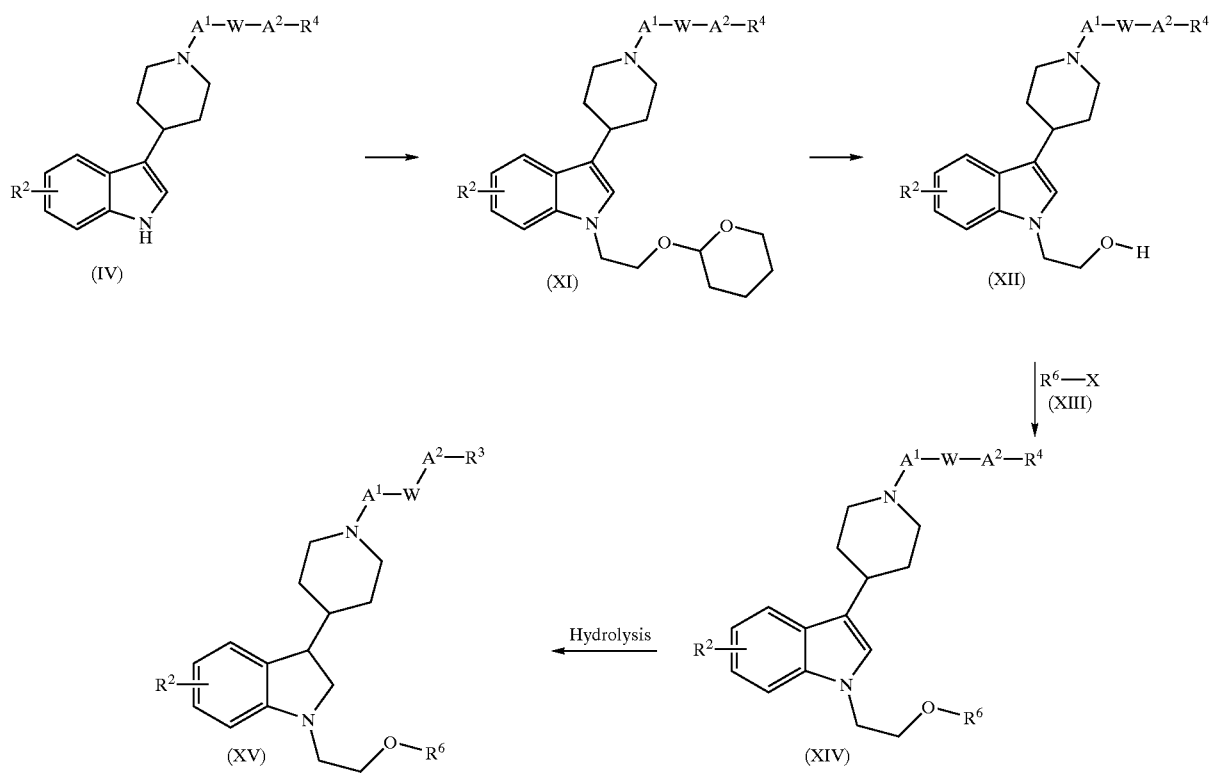

Also included within the scope of the present invention are pharmaceutical compositions which comprise, as the active ingredient, at least one indolylpiperidine derivative of general formula (I), or a pharmacologically-acceptable salt thereof, in association with a pharmaceutically-acceptable carrier or diluent. Preferably the composition is made up in a form suitable for oral, or parenteral administration.

The pharmaceutically-acceptable carriers or diluents which are mixed with the active compound or compounds, or salts thereof, to form the composition of this invention are well-known "per se" and the actual excipients used depend "inter alia" on the intended method of administration of the compositions.

Compositions of this invention are preferably adapted for oral administration. In this case, the composition for oral administration may take the form of tablets, capsules or effervescent granules or liquid preparations such as elixirs, syrups or suspensions, all containing one or more compounds of the invention; such preparations may be made by methods well known in the art.

The diluents which may be used in the preparations of the compositions include those liquid and solid diluents which the active ingredient, together with colouring or flavouring agents, if desired. Tablets or capsules may conveniently contain between 0.2 and 500 mg, preferably from 1 to 100 mg, of active ingredient or the equivalent amount of a pharmacologically-acceptable salt thereof. The compounds may be incorporated into pellets coated with an appropriate natural or synthetic polymers known in the art to produce sustained release characteristics or incorporated with polymers into tablets form to produce the same characteristics.

The liquid composition adapted for oral use may be in the form of solution or suspension. The solutions may be aqueous solution of an acid addition salt of the indolylpiperidine derivative in association with, for example, sucrose or sorbitol to form a syrup. The suspension may comprise an insoluble or micro encapsulated form of an active compound of the invention in association with water of other pharmaceutically-acceptable liquid medium together with a suspending agent or flavouring agent.

Composition for parenteral injection may be prepared from soluble salts of the indolylpiperidine derivative, which may or may not be freeze-dried and which may be dissolved in water or an appropriate parenteral injectable fluid.

In human therapy, the doses of the compound of general formula (I) depend on the desired effect and duration of treatment; adult doses are generally between 0.2 mg and 500 mg per day and preferably between 1 mg and 100 mg per day. In general, the physician will decide the dosing regime taking into account the age and weight of the patient being treated.

Pharmacological Action

The following examples demonstrate the excellent pharmacological activities of the compounds of the present invention. The results of (1) Histamine-$H_1$ receptor binding assay, (2) histamine-induced skin vascular permeability in rats with the monitoring of antiallergic activity, (3) $H_1$ ex vivo binding studies in mice with the monitoring of degree of penetration into brain and (4) measurement of blood pressure and heart rate in conscious unrestrained hypertensive rats with the monitoring of cardiovascular effects, were obtained as described below.

(1) Histamine-$H_1$ receptor binding assay

Binding to the histamine-$H_1$ receptors was performed in guinea pig cerebellum membranes as described previously (Chang, Raymond S.L. et al., Journal of Neurochemistry (1979) 32:1653–1663). Briefly, the membrane suspensions (160 µg/ml) were incubated at 30° C. with 0.7 nM [$^3$H]- mepyramine and different concentrations of the test compounds in a final volume of 250 µl. Binding reactions were terminated by filtration after 30 min of incubation and the bound radioactivity was determined. The specific binding was measured in the presence of 10 µM of promethazine. The affinity of each test compound to the receptor was determined by using at least six different concentrations run in duplicate. $IC_{50}$ values were obtained by non-linear regression by use of SAS on a DEC AXP computer.

TABLE 1

| COMPOUNDS | BINDING TO RECEPTOR $H_1$ ( $IC_{50}$ nM ) |
|---|---|
| CETIRIZINE | 226 |
| FEXOFENADINE | 214 |
| Example 1 | 310 |
| Example 2 | 57 |
| Example 3 | 347 |
| Example 10 | 145 |
| Example 15 | 88 |
| Example 19 | 89 |
| Example 32 | 59 |
| Example 34 | 127 |
| Example 38 | 174 |
| Example 40 | 210 |
| Example 41 | 111 |
| Example 54 | 106 |
| Example 66 | 248 |
| Example 85 | 152 |
| Example 108 | 275 |
| Example 134 | 86 |
| Example 137 | 150 |
| Example 138 | 86 |
| Example 139 | 205 |
| Example 140 | 83 |
| Example 141 | 97 |
| Example 142 | 386 |
| Example 143 | 222 |
| Example 145 | 116 |
| Example 148 | 127 |
| Example 149 | 142 |
| Example 150 | 121 |
| Example 153 | 245 |
| Example 157 | 140 |
| Example 158 | 104 |
| Example 159 | 68 |

Our results show that the compounds of the present invention have affinities for the $H_1$ receptors very similar to the reference compounds.

(2) Histamine-induced skin vascular permeability in rats

Male Wistar rats (180–210 g) were treated orally with the test compound or vehicle. One, 4, 8 and 24 hours later, the rats were lightly anaesthetized with ether. The cutaneous reaction was induced by two intradermal injections of 50 µl of histamine (100 µg/ml) onto the back, followed by a intravenous injection of 3 ml/kg of Evan's Blue (5 mg/ml), both dissolved in saline. Sixty min later, the rats were killed by cervical dislocation and the back skin dissected free. The diameter (in millimeters) of the wheal was measured in two directions and the area was calculated. Results are given as the % of inhibition at a given dose compared with the vehicle treated group.

The compounds disclosed in examples 2, 41, 108, 138, 140, 141, 142, 148, 149, 150, 157 and 158 show an inhibition>50% of the histamine-induced wheal at the dose of 3 mg/Kg 4 hours after administration (in the same experimental conditions, cetirizine and fexofenadine show an inhibition of 36% and 21%, respectively).

(3) $H_1$ ex vivo binding studies in mice

The assay was performed essentially as described by Leysen, Josee E. et al., Drug Development Research (1991) 22:165–178, with the following modifications. Overnight starved male Swiss albino mice ((21 Å2 g) were treated orally with different doses of the test compounds (10 ml/kg, p.o.) and 90 minutes later were killed. The whole brain was dissected out and homogenized in 10 ml of ice-cold 0.05 M $Na^+/K^+$ phosphate buffer (pH 7.4). A 1 ml aliquot of the homogenate was incubated, in triplicate, with 0.1 ml [$^3$H]-mepyramine (2 nM final concentration, 27 Ci/mmol, Amersham) during 40 minutes at 30° C. The [$^3$H]-mepyramine bound to the membranes was determined by immediate filtration of the homogenates under vacuum onto the glass fibre filters (Whatman GF/B) followed by three rapid rinses with 5 ml of cold buffer containing 10 µM cold mepyramine. The radioactivity bound in the filters was determined by liquid scintillation spectrometry. The non-specific binding was determined by treating the animals with 30 mg/kg p.o. D-chlorpheniramine maleate. Mice treated with vehicle (methylcellulose 0.5% and tween 0.1%) were used to determine the total binding. Results are expressed as the % of specific binding at a given dose of the test compound.

The compounds of the present invention display little or no penetration of the blood brain barrier.

(4) Measurement of blood pressure and heart rate in conscious unrestrained hypertensive rats Adult male spontaneously hypertensive rats (SHR) were operated upon in order to implant blood pressure sensors in the abdominal aorta just above the iliac bifurcation. After recovery from anaesthesia, rats were housed individually in cages placed on radio-frequency receivers. Amoxycilline (15 mg/kg, i.m., after surgery) was administered to prevent infection. The rats were allowed to recover for at least 2 weeks after transmitter implantation. Arterial blood pressure and heart rate were recorded and analysed by Dataquest V system (Data Science, St. Paul, Minn.). The animals were kept on a 12:12 hours light-dark cycle during the entire recording period. After 18 hours of fasting with water "ad libitum", the animals received drugs orally and then given food. Hemodynamic recordings were taken every 15 minutes, starting 4 hours before drug administration and continuing up to 24 hours after. Each recording lasted 10 seconds, and the hemodynamic values of all cycles within this period were averaged. All the animals received all the treatments, between administrations in the same rat, there was a seven day wash-out period, and a complete recovery to base-line values was ascertain. The effects of treatments on mean arterial blood pressure and heart rate were determined with one-way analysis of variance (ANOVA). A P value<0.05 was considered statistically significant.

The compounds of the present invention have little or no effects on blood pressure and heart rate at doses from 3 to 30 mg/kg.

From the above described results one of ordinary skill in the art can readily understand that the compounds of the present invention have excellent antihistamine and antiallergic activities. Compounds of the present invention have reduced cardiovascular and central nervous system side effects and are thus useful for the treatment of various allergic disorders, for instance, bronchial asthma, rhinitis, conjunctivitis, dermatitis and urticaria.

The present invention will be further illustrated by the following Examples. The Examples are given by way of illustration only and are not to be construed as limiting.

EXAMPLE 1

Preparation of 2-(2-{4-[1-(4-fluoro-benzyl)-1H-indol-3-yl]-piperidin-1-yl}-ethoxy)-benzoic acid A. Preparation of 3-(1,2,3,6-tetrahydro-pyridin-4-yl)-1H-indole Indole (30 g, 0.26 mol) was dissolved in a solution of potassium hydroxide (77.6 g, 1.38 mol) in methanol (692 ml). 4-piperidone monohydrate hydrochloride (102.3 g, 0.66 mol) was added in one portion and the mixture was heated to reflux for 5 h. Potassium chloride precipitated upon cooling at room temperature and the salt was filtered. The liquid phase was concentrated until only one third of the liquid remained in the round-bottom flask. The solid formed during the concentration of the liquid phase was filtered and washed thoroughly with ethanol and, finally, with ethyl ether. 31.9 g (63% of yield) of the final product was obtained.

Melting point=183–185° C.

B. Preparation of 3-piperidin-4-yl-1H-indole 19.03 g (0.096 mol) of 3-(1,2,3,6-tetrahydro-pyridin-4-yl)-1H-indole were hydrogenated in a Parr apparatus during 18 h at 40 psi with 2.2 g of Pd/C 10% in 600 ml of methanol. After usual work-up, 16.76 g (87% of yield) of the desired product were obtained.

Melting point=210–212° C.

C. Preparation of 2-(2-chloro-ethoxy)-benzoic acid methyl ester

To 25 g (0.16 mol) of methyl salicylate in 250 ml of methyl ethyl ketone 34 g (0.25 mol) of potassium carbonate were added. This mixture was refluxed for 1 h and 27.3 ml (0.35 mol) of 1-bromo-2-chloro-ethane were added and taken to reflux again. Four hours later, 34 g (0.25 mol) more of potassium carbonate and 16.3 ml (0.2 mol) more of 1-bromo-2-chloro-ethane were added. This operation was repeated until the reaction was completed. Then the inorganic salts were filtered and the liquid phase was diluted with the same volume of hexane. This organic phase was washed twice with water and worked-up as usual. The yield in this step was quantitative and the product was pure enough for the next synthetic step.

D. Preparation of 2-{2-[4-(1H-indol-3-yl)-piperidin-1-yl]-ethoxy}-benzoic acid methyl ester 0.22 g (0.5 mmol) of 2-(2-chloro-ethoxy)-benzoic acid methyl ester were added to a mixture of 0.1 g (0.5 mmol) of 3-piperidin-4-yl-1H-indole, 0.08 g (0.6 mmol) of potassium carbonate and 0.04 g (0.2 mmol) of potassium iodide in 1.5 mL of isobutyl methyl ketone under nitrogen atmosphere and the reaction mixture was refluxed for 18 hours. After cooling at room temperature 1.5 mL of dichloromethane and 0.08 g (0.1 mmol) of polystyrene methyl isocyanate were added and the mixture was stirred at this temperature for 3 hours. After filtering, the solution was placed directly on a 500 mg Varian SCX ion exchange column. The columns were washed with 5 mL of methanol and the product was eluted with 5 mL of methanol/ammonia 20:1 affording, after removal of the solvent at reduced pressure, 0.113 g (60% yield) of 2-{2-[4-(1H-indol-3-yl)-piperidin-1-yl]-ethoxy}-benzoic acid methyl ester as a yellow oil.

E. Preparation of 2-(2-{4-[1-(4-fluoro-benzyl)-1H-indol-3-yl]-piperidin-1-yl}-ethoxy)-benzoic acid 0.02 g (0.42 mmol) of a dispersion of 60% NaH in mineral oil were added to a solution of 0.06 g (0.15 mmol) of 2-{2-[4-(1H-indol-3-yl)-piperidin-1-yl]-ethoxy}-benzoic acid methyl ester prepared in step D in 1 mL of anhydrous DMF under nitrogen atmosphere. After stirring 30 minutes at room temperature 0.026 mL (0.21 mmol) of 4-fluoro-benzyl bromide were added and the mixture was stirred for 18 hours. After addition of 0.09 g (0.12 mmol) of 3-(3-mercapto-phenyl)-propanamido-methyl-polystyrene in 1 mL of DMF the mixture was stirred overnight at room temperature. 0.1 mL of 2N HCl were added to the reaction mixture and the crude-was filtered. The solvent was removed under reduced pressure and the crude mixture was purified using a 500 mg Varian C18 chromatography column affording 0.059 g (84% yield) of 2-(2-{4-[1-(4-fluoro-benzyl)-1H-indol-3-yl]-piperidin-1-yl}-ethoxy)-benzoic acid.

ESI/MS m/e=473 [(M+1)$^+$, $C_{26}H_{32}$ F $N_2$ $O_4$]

NMR (300 MHz, CDCl$_3$) d=2.04–2.06 (m, 4H), 2.45–2.46 (m, 2H), 2.90–2.91 (m, 3H), 3.18–3.22 (d, 2H), 4.20–5.00 (brm, 1H), 5.23 (s, 2H), 6.94–7.23 (m, 10H), 7.42–7.47 (t, 1H), 7.59–7.61 (d, 2H), 7.89–7.92 (d, 2H)

Example 2

Preparation of 2-{2-[4-(1-pentyl-1H-indol-3-yl)-piperidin-1-yl]-ethoxy}-benzoic acid The procedure described in Example 1 was performed using 0.1 g (0.5 mmol) of 3-piperidin-4-yl-1H-indole and 0.22 g (0.5 mmol) of 2-(2-chloro-ethoxy)-benzoic acid methyl ester. 0.06 g (0.15 mmol) of the crude, obtained as in step D, were then alkylated with 0.03 mL (0.21 mmol) of pentyl iodide affording 0.052 g (83% yield) of 2-{2-[4-(1-pentyl-1H-indol-3-yl)-piperidin-1-yl]-ethoxy}-benzoic acid.

Melting point=113° C.

ESI/MS m/e=435 [(M+1)$^+$, C27H34 N2 O3]

NMR (CDCl$_3$) d=0.86–0.90 (t, 3H), 1.25–1.36 (m, 6H), 1.74–1.84 (m, 2H), 2.05–2.14 (m, 4H), 2.55–2.70 (m, 2H), 2.94–3.12 (m, 5H), 3.24–3.28 (d, 2H), 3.99–4.06 (t, 2H), 4.44–4.50 (m, 2H), 4.70–5.20 (bs, 1H), 6.89–7.31 (m, 5H), 7.38–7.43 (t, 1H), 7.55–7.58 (d, 1H), 7.84–7.86 (d, 1H)

EXAMPLE 3

Preparation of 4-{4-[1-(2-ethoxy-ethyl)-1H-indol-3-yl]-piperidin-1-yl}-butyric acid The procedure described in Example 1 was performed using 0.1 g (0.5 mmol) of 3-piperidin-4-yl-1H-indole and 0.22 g (0.5 mmol) of 4-chloro-butyric acid ethyl ester. 0.07 g (0.22 mmol) of the crude, obtained as in step D, were then alkylated with 0.04 mL (0.31 mmol) of bromoethyl ethyl ether affording 0.061 g (77% yield) of 4-{4-[1-(2-ethoxy-ethyl)-1H-indol-3-yl]-piperidin-1-yl}-butyric acid.

ESI/MS m/e=359 [(M+1)$^+$,C21H30 N2 O4]

NMR (CDCl$_3$) d=1.13–1.18 (t, 3H), 1.90–2.00 (m, 2H), 2.08–2.20 (m, 4H), 2.45–2.55 (m, 4H), 2.84–2.86 (d, 2H), 2.95–3.00 (m, 1H), 3.38–3.48 (m, 4H), 3.70–3.74 (t, 2H), 4.22–4.26 (t, 2H), 5.00 (bs, 1H), 6.97–7.24 (m, 3H), 7.34–7.37 (d, 1H), 7.57–7.59 (d, 1H)

EXAMPLE 4

Preparation of 3-(3-{4-[1-(4-fluoro-benzyl)-1H-indol-3-yl]-piperidin-1-yl}-propoxy)-benzoic acid The procedure described in Example 1 was performed using 0.2 g (1 mmol) of 3-piperidin-4-yl-1H-indole and 0.25 g (1.1 mmol) of 3-(2-chloropropoxy)benzoic acid methyl ester. 0.08 g (0.20 mmol) of the crude, obtained as in step D, were then alkylated with 0.036 mL (0.30 mmol) of 4-fluorobenzyl bromide affording 0.051 g (53% yield) of 3-(3-{4-[1-(4-fluoro-benzyl)-1H-indol-3-yl]-piperidin-1-yl}-propoxy)-benzoic acid ESI/MS m/e=487 [(M+1)⁺, C30H31 F N2 O3]

NMR (CDCl₃) d=NMR (300 MHz, CDCl₃) d=2.19–2.22 (m, 6H), 2.60–2.75 (m, 2H), 3.02–3.07 (m, 3H), 3.40–3.60 (m, 2H), 4.11–4.15 (t, 2H), 5.23 (s, 2H), 6.93–7.25 (m, 8H), 7.51–7.65 (m, 5H)

EXAMPLE 5

Preparation of 4-{3-[4-(1-pentyl-1H-indol-3-yl)-piperidin-1-yl]-propoxy}-benzoic acid The procedure described in Example 1 was performed using 0.2 g (1 mmol) of 3-piperidin-4-yl-1H-indole and 0.25 g (1.1 mmol) of 4-(2-chloropropoxy)-benzoic acid methyl ester. 0.08 g (0.20 mmol) of the crude, obtained as in step D, were then alkylated with 0.04 mL (0.30 mmol) of pentyl iodide affording 0.023 g (26% yield) of 4-{3-[4-(1-pentyl-1H-indol-3-yl)-piperidin-1-yl]-propoxy}-benzoic acid.

ESI/MS m/e=449 [(M+1)⁺, C28H36 N2 O3]

NMR (CDCl₃) d=0.85–0.95 (m, 3H), 1.26–1.39 (m, 4H), 1.64–1.83 (m, 2H), 1.99–2.16 (m, 5H), 2.16–2.48 (t, 2H), 2.48–3.40 (m, 6H), 4.03–4.08 (t, 2H), 4.11–4–15 (t, 2H), 6.82–7.32 (m, 6H), 7.61–7.63 (d, 1H), 7.84–7.89 (d, 2H)

EXAMPLE 6

Preparation of 2-[2-(4-{1-[2-(2-methoxy-ethoxy)-ethyl]-1H-indol-3-yl}-piperidin-1-yl)-ethoxy]-benzoic acid The procedure described in Example 1 was performed using 0.2 g (1 mmol) of 3-piperidin-4-yl-1H-indole and 0.17 g (1.1 mmol) of 2-(2-chloro-ethoxy)-benzoic acid methyl ester. 0.07 g (0.21 mmol) of the crude, obtained as in step D, were then alkylated with 0.04 mL (0.31 mmol) of 1-bromo-2-(2-methoxy-ethoxy)-ethane affording 0.064 g (65% yield) of 2-[2-(4-{1-[2-(2-methoxy-ethoxy)-ethyl]-1H-indol-3-yl}-piperidin-1-yl)-ethoxy]-benzoic acid.

ESI/MS m/e=467 [(M+1)⁺, C27H34 N2 O5]

NMR (300 MHz, CDCl₃) d=2.00–2.46 (m, 4H), 2.50–2.89 (m, 2H), 2.92–3.20 (m, 3H), 3.24–3.35 (m, 2H), 3.38 (s, 3H), 3.48–3.51 (m, 2H), 3.54–3.57 (m, 2H), 3.78–3.82 (t, 2H), 4.24–4.29 (t, 2H), 4.44–4.48 (t, 2H), 4.60–5.20 (bs, 1H), 6.98–7.59 (m, 8H), 7.90–7.93 (dd, 1H)

EXAMPLE 7

Preparation of 3-[2-(4-{1-[2-(2-methoxy-ethoxy)-ethyl]-1H-indol-3-yl}-piperidin-1-yl)-ethoxy]-benzoic acid The procedure described in Example 1 was performed using 0.2 g (1 mmol) of 3-piperidin-4-yl-1H-indole and 0.17 g (1.1 mmol) of 3-(2-chloro-ethoxy)-benzoic acid methyl ester. 0.06 g (0.19 mmol) of the crude, obtained as in step D, were then alkylated with 0.04 mL (0.31 mmol) of 1-bromo-2-(2-methoxy-ethoxy)-ethane affording 0.053 g (60% yield) of 3-[2-(4-{1-[2-(2-methoxy-ethoxy)-ethyl]-1H-indol-3-yl}-piperidin-1-yl)-ethoxy]-benzoic acid.

ESI/MS m/e=467 [(M+1)⁺, C27H34 N2 O5]

NMR (300 MHz, CDCl₃) d=2.21–2.39 (m, 4H), 2.84–3.07 (m, 4H), 3.32 (s, 3H), 3.35–3.53 (m, 5H), 3.75–3.79 (m, 4H), 4.23–4.27 (t, 2H), 4.50–4.53 (m, 2H), 6.99–7.35 (m, 5H), 7.59–7.68 (m, 4H)

EXAMPLE 8

Preparation of 3-(2-{4-[1-(4-fluoro-benzyl)-1H-indol-3-yl]-piperidin-1-yl}-ethoxy)-benzoic acid The procedure described in Example 1 was performed using 0.2 g (1 mmol) of 3-piperidin-4-yl-1H-indole and 0.17 g (1.1 mmol) of 3-(2-chloro-ethoxy)-benzoic acid methyl ester. 0.06 g (0.19 mmol) of the crude, obtained as in step D, were then alkylated with 0.03 mL (0.28 mmol) of 4-fluorobenzyl bromide affording 0.047 g (52% yield) of 3-(2-{4-[1-(4-fluoro-benzyl)-1H-indol-3-yl]-piperidin-1-yl}-ethoxy)-benzoic acid.

ESI/MS m/e=473 [(M+1)⁺, C29H29 F N2 O3]

NMR (300 MHz, CDCl₃) d=2.10–2.45 (m, 4H), 2.83–2.89 (m, 2H), 3.26–3.36 (m, 3H), 3.53–3.57 (m, 2H), 4.38–4.41 (t, 2H), 5.26 (s, 2H), 6.94–7.38 (m, 9H), 7.61–7.69 (m, 4H)

EXAMPLE 9

Preparation of 3-{2-[4-(1-pentyl-1H-indol-3-yl)-piperidin-1-yl]-ethoxy}-benzoic acid The procedure described in Example 1 was performed using 0.2 g (1 mmol) of 3-piperidin-4-yl-1H-indole and 0.17 g (1.1 mmol) of 3-(2-chloro-ethoxy)-benzoic acid methyl ester. 0.06 g (0.19 mmol) of the crude, obtained as in step D, were then alkylated with 0.035 mL (0.28 mmol) of pentyl iodide affording 0.037 g (45% yield) of 3-{2-[4-(1-pentyl-1H-indol-3-yl)-piperidin-1-yl]-ethoxy}-benzoic acid.

ESI/MS m/e=435 [(M+1)⁺, C27H34 N2 O3]

NMR (300 MHz, CDCl₃) d=0.86–0.90 (t, 3H), 1.30–1.41 (m, 4H), 1.60–1.85 (m, 2H), 2.00–2.20 (m, 4H), 2.60–2.80 (m, 2H), 2.95–3.05 (m, 1H), 3.19–3.22 (t, 2H), 3.44–3.47 (d, 2H), 4.05–4.09 (t, 2H), 4.34–4.37 (m, 4H), 6.94–7.67 (m, 9H)

EXAMPLE 10

Preparation of 3-(2-{4-[1-(2-ethoxy-ethyl)-1H-indol-3-yl]-piperidin-1-yl-ethoxy)-benzoic acid The procedure described in Example 1 was performed using 0.2 g (1 mmol) of 3-piperidin-4-yl-1H-indole and 0.17 g (1.1 mmol) of 3-(2-chloro-ethoxy)-benzoic acid methyl ester. 0.06 g (0.19 mmol) of the crude, obtained as in step D, were then alkylated with 0.028 mL (0.28 mmol) of bromo-ethyl ethyl ether affording 0.032 g (38% yield) of 3-(2-{4-[1-(2-ethoxy-ethyl)-1H-indol-3-yl]-piperidin-1-yl-ethoxy)-benzoic acid.

ESI/MS m/e=437 [(M+1)⁺, C26H32 N2 O4]

NMR (300 MHz, CDCl₃) d=1.02–1.14 (t, 3H), 2.10–2.30 (m, 4H), 2.75–2.90 (m, 2H), 2.95–3.15 (m, 1H), 3.20–3.30 (m, 2H), 3.40–3.45 (q, 2H), 3.69–3.73 (m, 4), 4.21–4.24 (t, 2H), 4.40–4.55 (m, 2H), 6.99–7-71 (m, 9H)

EXAMPLE 11

Preparation of 4-[2-(4-{1-[2-(2-methoxy-ethoxy)-ethyl]-1H-indol-3-yl}-piperidin-1-yl)-ethoxy]-benzoic acid The procedure described in Example 1 was performed using 0.2 g (1 mmol) of 3-piperidin-4-yl-1H-indole and 0.18 g (1.1 mmol) of 4-(2-chloro-ethoxy)-benzoic acid ethyl ester. 0.06 g (0.19 mmol) of the crude, obtained as in step D, were then alkylated with 0.04 mL (0.28 mmol) of 1-bromo-2-(2-methoxy-ethoxy)-ethane affording 0.024 g (28% yield) of 4-[2-(4-{1-[2-(2-methoxy-ethoxy)-ethyl]-1H-indol-3-yl}-piperidin-1-yl)-ethoxy]-benzoic acid.

ESI/MS m/e=467 [(M+1)⁺, C27H34 N2 O5]

NMR (300 MHz, CDCl₃) d=1.80–2.00 (m, 2H), 2.05–2.20 (m, 2H), 2.35–2.45 (m, 2H), 2.80–2.99 (m, 3H), 3.19–3.23 (m, 2H), 3.43 (s, 3H), 3.47–3.54 (m, 4H), 3.77–3.82 (t, 2H), 4.24–4.30 (m, 4H), 6.94–7.65 (m, 9H); 8.00–8.02 (d, 2H)

EXAMPLE 12

Preparation of 4-{2-[4-(1-pentyl-1H-indol-3-yl)-piperidin-1-yl]-ethoxy}-benzoic acid The procedure described in Example 1 was performed using 0.2 g (1 mmol) of 3-piperidin-4-yl-1H-indole and 0.18 g (1.1 mmol) of 4-(2-chloro-ethoxy)-benzoic acid ethyl ester. 0.06 g (0.19 mmol) of the crude, obtained as in step D, were then alkylated with 0.03 mL (0.28 mmol) of pentyl iodide affording 0.028 g (34% yield) of 4-{2-[4-(1-pentyl-1H-indol-3-yl)-piperidin-1-yl]-ethoxy}-benzoic acid.

ESI/MS m/e=435 [(M+1)$^+$, C27H34 N2 O3]

NMR (300 MHz, DMSO) d=0.81–0.91 (m, 3H), 1.20–1.38 (m, 4H), 1.65–1.74 (m, 4H), 1.91–1.94 (m, 2H), 2.00–2.15 (m, 1H), 2.18–2.25 (m, 2H), 2.74–2.77 (m, 2H), 2.98–3.07 (m, 2H), 4.03–4.17 (m, 4H), 6.93–7.15 (m, 5H), 7.38–7.43 (m, 1H), 7.54–7.56 (d, 1H), 7.83–7.86 (m, 2H)

EXAMPLE 13

Preparation of 2-[3-(4-{1-[2-(2-methoxy-ethoxy)-ethyl]-1H-indol-3-yl}-piperidin-1-yl)-propoxyl-benzoic acid The procedure described in Example 1 was performed using 0.2 g (1 mmol) of 3-piperidin-4-yl-1H-indole and 0.25 g (1.1 mmol) of 2-(2-chloro-propoxy)-benzoic acid methyl ester. 0.082 g (0.21 mmol) of the crude, obtained as in step D, were then alkylated with 0.04 mL (0.31 mmol) of 1-bromo-2-(2-methoxy-ethoxy)-ethane affording 0.056 g (56% yield) of 2-[3-(4-{1-[2-(2-methoxy-ethoxy)-ethyl]-1H-indol-3-yl}-piperidin-1-yl)-propoxy]-benzoic acid.

ESI/MS m/e=481 [(M+1)$^+$, C28H36 N2 O5]

NMR (300 MHz, CDCl$_3$) d=2.20–2.28 (m, 6H), 2.75–2.92 (m, 2H), 3.00–3.10 (m, 1H), 3.19–3.24 (t, 2H), 3.33 (s, 3H), 3.45–3.54 (m, 4H), 3.62–3.67 (m, 2H), 3.74–3.78 (t, 2H), 4.19–4.25 (m, 4H), 5.20–5.60 (bs, 1H), 6.94–7.38 (m, 7H), 7.54–7.57 (d, 1H), 7.97–8.00 (dd, 1H)

EXAMPLE 14

Preparation of 2-(3-{4-[1-(4-fluoro-benzyl)-1H-indol-3-yl]-piperidin-1-yl}-propoxy)-benzoic acid The procedure described in Example 1 was performed using 0.2 g (1 mmol) of 3-piperidin-4-yl-1H-indole and 0.25 g (1.1 mmol) of 2-(2-chloro-propoxy)-benzoic acid methyl ester. 0.082 g (0.21 mmol) of the crude, obtained as in step D, were then alkylated with 0.04 mL (0.31 mmol) of 4-fluorobenzyl bromide affording 0.062 g (61% yield) of 2-(3-{4-[1-(4-fluoro-benzyl)-1H-indol-3-yl]-piperidin-1-yl}-propoxy)-benzoic acid.

ESI/MS m/e=487 [(M+1)$^+$, C30H31 F N2 O3]

NMR (300 MHz, CDCl$_3$) d=2.20–2.40 (m, 6H), 2.95–3.10 (m, 2H), 3.15–3.22 (m, 1H), 3.34–3.42 (m, 3H), 3.76–3.80 (d, 2H), 4.19–4.23 (m, 4H), 5.27 (s, 2H), 6.93–7.36 (m, 10H), 7.59–7.61 (d, 1H), 7.85–7.88 (dd, 1H)

EXAMPLE 15

Preparation of 2-{3-[4-(1-pentyl-1H-indol-3-yl)-piperidin-1-yl]-propoxy}-benzoic acid The procedure described in Example 1 was performed using 0.2 g (1 mmol) of 3-piperidin-4-yl-1H-indole and 0.25 g (1.1 mmol) of 2-(2-chloro-propoxy)-benzoic acid methyl ester. 0.087 g (0.22 mmol) of the crude, obtained as in step D, were then alkylated with 0.04 mL (0.33 mmol) of pentyl iodide affording 0.057 g (57% yield) of 2-{3-[4-(1-pentyl-1H-indol-3-yl)-piperidin-1-yl]-propoxy}-benzoic acid.

ESI/MS m/e=449 [(M+1)$^+$, C28H36 N2 O3]

NMR (300 MHz, CDCl$_3$) d=0.84–0.89 (t, 3H), 1.27–1.34 (m, 4H), 1.71–2.10 (m, 8H), 2.80–3.32 (m, 7H), 3.80–4.10 (m, 4H), 6.70–7.95 (m, 9H)

EXAMPLE 16

Preparation of 2-(3-{4-[1-(2-ethoxy-ethyl)-1H-indol-3-yl]-piperidin-1-yl}-propoxy)-benzoic acid The procedure described in Example 1 was performed using 0.2 g (1 mmol) of 3-piperidin-4-yl-1H-indole and 0.25 g (1.1 mmol) of 2-(2-chloro-propoxy)-benzoic acid methyl ester. 0.087 g (0.22 mmol) of the crude, obtained as in step D, were then alkylated with 0.03 mL (0.33 mmol) of 2-bromoethyl ethyl ether affording 0.078 g (78% yield) of 2-(3-{4-[1-(2-ethoxy-ethyl)-1H-indol-3-yl]-piperidin-1-yl}-propoxy)-benzoic acid.

ESI/MS m/e=451 [(M+1)$^+$, C27H34 N2 O4]

NMR (300 MHz, CDCl$_3$) d=1.11–1.16 (t, 3H), 2.23–2.34 (m, 8H), 2.90–2.98 (t, 2H), 3.00–3.18 (m, 1H), 3.29–3.33 (t, 2H), 3.69–3.79 (m, 4H), 4.19–4.27 (m, 4H), 6.94–6.97 (d, 1H), 7.07–7.37 (m, 5H), 7.55–7.57 (d, 1H), 7.93–7.96 (dd, 1H)

EXAMPLE 17

Preparation of 3-[3-(4-{1-[2-(2-methoxy-ethoxy)-ethyl]-1H-indol-3-yl}-piperidin-1-yl)-propoxy]-benzoic acid The procedure described in Example 1 was performed using 0.2 g (1 mmol) of 3-piperidin-4-yl-1H-indole and 0.25 g (1.1 mmol) of 3-(2-chloro-propoxy)-benzoic acid methyl ester. 0.080 g (0.20 mmol) of the crude, obtained as in step D, were then alkylated with 0.04 mL (0.30 mmol) of 1-bromo-2-(2-methoxy ethoxy)ethane affording 0.065 g (68% yield) of 3-[3-(4-{1-[2-(2-methoxy-ethoxy)-ethyl]-1H-indol-3-yl}-piperidin-1-yl)-propoxy]-benzoic acid.

ESI/MS m/e=481 [(M+1)$^+$, C28H36 N2 O5]

NMR (300 MHz, CDCl$_3$) d=2.10–2.60 (m, 6H), 2.50–2.65 (m, 2H), 2.92–3.10 (m, 3H), 3.33 (s, 3H), 3.38–3.53 (m, 6H), 3.77–3.80 (t, 2H), 4.11–4.15 (t, 2H), 4.25–4.29 (t, 2H), 6.99–7.56 (m, 7H), 7.61–7.63 (d, 1H)

EXAMPLE 18

Preparation of 3-{3-[4-(1-pentyl-1H-indol-3-yl)-piperidin-1-yl]-propoxy}-benzoic acid The procedure described in Example 1 was performed using 0.2 g (1 mmol) of 3-piperidin-4-yl-1H-indole and 0.25 g (1.1 mmol) of 3-(2-chloro-propoxy)-benzoic acid methyl ester. 0.08 g (0.20 mmol) of the crude, obtained as in step D, were then alkylated with 0.04 mL (0.30 mmol) of pentyl iodide affording 0.042 g (48% yield) of 3-{3-[4-(1-pentyl-1H-indol-3-yl)-piperidin-1-yl]-propoxy}-benzoic acid.

ESI/MS m/e=449 [(M+1)$^+$, C28H36 N2 O3]

NMR (300 MHz, CDCl$_3$) d=0.85–0.94 (m, 3H), 1.26–1.39 (m, 4H), 1.69–1.85 (m, 2H), 2.10–2.25 (m, 6H), 2.58–2.66 (m, 2H), 2.98–3.03 (m, 3H), 3.49–3.53 (m, 2H), 4.03–4.08 (t, 2H), 4.10–4.14 (t, 2H), 6.93–7.56 (m, 8H), 7.60–7.63 (d, 1H)

EXAMPLE 19

Preparation of 3-(3-{4-[1-(2-ethoxy-ethyl)-1H-indol-3-yl]-piperidin-1-yl}-propoxy)-benzoic acid The procedure described in Example 1 was performed using 0.2 g (1 mmol) of 3-piperidin-4-yl-1H-indole and 0.25 g (1.1 mmol) of 3-(2-chloro-propoxy)-benzoic acid methyl ester. 0.08 g (0.20 mmol) of the crude, obtained as in step D, were then alkylated with 0.03 mL (0.30 mmol) of bromoethyl ethyl ether affording 0.055 g (61% yield) of 3-(3-{4-[1-(2-ethoxy ethyl)-1H-indol-3-yl]-piperidin-1-yl}-propoxy)-benzoic acid.

ESI/MS m/e=451 [(M+1)+, C27H34 N2 o4]

NMR (300 MHz, CDCl₃) d=1.10–1.15 (t, 3H), 2.17–2.22 (m, 6H), 2.60–2.75 (m, 2H), 3.03–3.08 (m, 3H), 3.41–3.46 (t, 2H), 3.53–3.57 (m, 2H), 3.71–3.74 (t, 2H), 4.12–4.16 (t, 2H), 4.22–4.26 (t, 2H), 6.96–7.55 (m, 8H), 7.61–7.63 (d, 1H)

EXAMPLE 20

Preparation of 4-[3-(4-{1-[2-(2-methoxy-ethoxy)-ethyl]-1H-indol-3-yl}-piperidin-1-yl)-propoxyl-benzoic acid The procedure described in Example 1 was performed using 0.2 g (1 mmol) of 3-piperidin-4-yl-1H-indole and 0.25 g (1.1 mmol) of 4-(2-chloro-propoxy)-benzoic acid methyl ester. 0.08 g (0.20 mmol) of the crude, obtained as in step D, were then alkylated with 0.04 mL (0.30 mmol) of 1-bromo-2-(2-methoxy-ethoxy)-ethane affording 0.033 g (36% yield) of 4-[3-(4-{1-[2-(2-methoxy-ethoxy)-ethyl]-1H-indol-3-yl}-piperidin-1-yl)-propoxy]-benzoic acid.

ESI/MS m/e=481 [(M+1)+, C28H36 N2 O5]

NMR (300 MHz, CDCl₃) d=2.14–2.19 (m, 6H), 2.40–2.55 (m, 2H), 2.95–2.99 (m, 3H), 3.29–3.57 (m, 6H), 3.73–3.77 (t, 2H), 4.15–4.18 (t, 2H), 4.21–4.25 (t, 2H), 6.71–6.74 (m, 2H), 6.94 (s, 1H), 7.02–7.07 (t, 1H), 7.14–7.20 (t, 1H), 7.26–7.64 (m, 4H)

EXAMPLE 21

Preparation of 4-(3-{4-[1-(2-ethoxy-ethyl)-1H-indol-3-yl]-piperidin-1-yl}-propoxy)-benzoic acid The procedure described in Example 1 was performed using 0.2 g (1 mmol) of 3-piperidin-4-yl-1H-indole and 0.25 g (1.1 mmol) of 4-(2-chloro-propoxy)-benzoic acid methyl ester. 0.08 g (0.20 mmol) of the crude, obtained as in step D, were then alkylated with 0.03 mL (0.30 mmol) of bromo-ethyl ethyl ether affording 0.029 g (33% yield) of 4-(3-{4-[1-(2-ethoxy- ethyl)-1H-indol-3-yl]-piperidin-1-yl}-propoxy)-benzoic acid.

ESI/MS m/e=451 [(M+1)+, C27H34 N2 O4]

NMR (300 MHz, CDCl₃) d=1.07–1.12 (t, 3H), 2.11–2.17 (m, 6H), 2.43–2.96 (m, 5H), 3.35–3.42 (q, 2H), 3.50–3.54 (m, 2H), 3.66–3.70 (t, 2H), 4.16–4.22 (m, 4H), 6.71–6.74 (d, 2H), 6.92 (s, 1H), 7.02–7.07 (t, 1H), 7.14–7.20 (t, 1H), 7.27–7.33 (m, 1H) 7.59–7.62 (m, 3H)

EXAMPLE 22

Preparation of 3-(4-{1-[2-(2-methoxy-ethoxy)-ethyl]-1H-indol-3-yl}-piperidin-1-yl)-propionic acid The procedure described in Example 1 was performed using 0.2 g (1 mmol) of 3-piperidin-4-yl-1H-indole and 0.15 g (1.1 mmol) of 3-chloro-propionic acid ethyl ester. 0.08 g (0.25 mmol) of the crude, obtained as in step D, were then alkylated with 0.05 mL (0.38 mmol) of 1-bromo-2-(2-methoxy-ethoxy)-ethane affording 0.078 g (84% yield) of 3-(4-{1-[2-(2-methoxy-ethoxy)-ethyl]-1H-indol-3-yl}-piperidin-1-yl)-propionic acid.

ESI/MS m/e=375 [(M+1)+, C21H30 N2 O4]

NMR (300 MHz, CDCl₃) d=2.01–2.10 (m, 2H), 2.24–2.28 (m, 2H), 2.30–2.45 (m, 4H), 2.57–2.61 (t, 2H), 2.70–2.80 (m, 2H), 3.04–3.08 (t, 2H), 3.37 (s, 3H), 3.50–3.81 (m, 4H), 3.79–3.81 (t, 2H), 4.28–4.32 (t, 2H), 7.00 (s, 1H), 7.09–7.14 (t, 1H), 7.20–7.25 (t, 1H), 7.36–7.39 (d, 1H), 7.56–7.59 (d, 1H)

EXAMPLE 23

Preparation of 3-[4-(1-pentyl-1H-indol-3-yl)-piperidin-1-yl]-propionic acid

The procedure described in Example 1 was performed using 0.2 g (1 mmol) of 3-piperidin-4-yl-1H-indole and 0.15 g (1.1 mmol) of 3-chloro-propionic acid ethyl ester. 0.04 g (0.14 mmol) of the crude, obtained as in step D, were then alkylated with 0.03 mL (0.21 mmol) of pentyl iodide affording 0.022 g (47% yield) of 3-[4-(1-pentyl-1H-indol-3-yl)-piperidin-1-yl]-propionic acid.

ESI/MS m/e=343 [(M+1)+, C21H30 N2 O2]

NMR (300 MHz, CDCl₃) d=0.87–0.94 (m, 3H), 1.21–1.40 (m, 6H), 1.75–1.84 (m, 3H), 1.99–2.04 (m, 2H), 2.19–2.24 (m, 2H), 2.64–2.68 (m, 2H), 2.99–3.02 (d, 2H), 3.43–3.53 (m, 4H), 4.03–4.08 (t, 2H), 6.89 (s, 1H), 7.07–7.34 (m, 3H), 7.57–7.59 (d, 1H)

EXAMPLE 24

Preparation of 4-(4-{1-[2-(2-methoxy-ethoxy)-ethyl]-1H-indol-3-yl}-piperidin-1-yl)-butyric acid The procedure described in Example 1 was performed using 0.2 g (1 mmol) of 3-piperidin-4-yl-1H-indole and 0.17 g (1.1 mmol) of 4-chloro-butyric acid ethyl ester. 0.07 g (0.22 mmol) of the crude, obtained as in step D, were then alkylated with 0.04 mL (0.33 mmol) of 1-bromo-2-(2-methoxy-ethoxy)-ethane affording 0.068 g (79% yield) of 4-(4-{1-[2-(2-methoxy-ethoxy)-ethyl]-1H-indol-3-yl}-piperidin-1-yl)-butyric acid.

ESI/MS m/e=389 [(M+1)+, C22H32 N2 O4]

NMR (300 MHz, CDCl₃) d=1.90–1.99 (m, 2H), 2.10–2.23 (m, 4H), 2.60–2.79 (m, 6H), 2.89–3.04 (m, 3H), 3.36 (s, 3H), 3.48–3.57 (m, 4H), 3.78–3.82 (t, 2H), 4.26–4.30 (t, 2H), 7.02 (s, 1H), 7.08–7.10 (t, 1H), 7.19–7.24 (t, 1H), 7.35–7.38 (d, 1H), 7.55–7.58 (d, 1H)

EXAMPLE 25

Preparation of 4-{4-[1-(4-fluoro-benzyl)-1H-indol-3-yl]-piperidin-1-yl}-butyric acid The procedure described in Example 1 was performed using 0.2 g (1 mmol) of 3-piperidin-4-yl-1H-indole and 0.17 g (1.1 mmol) of 4-chloro-butyric acid ethyl ester. 0.07 g (0.22 mmol) of the crude, obtained as in step D, were then alkylated with 0.04 mL (0.33 mmol) of 4-fluoro-benzyl bromide affording 0.074 g (85% yield) of 4-{4-[1-(4-fluoro-benzyl)-1H-indol-3-yl]-piperidin-1-yl}-butyric acid.

ESI/MS m/e=395 [(M+1)+, C24H27 F N2 O2]

NMR (300 MHz, CDCl₃) d=1.80–1.95 (m, 2H), 2.00–2.14 (m, 4H), 2.48–2.60 (m, 4H), 2.74–2.78 (t, 2H), 2.94–3.00 (m, 2H), 3.29–3.33 (m, 2H), 5.21 (s, 2H), 6.90–7.27 (m, 9H), 7.59–7.62 (m, 2H).

EXAMPLE 26

Preparation of 4-[4-(1-pentyl-1H-indol-3-yl)-piperidin-1-yl]-butyric acid

The procedure described in Example 1 was performed using 0.2 g (1 mmol) of 3-piperidin-4-yl-1H-indole and 0.17 g (1.1 mmol) of 4-chloro-butyric acid ethyl ester. 0.06 g (0.20 mmol) of the crude, obtained as in step D, were then alkylated with 0.04 mL (0.33 mmol) of pentyl iodide affording 0.054 g (76% yield) of 4-[4-(1-pentyl-1H-indol-3-yl)-piperidin-1-yl]-butyric acid.

ESI/MS m/e=357 [(M+1)$^+$, C22H32 N2 O2]

NMR (300 MHz, CDCl$_3$) d=0.87–0.92 (t, 3H), 1.27–1.36 (m, 4H), 1.77–1.92 (m, 4H), 2.04–2.17 (m, 4H), 2.55–2.66 (m, 4H), 2.81–2.84 (t, 2H), 2.95–3.05 (m, 1H), 3.35–3.39 (m, 2H), 4.03–4.08 (t, 2H), 6.91 (s, 1H), 7.07–7.09 (t, 1H), 7.19–7.34 (m, 2H), 7.57–7.60 (d, 1H)

EXAMPLE 27

Preparation of 3-{4-[2-(4-{1-[2-(2-methoxy-ethoxy)-ethyl]-1H-indol-3-yl}-piperidin-1-yl)-ethyl]-phenyl}-propionic acid The procedure described in Example 1 was performed using 0.2 g (1 mmol) of 3-piperidin-4-yl-1H-indole and 0.31 g (1.1 mmol) of 3-[4-(2-bromo-ethyl)-phenyl]-propionic acid ethyl ester. 0.08 g (0.20 mmol) of the crude, obtained as in step D, were then alkylated with 0.04 mL (0.33 mmol) of 1-bromo-2-(2-methoxy-ethoxy)-ethane affording 0.066 g (72% yield) of 3-{4-[2-(4-{1-[2-(2-methoxy-ethoxy)-ethyl]-1H-indol-3-yl}-piperidin-1-yl)-ethyl]-phenyl}-propionic acid.

ESI/MS m/e=479 [(M+1)$^+$, C29H38 N2 O4]

NMR (300 MHz, CDCl$_3$) d=2.00–2.22 (m, 4H), 2.61–2.74 (m, 6H), 2.88–3.10 (m, 5H), 3.62 (s, 3H), 3.48–3.56 (m, 6H), 3.79–3.83 (t, 2H), 4.27–4.31 (t, 2H), 6.93–7.40 (m, 8H), 7.58–7.61 (d, 1H)

EXAMPLE 28

Preparation of 3-{4-[1-(4-fluoro-benzyl)-1H-indol-3-yl]-piperidin-1-yl}-propionic acid The procedure described in Example 1 was performed using 0.2 g (1 mmol) of 3-piperidin-4-yl-1H-indole and 0.15 g (1.1 mmol) of 3-chloropropionic acid ethyl ester. 0.08 g (0.25 mmol) of the crude, obtained as in step D, were then alkylated with 0.04 mL (0.38 mmol) of 4-fluorobenzyl bromide affording 0.067 g (71% yield) of 3-{4-[1-(4-fluorobenzyl)-1H-indol-3-yl]-piperidin-1-yl}-propionic acid.

ESI/MS m/e=381 [(M+1)$^+$, C23H25 F N2 O2]

NMR (300 MHz, CDCl$_3$) d=2.06–2.14 (m, 2H), 2.30–2.34 (m, 2H), 2.55–2.60 (t, 2H), 2.90–2.98 (t, 2H), 3.10–3.22 (m, 3H), 3.59–3.63 (m, 2H), 5.26 (s, 2H), 6.96–7.29 (m, 8H), 7.59–7.62 (dd, 1H)

EXAMPLE 29

Preparation of 3-[4-(2-{4-[1-(2-ethoxy-ethyl)-1H-indol-3-yl]-piperidin-1-yl}-ethyl)-phenyl]-propionic acid The procedure described in Example 1 was performed using 0.2 g (1 mmol) of 3-piperidin-4-yl-1H-indole and 0.31 g (1.1 mmol) of 3-[4-(2-bromo-ethyl)-phenyl]-propionic acid ethyl ester. 0.08 g (0.20 mmol) of the crude, obtained as in step D, were then alkylated with 0.03 mL (0.33 mmol) of bromoethyl ethyl ether affording 0.054 g (64% yield) of 3-[4-(2-{4-[1-(2-ethoxy-ethyl)-1H-indol-3-yl]-piperidin-1-yl}-ethyl)-phenyl]-propionic acid.

ESI/MS m/e=449 [(M+1)$^+$, C28H36 N2 O3]

NMR (300 MHz, CDCl$_3$) d=1.13–1.18 (t, 3H), 2.00–2.15 (m, 4H), 2.51–2.98 (m, 11H), 3.40–3.54 (m, 4H), 3.70–3.74 (t, 2H), 4.22–4.26 (t, 2H), 6.87–7.26 (m, 7H), 7.33–7.36 (d, 1H), 7.57–7.60 (dd, 1H)

EXAMPLE 30

Preparation of 3-{4-[2-(4-{1-[2-(2-methoxy-ethoxy)-ethyl]-1H-indol-3-yl}-piperidin-1-yl)-ethyl]-phenyl}-acrylic acid The procedure described in Example 1 was performed using 0.2 g (1 mmol) of 3-piperidin-4-yl-1H-indole and 0.2 g (1.1 mmol) of 3-[4-(2-bromo-ethyl)-phenyl]-acrylic acid ethyl ester. 0.04 g (0.10 mmol) of the crude, obtained as in step D, were then alkylated with 0.02 mL (0.15 mmol) of 1-bromo-2-(2-methoxy-ethoxy)-ethane affording 0.020 g (41% yield) of 3-{4-[2-(4-{1-[2-(2-methoxy-ethoxy)-ethyl]-1H-indol-3-yl}-piperidin-1-yl)-ethyl]-phenyl}-acrylic acid.

ESI/MS m/e=477 [(M+1)$^+$, C29H36 N2 O4]

NMR (300 MHz, CDCl$_3$) d=2.10–2.22 (m, 4H), 2.60–2.65 (m, 2H), 2.98–3.09 (m, 5H), 3.36 (s, 3H), 3.47–3.62 (m, 6H), 3.76–3.80 (t, 2H), 4.24–4.28 (t, 2H), 6.31–6.37 (d, 1H), 6.99–7.62 (m, 10H)

EXAMPLE 31

Preparation of 3-(4-{2-[4-(1-pentyl-1H-indol-3-yl)-piperidin-1-yl]-ethyl}-phenyl)-acrylic acid The procedure described in Example 1 was performed using 0.2 g (1 mmol) of 3-piperidin-4-yl-1H-indole and 0.2 g (1.1 mmol) of 3-[4-(2-bromo-ethyl)-phenyl]-acrylic acid ethyl ester. 0.03 g (0.08 mmol) of the crude, obtained as in step D, were then alkylated with 0.02 mL (0.15 mmol) of pentyl iodide affording 0.013 g (36% yield) of 3-(4-{2-[4-(1-pentyl-1H-indol-3-yl)-piperidin-1-yl]-ethyl}-phenyl)-acrylic acid.

ESI/MS m/e=445 [(M+1)$^+$, C29H38 N2 O2]

NMR (300 MHz, CDCl$_3$) d=0.85–0.94 (m, 3H), 1.22–2.20 (m, 12H), 2.38–2.45 (m, 2H), 2.96–3.04 (m, 3H), 3.45–3.49 (m, 2H), 4.01–4.06 (t, 2H), 6.22–6.27 (d, 1H), 6.89–7.62 (m, 10H)

EXAMPLE 32

Preparation of 3-[4-(2-{4-[1-(2-ethoxy-ethyl)-1H-indol-3-yl]-piperidin-1-yl}-ethyl)-phenyl]-acrylic acid The procedure described in Example 1 was performed using 0.2 g (1 mmol) of 3-piperidin-4-yl-1H-indole and 0.2 g (1.1 mmol) of 3-[4-(2-bromo-ethyl)-phenyl]-acrylic acid ethyl ester. 0.03 g (0.08 mmol) of the crude, obtained as in step D, were then alkylated with 0.02 L (0.15 mmol) of bromoethyl ethyl ether affording 0.018 g (51% yield) of 3-[4-(2-{4-[1-(2-ethoxy-ethyl)-1H-indol-3-yl]-piperidin-1-yl}-ethyl)-phenyl]-acrylic acid.

ESI/MS m/e=447 [(M+1)$^+$, C28H34 N2 O3]

NMR (300 MHz, CDCl$_3$) d=1.11–1.53 (t, 3H), 2.00–2.20 (m, 4H), 2.40–2.60 (m, 2H), 2.80–3.20 (m, 5H), 3.38–3.54 (m, 4H), 3.68–3.72 (t, 2H), 4.20–4.24 (t, 2H), 6.26–6.31 (d, 1H), 6.96–7.44 (m, 9H), 7.50–7.62 (d, 1H)

EXAMPLE 33

Preparation of 2-{4-[1-hydroxy-4-(4-{1-[2-(2-methoxy-ethoxy)-ethyl]-1H-indol-3-yl}-piperidin-1-yl)-butyl]-phenyl}-2-methyl-propionic acid The procedure described in Example 1 was performed using 0.2 g (1 mmol) of 3-piperidin-4-yl-1H-indole and 0.31 g (1.1 mmol) of 2-[4-(4-chloro-1-hydroxy-butyl)-phenyl]-2-methyl-propionic acid methyl ester. 0.04 g (0.1 mmol) of the crude, obtained as in step D, were then alkylated with 0.02 mL (0.15 mmol) of 1-bromo-2-(2-methoxy-ethoxy)-ethane affording 0.027 g (49% yield) of 2-{4-[1-hydroxy-4-(4-{1-[2-(2-methoxy-ethoxy)-ethyl]-1H-indol-3-yl}-piperidin-1-yl)-butyl]-phenyl}-2-methyl-propionic acid.

ESI/MS m/e=537 [(M+1)$^+$, C32H44 N2 O5]

NMR (300 MHz, CDCl$_3$) d=1.58 (s, 6H), 1.70–1.95 (m, 2H), 2.20–2.61 (m, 8H), 2.70–2.85 (m, 2H), 2.90–3.07 (m, 2H), 3.36 (s, 3H), 3.40–3.56 (m, 4H), 3.78–3.82 (t, 2H), 4.27–4.30 (t, 2H), 4.55–4.62 (m, 1H), 7.01–7.41 (m, 8H), 7.61–7.63 (d, 1H)

EXAMPLE 34

Preparation of 2-(4-{1-hydroxy-4-[4-(1-pentyl-1H-indol-3-yl)-piperidin-1-yl]-butyl}-phenyl)-2-methyl-propionic acid The procedure described in Example 1 was performed using 0.2 g (1 mmol) of 3-piperidin-4-yl-1H-indole and 0.31 g (1.1 mmol) of 2-[4-(4-chloro-1-hydroxy-butyl)-phenyl]-2-methyl-propionic acid methyl ester. 0.05 g (0.1 mmol) of the crude, obtained as in step D, were then alkylated with 0.02 mL (0.15 mmol) of pentyl iodide affording 0.022 g (41% yield) of 2-(4-{1-hydroxy-4-[4-(1-pentyl-1H-indol-3-yl)-piperidin-1-yl]-butyl}-phenyl)-2-methyl-propionic acid.

ESI/MS m/e=505 [(M+1)$^+$, C32H44 N2 O3]

NMR (300 MHz, CDCl$_3$) d=0.86–0.92 (t, 3H), 1.27–1.36 (m, 4H), 1.57 (s, 6H), 2.05–2.60 (m, 9H), 2.89–3.10 (m, 7H), 3.55–3.80 (m, 2H), 4.00–4.06 (t, 2H), 2.75–2.85 (m, 1H), 6.97–7.32 (m, 8H), 7.59–7.61 (d, 1H)

EXAMPLE 35

Preparation of 2-[4-(4-{4-[1-(2-ethoxy-ethyl)-1H-indol-3-yl]-piperidin-1-yl}-1-hydroxy-butyl)-phenyl]-2-methyl-propionic acid The procedure described in Example 1 was performed using 0.2 g (1 mmol) of 3-piperidin-4-yl-1H-indole and 0.31 g (1.1 mmol) of 2-[4-(4-chloro-1-hydroxy-butyl)-phenyl]-2-methyl-propionic acid methyl ester. 0.05 g (0.1 mmol) of the crude, obtained as in step D, were then alkylated with 0.02 mL (0.15 mmol) of bromoethyl ethyl ether affording 0.046 g (91% yield) of 2-[4-(4-{4-[1-(2-ethoxy-ethyl)-1H-indol-3-yl]-piperidin-1-yl}-1-hydroxy-butyl)-phenyl]-2-methyl-propionic acid.

ESI/MS m/e=507 [(M+1)$^+$, C31H42 N2 O4]

NMR (300 MHz, CDCl$_3$) d=1.12–1.17 (t, 3H), 1.57 (s, 6H), 1.77–2.42 (m, 8H), 2.82–3.09 (m, 5H), 3.41–3.61 (m, 6H), 3.65–3.72 (t, 2H), 4.21–4.25 (t, 2H), 4.67–4.71 (m, 1H), 7.00–7.37 (m, 8H), 7.59–7.62 (d, 1H)

EXAMPLE 36

Preparation of [2-(4-{1-[2-(2-methoxy-ethoxy)-ethyl]-1H-indol-3-yl}-piperidin-1-yl)-ethoxy]-acetic acid The procedure described in Example 1 was performed using 0.2 g (1 mmol) of 3-piperidin-4-yl-1H-indole and 0.18 g (1.1 mmol) of (2-chloro-ethoxy)-acetic acid ethyl ester. 0.06 g (0.18 mmol) of the crude, obtained as in step D, were then alkylated with 0.03 mL (0.27 mmol) of 1-bromo-2-(2-methoxy-ethoxy)-ethane affording 0.056 g (77% yield) of [2-(4-{1-[2-(2-methoxy-ethoxy)-ethyl]-1H-indol-3-yl}-piperidin-1-yl)-ethoxy]-acetic acid.

ESI/MS m/e=405 [(M+1)$^+$, C22H32 N2 O5]

NMR (300 MHz, CDCl$_3$) d=2.05–2.40 (m, 4H), 2.89–3.05 (m, 5H), 3.36 (s, 3H), 3.47–3.57 (m, 4H), 3.67–3.81 (m, 4H), 3.87–3.91 (t, 2H), 4.10 (s, 2H), 4.24–4.28 (t, 2H), 7.02–7.27 (m, 3H), 7.35–7.37 (d, 1H), 7.56–7.58 (d, 1H)

EXAMPLE 37

Preparation of (2-{4-[1-(4-fluoro-benzyl)-1H-indol-3-yl]-piperidin-1-yl}-ethoxy)-acetic acid The procedure described in Example 1 was performed using 0.2 g (1 mmol) of 3-piperidin-4-yl-1H-indole and 0.18 g (1.1 mmol) of (2-chloro-ethoxy)-acetic acid ethyl ester. 0.06 g (0.18 mmol) of the crude, obtained as in step D, were then alkylated with 0.03 mL (0.27 mmol) of 4-fluorobenzyl bromide affording 0.059 g (80% yield) of (2-{4-[1-(4-fluoro-benzyl)-1H-indol-3-yl]-piperidin-1-yl}-ethoxy)-acetic acid.

ESI/MS m/e=411 [(M+1)$^+$, C24H27 F N2 O3]

NMR (300 MHz, CDCl$_3$) d=2.25–2.40 (m, 4H), 2.96–3.10 (m, 5H), 3.58–3.63 (m, 2H), 3.87–3.91 (t, 2H), 4.07 (s, 2H), 5.24 (s, 2H), 6.97–7.28 (m, 8H), 7.57–7.60 (d, 1H)

EXAMPLE 38

Preparation of {2-[4-(1-pentyl-1H-indol-3-yl)-piperidin-1-yl]-ethoxy}-acetic acid The procedure described in Example 1 was performed using 0.2 g (1 mmol) of 3-piperidin-4-yl-1H-indole and 0.18 g (1.1 mmol) of (2-chloro-ethoxy)-acetic acid ethyl ester. 0.06 g (0.18 mmol) of the crude, obtained as in step D, were then alkylated with 0.03 mL (0.27 mmol) of pentyl iodide affording 0.047 g (74% yield) of {2-[4-(1-pentyl-1H-indol-3-yl)-piperidin-1-yl]-ethoxy}-acetic acid.

ESI/MS m/e=373 [(M+1)$^+$, C22H32 N2 O3]

NMR (300 MHz, CDCl$_3$) d=0.87–0.91 (t, 3H), 1.28–1.36 (m, 4H), 1.79–1.84 (m, 2H), 2.21–2.32 (m, 4H), 2.89–2.96 (m, 2H), 3.04–3.07 (m, 3H), 3.55–3.59 (d, 2H), 3.88–3.92 (t, 2H), 4.02–4.07 (t, 2H), 4.11 (s, 2H), 4.40–4.80 (bs, 1H), 6.97–7.34 (m, 4H), 7.56–7.58 (d, 1H)

EXAMPLE 39

Preparation of (2-{4-[1-(2-ethoxy-ethyl)-1H-indol-3-yl]-piperidin-1-yl}-ethoxy)-acetic acid The procedure described in Example 1 was performed using 0.2 g (1 mmol) of 3-piperidin-4-yl-1-H-indole and 0.18 g (1.1 mmol) of (2-chloro-ethoxy)-acetic acid ethyl ester. 0.06 g (0.18 mmol) of the crude, obtained as in step D, were then alkylated with 0.03 mL (0.27 mmol) of bromoethyl ethyl ether affording 0.049 g (76% yield) of (2-{4-[1-(2-ethoxy-ethyl)-1H-indol-3-yl]-piperidin-1-yl}-ethoxy)-acetic acid.

ESI/MS m/e=375 [(M+1)$^+$, C21H30 N2 O4]

NMR (300 MHz, CDCl$_3$) d=1.13–1.18 (t, 3H), 2.20–2.40 (4H), 2.80–3.08 (m, 5H), 3.43–3.57 (m, 4H), 3.72–3.76 (t, 2H), 3.87–3.91 (t, 2H), 4.08 (s, 2H), 4.23–4.27 (t, 2H), 7.06–7.28 (m, 3H), 7.36–7.39 (d, 1H), 7.55–7.58 (d, 1H)

EXAMPLE 40

Preparation of 5-(4-{1-[2-(2-methoxy-ethoxy)-ethyl]-1H-indol-3-yl}-piperidin-1-yl-methyl)-furan-2-carboxylic acid The procedure described in Example 1 was performed using 0.2 g (1 mmol) of 3-piperidin-4-yl-1H-indole and 0.19 g (1.1 mmol) of 5-bromo-methyl-furan-2-carboxylic acid ethyl ester. 0.08 g (0.22 mmol) of the crude, obtained as in step D, were then alkylated with 0.04 mL (0.33 mmol) of 1-bromo-2-(2-methoxy-ethoxy)-ethane affording 0.034 g (36% yield) of 5-(4-{1-[2-(2-methoxy-ethoxy)-ethyl]-1H-indol-3-yl}-piperidin-1-yl-methyl)-furan-2-carboxylic acid.

Melting point=159° C.

ESI/MS m/e=427 [(M+1)+, C24H30 N2 O5]

NMR (300 MHz, CDCl3) d=2.05–2.90 (m, 9H), 3.32 (s, 3H), 3.39–3.48 (m, 4H), 3.67–3.75 (m, 2H), 4.00–4.25 (m, 4H), 6.35–6.40 (m, 1H), 6.92–7.33 (m, 5H), 7.53–7.56 (d, 1H)

EXAMPLE 41

Preparation of 5-[4-(1-pentyl-1H-indol-3-yl)-piperidin-1-yl-methyl]-furan-2-carboxylic acid The procedure described in Example 1 was performed using 0.2 g (1 mmol) of 3-piperidin-4-yl-1H-indole and 0.19 g (1.1 mmol) of 5-bromo-methyl-furan-2-carboxylic acid ethyl ester. 0.08 g (0.22 mmol) of the crude obtained in step D were then alkylated with 0.04 mL (0.33 mmol) of pentyl iodide affording 0.064 g (70% yield) of 5-[4-(1-pentyl-1H-indol-3-yl)-piperidin-1-yl-methyl]-furan-2-carboxylic acid.

Melting point=163–165° C.

ESI/MS m/e=395 [(M+1)+, C24H30 N2 O3]

NMR (300 MHz, CDCl3) d=0.79–0.84 (t, 3H), 1.20–2.29 (m, 12H), 2.50–2.70 (m, 1H), 2.89–2.96 (m, 2H), 3.36–3.49 (m, 2H), 3.80–4.00 (m, 2H), 5.80–6.00 (m, 1H), 6.70–7.23 (m, 5H), 7.50–7.53 (d, 1H)

EXAMPLE 42

Preparation of 5-{4-[1-(2-ethoxy-ethyl)-1H-indol-3-yl]-piperidin-1-yl-methyl}-furan-2-carboxylic acid The procedure described in Example 1 was performed using 0.2 g (1 mmol) of 3-piperidin-4-yl-1H-indole and 0.19 g (1.1 mmol) of 5-bromo-methyl-furan-2-carboxylic acid ethyl ester. 0.08 g (0.22 mmol) of the crude, obtained as in step D, were then alkylated with 0.04 mL (0.33 mmol) of bromoethyl ethyl ether affording 0.069 g (75% yield) of 5-{4-[1-(2-ethoxy-ethyl)-1H-indol-3-yl]-piperidin-1-yl-methyl}-furan-2-carboxylic acid.

ESI/MS m/e=397 [(M+1)+, C23H28 N2 O4]

NMR (300 MHz, CDCl3) d=1.05–2.00 (t, 3H), 1.80–3.10 (m, 9H), 3.32–3–34 (d, 2H), 3.50–3.80 (m, 4H), 4.00–4.20 (m, 2H), 6.00–6.20 (m, 1H), 6.81–7.20 (m, 5H), 7.50–7.53 (d, 1H)

EXAMPLE 43

Preparation of 5-{4-[1-(4-fluorobenzyl)-1H-indol-3-yl]-piperidin-1-ylmethyl}-furan-2-carboxylic acid.

The procedure described in Example 1 was performed using 0.2 g (1 mmol) of 3-piperidin-4-yl-1H-indole and 0.19 g (1.1 mmol) of 5-bromomethyl-furan-2-carboxylic acid ethyl ester. 0.08 g (0.22 mmol) of the crude, obtained as in step D, were then alkylated with 0.04 mL (0.33 mmol) of 4-fluorobenzyl bromide affording 0.031 g (32% yield) of 5-{4-[1-(4-fluorobenzyl)-1H-indol-3-yl]-piperidin-1-ylmethyl}-furan-2-carboxylic acid.

ESI/MS m/e=433 [(M+1)+, C26H25 F N2 O3]

NMR (300 MHz, DMSO) d=1.65–1.72 (m, 2H), 1.92–1.96 (m, 2H), 2.16–2.23 (t, 2H), 2.60–2.80 (m, 1H), 2.92–2.96 (m, 2H), 3.45 (s, 2H), 5.33 (s, 2H), 6.49–6.50 (d, 1H), 6.95–7.27 (m, 8H), 7.38–7.41 (d, 1H), 7.55–7.58 (d, 1H)

EXAMPLES 44–133

The following compounds were synthesized applying the general procedure described in Example 1 using the corresponding reactants. The ESI/MS data and yields are summarized in table 2.

TABLE 2

| Example | ESI/MS m/e [(M + 1+] | Molecular Formula | Yield (%) |
|---|---|---|---|
| 44 | 2-[4-(4-{4-[1-(4-fluoro-benzyl)-1H-indol-3-yl]-piperidin-1-yl}-1-hydroxy-butyl)-phenyl]-2-methyl-propionic acid | | |
| | 543 | C34 H39 F N2 O3 | 46 |
| 45 | 2-{2-[4-(1-heptyl-1H-indol-3-yl)-piperidin-1-yl]-ethoxy}-benzoic acid | | |
| | 463 | C29 H38 N2 O3 | 52 |
| 46 | 2-(2-{4-[1-(4-tert-butyl-benzyl)-1H-indol-3-yl]-piperidin-1-yl}-ethoxy)-benzoic acid | | |
| | 511 | C33 H38 N2 O3 | 44 |
| 47 | 2-(2-{4-[1-(4-methoxy-benzyl)-1H-indol-3-yl]-piperidin-1-yl}-ethoxy)-benzoic acid | | |
| | 485 | C30 H32 N2 O4 | 48 |
| 48 | 2-(2-{4-[1-(4-benzyloxy-benzyl)-1H-indol-3-yl]-piperidin-1-yl}-ethoxy)-benzoic acid | | |
| | 561 | C36 H36 N2 O4 | 61 |
| 49 | 2-{2-[4-(1-iso-butyl-1H-indol-3-yl)-piperidin-1-yl]-ethoxy}-benzoic acid | | |
| | 421 | C26 H32 N2 O4 | 38 |
| 50 | 2-[2-(4-{1-[2-(4-methoxy-phenyl)-ethyl]-1H-indol-3-yl}-piperidin-1-yl)-ethoxy]-benzoic acid | | |
| | 499 | C31 H34 N2 O4 | 58 |
| 51 | 2-(4-{2-[4-(1H-indol-3-yl)-piperidin-1-yl]-ethyl}-phenyl)-2-methyl-propionic acid | | |
| | 391 | C25 H30 N2 O2 | 70 |
| 52 | 2-(4-{4-[4-(1H-indol-3-yl)-piperidin-1-yl]-butyryl}-phenyl)-2-methyl-propionic acid | | |
| | 433 | C27 H32 N2 O3 | 67 |
| 53 | 2-[4-(1H-indol-3-yl)-piperidin-1-ylmethyl]-benzoic acid | | |
| | 335 | C21 H22 N2 O2 | 58 |
| 54 | 3-[4-(1H-indol-3-yl)-piperidin-1-ylmethyl]-benzoic acid | | |
| | 335 | C21 H22 N2 O2 | 85 |
| 55 | 4-[4-(1H-indol-3-yl)-piperidin-1-ylmethyl]-benzoic acid | | |
| | 335 | C21 H22 N2 O2 | 74 |
| 56 | (3-{2-[4-(1H-indol-3-yl)-piperidin-1-yl]-ethoxy}-phenyl)-acetic acid | | |
| | 379 | C23 H26 N2 O3 | 35 |
| 57 | (3-{3-[4-(1H-indol-3-yl)-piperidin-1-yl]-propoxy}-phenyl)-acetic acid | | |
| | 393 | C24 H28 N2 O3 | 29 |
| 58 | (4-{2-[4-(1H-indol-3-yl)-piperidin-1-yl]-ethoxy}-phenyl)-acetic acid | | |
| | 379 | C23 H26 N2 O3 | 31 |
| 59 | (4-{3-[4-(1H-indol-3-yl)-piperidin-1-yl]-propoxy}-phenyl)-acetic acid | | |
| | 393 | C24 H28 N2 O3 | 52 |
| 60 | 3-(1-{3-[3-(1H-tetrazol-5-yl)-phenoxyl-propyl}-piperidin-4-yl)-1H-indole | | |
| | 403 | C23 H26 N6 O | 66 |
| 61 | 2-methyl-2-[4-(2-{4-[1-(3-methyl-butyl)-1H-indol-3-yl]-piperidin-1-yl}-ethyl)-phenyl]-propionic acid | | |
| | 461 | C30 H40 N2 O2 | 14 |
| 62 | 2-[4-(2-{4-[1-(2-ethoxy-ethyl)-1H-indol-3-yl]-piperidin-1-yl}-ethyl)-phenyl]-2-methyl-propionic acid | | |
| | 463 | C29 H38 N2 O3 | 49 |
| 63 | 2-methyl-2-[4-(4-{4-[1-(3-methyl-butyl)-1H-indol-3-yl]-piperidin-1-yl}-butyryl)-phenyl]-propionic acid | | |
| | 503 | C32 H43 N2 O3 | 35 |

TABLE 2-continued

| Example | ESI/MS m/e [(M + 1⁺] | Molecular Formula | Yield (%) |
|---|---|---|---|
| 64 | 2-{4-[1-(3-methyl-butyl)-1H-indol-3-yl]-piperidin-1-ylmethyl}-benzoic acid 405 | C26 H32 N2 O2 | 68 |
| 65 | 2-{4-[1-(2-ethoxy-ethyl)-1H-indol-3-yl]-piperidin-1-ylmethyl}-benzoic acid 407 | C25 H30 N2 O3 | 22 |
| 66 | 3-{4-[1-(2-ethoxy-ethyl)-1H-indol-3-yl]-piperidin-1-ylmethyl}-benzoic acid 407 | C25 H30 N2 O3 | 27 |
| 67 | 4-{4-[1-(3-methyl-butyl)-1H-indol-3-yl]-piperidin-1-ylmethyl}-benzoic acid 405 | C26 H32 N2 O2 | 38 |
| 68 | [3-(2-{4-[1-(3-methyl-butyl)-1H-indol-3-yl]-piperidin-1-yl}-ethoxy)-phenyl]-acetic acid 449 | C28 H36 N2 O3 | 36 |
| 69 | [3-(2-{4-[1-(2-ethoxy-ethyl)-1H-indol-3-yl]-piperidin-1-yl}-ethoxy)-phenyl]-acetic acid 451 | C27 H34 N2 O4 | 41 |
| 70 | [3-(3-{4-[1-(3-methyl-butyl)-1H-indol-3-yl]-piperidin-1-yl}-propoxy)-phenyl]-acetic acid 463 | C29 H38 N2 O3 | 35 |
| 71 | [3-(3-{4-[1-(2-ethoxy-ethyl)-1H-indol-3-yl]-piperidin-1-yl}-propoxy)-phenyl]-acetic acid 465 | C28 H36 N2 O4 | 70 |
| 72 | [4-(2-{4-[1-(3-methyl-butyl)-1H-indol-3-yl]-piperidin-1-yl}-ethoxy)-phenyl]-acetic acid 449 | C28 H36 N2 O3 | 25 |
| 73 | [4-(2-{4-[1-(2-ethoxy-ethyl)-1H-indol-3-yl]-piperidin-1-yl}-ethoxy)-phenyl]-acetic acid 451 | C27 H34 N2 O4 | 45 |
| 74 | [4-(3-{4-[1-(3-methyl-butyl)-1H-indol-3-yl]-piperidin-1-yl}-propoxy)-phenyl]-acetic acid 463 | C29 H38 N2 O3 | 19 |
| 75 | [4-(3-{4-[1-(2-ethoxy-ethyl)-1H-indol-3-yl]-piperidin-1-yl}-propoxy)-phenyl]-acetic acid 465 | C28 H36 N2 O4 | 46 |
| 76 | 2-{2-[4-(1-prop-2-ynyl-1H-indol-3-yl)-piperidin-1-yl]-ethoxy}-benzoic acid 403 | C25 H26 N2 O3 | 20 |
| 77 | 2-methyl-2-[4-(4-{4-[1-(3-methyl-butyl)-1H-indol-3-yl]-piperidin-1-yl}-butyryl)-phenyl]-propionic acid 503 | C32 H42 N2 O3 | 52 |
| 78 | 1-(2-ethoxy-ethyl)-3-(1-{3-[2-(2H-tetrazol-5-yl)-phenoxy]-propyl}-piperidin-4-yl)-1H-indole 475 | C27 H34 N6 O2 | 38 |
| 79 | 1-(3-methyl-butyl)-3-(1-{3-[2-(2H-tetrazol-5-yl)-phenoxy]-propyl}-piperidin-4-yl)-1H-indole 473 | C28 H36 N6 O | 40 |
| 80 | 1-(3-methyl-butyl)-3-(1-{3-[4-(2H-tetrazol-5-yl)-phenoxy]-propyl}-piperidin-4-yl)-1H-indole 473 | C28 H36 N6 O | 21 |
| 81 | 2-(2-{4-[1-(2-ethoxy-ethyl)-5-methoxy-1H-indol-3-yl]-piperidin-1-yl}-ethoxy)-6-fluoro-benzoic acid 485 | C27 H33 F N2 O5 | 25 |
| 82 | 2-(2-{4-[1-(2-ethoxy-ethyl)-5-fluoro-1H-indol-3-yl]-piperidin-1-yl}-ethoxy)-6-fluoro-benzoic acid 473 | C26 H30 F2 N2 O4 | 33 |
| 83 | 2-(2-{4-[1-(2-ethoxy-ethyl)-6-fluoro-1H-indol-3-yl]-piperidin-1-yl}-ethoxy)-6-fluoro-benzoic acid 473 | C26 H30 F2 N2 O4 | 33 |
| 84 | 2-(2-{4-[5-bromo-1-(2-ethoxy-ethyl)-1H-indol-3-yl]-piperidin-1-yl}-ethoxy)-6-fluoro-benzoic acid 534 | C26 H30 Br F N2 O4 | 40 |
| 85 | 2-(2-{4-[7-bromo-1-(2-ethoxy-ethyl)-1H-indol-3-yl]-piperidin-1-yl}-ethoxy)-6-fluoro-benzoic acid 534 | C26 H30 Br F N2 O4 | 40 |
| 86 | 2-(2-{4-[5-chloro-1-(2-ethoxy-ethyl)-1H-indol-3-yl]-piperidin-1-yl}-ethoxy)-6-fluoro-benzoic acid 489 | C26 H30 Cl F N2 O4 | 51 |
| 87 | 2-(2-{4-[1-(2-ethoxy-ethyl)-1H-indol-3-yl]-piperidin-1-yl}-ethoxy)-6-fluoro-benzoic acid 455 | C26 H31 F N2 O4 | 22 |
| 88 | 3,5-dibromo-2-(2-{4-[1-(2-ethoxy-ethyl)-5-methoxy-1H-indol-3-yl]-piperidin-1-yl}-ethoxy)-benzoic acid 625 | C27 H32 Br2 N2 O4 | 25 |
| 89 | 3,5-dibromo-2-(2-{4-[1-(2-ethoxy-ethyl)-5-fluoro-1H-indol-3-yl]-piperidin-1-yl}-ethoxy)-benzoic acid 613 | C26 H29 Br2 F N2 O4 | 33 |
| 90 | 3,5-dibromo-2-(2-{4-[1-(2-ethoxy-ethyl)-6-fluoro-1H-indol-3-yl]-piperidin-1-yl}-ethoxy)-benzoic acid 613 | C26 H29 Br2 F N2 O4 | 36 |
| 91 | 3,5-dibromo-2-(2-{4-[5-bromo-1-(2-ethoxy-ethyl)-1H-indol-3-yl]-piperidin-1-yl}-ethoxy)-benzoic acid 674 | C26 H29 Br3 N2 O4 | 23 |
| 92 | 3,5-dibromo-2-(2-{4-[7-bromo-1-(2-ethoxy-ethyl)-1H-indol-3-yl]-piperidin-1-yl}-ethoxy)-benzoic acid 674 | C26 H29 Br3 N2 O4 | 25 |
| 93 | 3,5-dibromo-2-(2-{4-[1-(2-ethoxy-ethyl)-1H-indol-3-yl]-piperidin-1-yl}-ethoxy)-benzoic acid 595 | C26 H30 Br2 N2 O4 | 25 |
| 94 | 2-(2-{4-[1-(2-ethoxy-ethyl)-6-fluoro-1H-indol-3-yl]-piperidin-1-yl}-ethoxy)-5-methyl-benzoic acid 469 | C27 H33 F N2 O4 | 33 |
| 95 | 2-(2-{4-[5-chloro-1-(2-ethoxy-ethyl)-1H-indol-3-yl]-piperidin-1-yl}-ethoxy)-5-methyl-benzoic acid 486 | C27 H33 Cl N2 O4 | 47 |
| 96 | 2-(2-{4-[1-(2-ethoxy-ethyl)-5-methoxy-1H-indol-3-yl]-piperidin-1-yl}-ethoxy)-4-methoxy-benzoic acid 498 | C28 H36 N2 O4 | 63 |
| 97 | 2-(2-{4-[1-(2-ethoxy-ethyl)-6-fluoro-1H-indol-3-yl]-piperidin-1-yl}-ethoxy)-4-methoxy-benzoic acid 485 | C27 H33 F N2 O5 | 46 |
| 98 | 2-(2-{4-[5-bromo-1-(2-ethoxy-ethyl)-1H-indol-3-yl]-piperidin-1-yl}-ethoxy)-4-methoxy-benzoic acid 546 | C27 H33 Br N2 O5 | 24 |
| 99 | 2-(2-{4-[7-bromo-1-(2-ethoxy-ethyl)-1H-indol-3-yl]-piperidin-1-yl}-ethoxy)-4-methoxy-benzoic acid 546 | C27 H33 Br N2 O5 | 71 |
| 100 | 2-(2-{4-[5-chloro-1-(2-ethoxy-ethyl)-1H-indol-3-yl]-piperidin-1-yl}-ethoxy)-4-methoxy-benzoic acid 502 | C27 H33 Cl N2 O5 | 24 |
| 101 | 2-(2-{4-[1-(2-ethoxy-ethyl)-5-methoxy-1H-indol-3-yl]-piperidin-1-yl}-ethoxy)-benzoic acid 467 | C27 H34 N2 O5 | 33 |
| 102 | 2-(2-{4-[1-(2-ethoxy-ethyl)-5-fluoro-1H-indol-3-yl]-piperidin-1-yl}-ethoxy)-benzoic acid 455 | C26 H31 F N2 O4 | 28 |
| 103 | 2-(2-{4-[1-(2-ethoxy-ethyl)-6-fluoro-1H-indol-3-yl]-piperidin-1-yl}-ethoxy)-benzoic acid 455 | C26 H31 F N2 O4 | 56 |
| 104 | 2-(2-{4-[5-bromo-1-(2-ethoxy-ethyl)-1H-indol-3-yl]-piperidin-1-yl}-ethoxy)-benzoic acid 516 | C26 H31 Br N2 O4 | 25 |
| 105 | 2-(2-{4-[5-bromo-1-(2-ethoxy-ethyl)-1H-indol-3-yl]-piperidin-1-yl}-ethoxy)-5-methyl-benzoic acid 530 | C27 H33 Br N2 O4 | 47 |
| 106 | 2-(2-{4-[5-chloro-1-(2-ethoxy-ethyl)-1H-indol-3-yl]-piperidin-1-yl}-ethoxy)-benzoic acid 471 | C26 H31 Cl N2 O4 | 28 |
| 107 | 2-{2-[4-(1-propyl-1H-indol-3-yl)-piperidin-1-yl]-ethoxy}-benzoic acid | | |

TABLE 2-continued

| Example | ESI/MS m/e [(M + 1⁺] | Molecular Formula | Yield (%) |
|---|---|---|---|
| 108 | 407<br>2-(2-{4-[1-(2-iso-propoxy-ethyl)-1H-indol-3-yl]-piperidin-1-yl}-ethoxy)-benzoic acid | C25 H30 N2 O3 | 22 |
| 109 | 451<br>2-(2-{4-[1-(3-methoxy-propyl)-1H-indol-3-yl]-piperidin-1-yl}-ethoxy)-benzoic acid | C27 H34 N2 O4 | 32 |
| 110 | 437<br>2-(2-{4-[1-(2-ethoxy-ethyl)-4-fluoro-1H-indol-3-yl]-piperidin-1-yl}-ethoxy)-benzoic acid | C26 H32 N2 O4 | 37 |
| 111 | 455<br>2-(2-{4-[1-(2-ethoxy-ethyl)-4-fluoro-1H-indol-3-yl]-piperidin-1-yl}-ethoxy)-5-methyl-benzoic acid | C26 H31 F N2 O4 | 24 |
| | 469 | C27 H33 F N2 O4 | 22 |
| 112 | 2-(2-{4-[1-(2-ethoxy-ethyl)-4-fluoro-1H-indol-3-yl]-piperidin-1-yl}-ethoxy)-4-methoxy-benzoic acid<br>485 | C27 H33 F N2 O5 | 20 |
| 113 | 2-(2-{4-[4-fluoro-1-(2-methoxy-ethyl)-1H-indol-3-yl]-piperidin-1-yl}-ethoxy)-benzoic acid<br>441 | C25 H29 F N2 O4 | 25 |
| 114 | 2-(2-{4-[4-fluoro-1-(2-methoxy-ethyl)-1H-indol-3-yl]-piperidin-1-yl}-ethoxy)-5-methyl-benzoic acid<br>455 | C26 H31 F N2 O5 | 25 |
| 115 | 2-(2-{4-[4-fluoro-1-(2-methoxy-ethyl)-1H-indol-3-yl]-piperidin-1-yl}-ethoxy)-4-methoxy-benzoic acid<br>471 | C26 H31 F N2 O5 | 32 |
| 116 | 5-{4-[1-(2-ethoxy-ethyl)-1H-indol-3-yl]-piperidin-1-yl}-pentanoic acid<br>373 | C22 H32 N2 O3 | 41 |
| 117 | 6-{4-[1-(2-ethoxy-ethyl)-1H-indol-3-yl]-piperidin-1-yl}-hexanoic acid<br>387 | C23 H34 N2 O3 | 46 |
| 118 | 7-{4-[1-(2-ethoxy-ethyl)-1H-indol-3-yl]-piperidin-1-yl}-heptanoic acid<br>401 | C24 H36 N2 O3 | 41 |
| 119 | 3-(3-{4-[1-(2-ethoxy-ethyl)-1H-indol-3-yl]-piperidin-1-yl}-propoxy)-propionic acid<br>403 | C23 H34 N2 O4 | 46 |
| 120 | 2-(2-{4-[1-(2-ethoxy-ethyl)-7-methyl-1H-indol-3-yl]-piperidin-1-yl}-ethoxy)-5-methyl-benzoic acid<br>465 | C27 H34 N2 O4 | 55 |
| 121 | 2-(2-{4-[6-bromo-1-(2-ethoxy-ethyl)-1H-indol-3-yl]-piperidin-1-yl}-ethoxy)-benzoic acid<br>516 | C26 H31 Br N2 O4 | 34 |
| 122 | 2-(2-{4-[6-bromo-1-(2-ethoxy-ethyl)-1H-indol-3-yl]-piperidin-1-yl}-ethoxy)-5-methyl-benzoic acid<br>530 | C27 H33 Br N2 O4 | 29 |
| 123 | (2-{4-[1-(2-ethoxy-ethyl)-1H-indol-3-yl]-piperidin-1-yl}-ethylsulfanyl)-acetic acid<br>391 | C21 H30 N2 O3 S | 72 |
| 124 | (4-{4-[1-(2-ethoxy-ethyl)-1H-indol-3-yl]-piperidin-1-yl}-butylsulfanyl)-acetic acid<br>419 | C23 H34 N2 O3 S | 68 |
| 125 | (3-{3-[4-(1-cyclopropylmethyl-1H-indol-3-yl)-piperidin-1-yl]-propoxy}-phenyl)-acetic acid<br>447 | C28 H34 N2 O3 | 49 |
| 126 | (4-{2-[4-(1-cyclopropylmethyl-1H-indol-3-yl)-piperidin-1-yl]-ethoxy}-phenyl)-acetic acid<br>433 | C27 H32 N2 O3 | 36 |
| 127 | (3-{2-[4-(1-cyclopropylmethyl-1H-indol-3-yl)-piperidin-1-yl]-ethoxy}-phenyl)-acetic acid<br>433 | C27 H32 N2 O3 | 43 |
| 128 | 3-[4-(1-pentyl-1H-indol-3-yl)-piperidin-1-yl methyl]-benzoic acid<br>405 | C26 H32 N2 O2 | 35 |
| 129 | 5-[4-(6-fluoro-1-pentyl-1H-indol-3-yl)-piperidin-1-ylmethyl]-furan-2-carboxylic acid<br>413 | C24 H29 F N2 O3 | 141 |
| 130 | 3-[4-(6-fluoro-1-pentyl-1H-indol-3-yl)-piperidin-1-ylmethyl]-benzoic acid<br>423 | C26 H31 F N2 O2 | 44 |
| 131 | 2-(4-{4-[4-(1-cyclopropylmethyl-1H-indol-3-yl)-piperidin-1-yl]-butyryl}-phenyl)-2-methyl-propionic acid<br>487 | C31 H38 N2 O3 | 38 |
| 132 | 3-{3-[4-(1-cyclopropylmethyl-1H-indol-3-yl)-piperidin-1-yl]-propoxy}-benzoic acid<br>433 | C27 H32 N2 O3 | 45 |
| 133 | 2-{2-[4-(1-cyclohexylmethyl-1H-indol-3-yl)-piperidin-1-yl]ethoxy}-benzoic acid<br>461 | C29 H36 N2 O3 | 43 |

EXAMPLE 134

Preparation of 2-(2-{4-[1-(2-allyloxy-ethyl)-1H-indol-3-yl]-piperidin-1-yl}-ethoxy)-benzoic acid A. Preparation of 2-[2-(4-{1-[2-(tetrahydro-pyran-2-yloxy)-ethyl]-1H-indol-3-yl}-piperidin-1-yl)-ethoxyl-benzoic acid methyl ester To a suspension of 0.29 g (7 mmol) of a dispersion of 60% NaH in 10 mL of anhydrous DMF under inert atmosphere, a solution of 1.5 g (4 mmol) of 2-{2-[4-(1H-indol-3-yl)-piperidin-1-yl]-ethoxy}-benzoic acid methyl ester, prepared in Example 1 (part D), in 5 mL of DMF was added. After 30 minutes at room temperature, a solution of 1.09 g (5.2 mmol) of 2-(2-bromoethoxy)tetrahydro-2H-piran in 2 mL of DMF was added. The reaction mixture was stirred at room temperature for 15 hours. The solvent was removed under reduced pressure and the crude mixture was extracted between water and ethyl acetate. The organic phase was separated, dried and after filtering, the solvent was removed under reduced pressure. The crude mixture was purified by flash chromatography over silica affording 1.3 g (65% of yield) of the desired product.

MS=507 [(M+1)⁺, C30H38N2O5]

B. Preparation of 2-(2-{4-[1-(2-hydroxy-ethyl)-1H-indol-3-yl]-piperidin-1-yl}-ethoxy)-benzoic acid To a solution of 0.7 g (1.4 mmol) of 2-[2-(4-{1-[2-(tetrahydro-pyran-2-yloxy)-ethyl]-1H-indol-3-yl}-piperidin-1-yl)-ethoxy]-benzoic acid methyl ester in 10 mL of methyl alcohol, 10 mL of a solution of methyl alcohol saturated with hydrogen chloride were added. The crude mixture was heated at 70° C. for 1 hour and the solvent was removed under reduced pressure. After addition of 20 mL of water, the crude mixture was neutralised with 2N NaOH and the aqueous phase was extracted with chloroform. After removal of the solvent at reduced pressure 0.5 g of the desired product were obtained.

MS=423 [(M+1)⁺, C25H30N2O4]

C. Preparation of 2-(2-{4-[1-(2-allyloxy-ethyl)-1H-indol-3-yl]-piperidin-1-yl}-ethoxy)-benzoic acid To a suspension of 0.012 g (0.04 mmol) of a dispersion of 60% NaH in 0.5 mL of DMF, a solution of 0.042 g (0.01 mmol)of 2-(2-{4-[1-(2-hydroxy-ethyl)-1H-indol-3-yl]-piperidin-1-yl}-ethoxy)-benzoic acid in 0.5 mL of DMF was added. After stirring at room temperature for 30 minutes as solution of 0.014 g (0.12 mmol) of allyl bromide in 0.3 mL of DMF was added. The crude mixture was stirred at room temperature for 15 hours. The solvent was evaporated at reduced pressure and the crude mixture was dissolved in 1 mL of ethanol. 0.2 mL of an aqueous 2N NaOH solution were added and the mixture was heated at 60° C. for 3 hours. The solvent was removed under reduced pressure and after addition of 1 mL of water, the mixture was neutralised with 2N HCl and extracted with chloroform. The crude was purified by chromatography over silica gel affording 0.015 g (33% of yield) of the desired product.

MS=449 [(M+1)$^+$, C27H32 N2 O4]

RMN (CDCl$_3$) d=2.01–2.05 (m, 4H), 2.35–2.62 (m, 2H), 2.83–2.89 (m, 3H), 3.13–3.19 (d, 2H), 3.72–3.77 (t, 2H), 3.91–3.95 (t, 2H), 4.23–4.29 (t, 2H), 4.41–4.46 (t, 2H), 5.12–5.25 (m, 2H), 5.74–5.90 (m, 1H), 6.97–7.45 (m, 7H), 7.55–7.58 (d, 1H), 7.88–7.93 (dd, 1H)

EXAMPLES 135 AND 136

The compounds disclosed in Examples 135 and 136 were prepared following the procedure described in Example 134. The ESI/MS data and yields are summarised in table 3.

TABLE 3

| Example | ESI/MS m/e [(M + 1)$^+$] | Molecular Formula | Yield (%) |
|---|---|---|---|
| 135 | 2-(2-{4-[1-(2-prop-2-ynyloxy-ethyl)-1H-indol-3-yl]-piperidin-1-yl}-ethoxy)-benzoic acid 447 | C27 H30 N2 O4 | 44 |
| 136 | 2-(2-{4-[1-(2-propoxy-ethyl)-1H-indol-3-yl]-piperidin-1-yl}-ethoxy)-benzoic acid 451 | C27 H34 N2 O4 | 51 |

EXAMPLE 137

Preparation of 4-(2-{4-[1-(2-ethoxy-ethyl)-1H-indol-3-yl]piperidin-1-yl}-ethoxy)-benzoic acid A. Preparation of 4-(2-chloro-ethoxy)-benzoic acid tert-butyl ester A solution of 2 g (13.2 mmol) of 4-hydroxy-benzoic acid methyl ester in 30 mL of anhydrous DMF was added to a suspension of 0.68 g (17 mmol) of 60% NaH in 30 mL of anhydrous DMF at 0° C. under nitrogen atmosphere. After stirring for 40 minutes at room temperature, 2.2 mL (17 mmol) of benzyl bromide were added and stirred for two further hours. The reaction mixture was poured into water and extracted with ethyl acetate, the organic layer was dried over MgSO$_4$ and after filtering and removing the solvent under reduced pressure, the crude mixture was purified by column chromatography over silica gel affording 3.18 g (99% yield) of 4-benzyloxy-benzoic acid methyl ester.

16 mL of a 2N LiOH aqueous solution were added to a solution of 3.0 g (12.5 mmol) of 4-benzyloxy-benzoic acid methyl ester in 50 mL of THF and the mixture was refluxed overnight. The reaction mixture was acidified with HCl 6N and extracted with ethyl acetate affording after filtration and removal of the solvent under reduced atmosphere, 2.8 g (93% yield) of 4-benzyloxy-benzoic acid.

To a refluxing solution of 0.96 g (4.2 mmol) of 4-benzyloxy-benzoic acid in benzene 3.45 g (17 mmol) of di-tert-butoxymethyl-dimethyl-amino were slowly added during 20 minutes and the mixture was refluxed for 40 minutes. After cooling at room temperature the reaction mixture was poured into a saturated aqueous solution of NaHCO$_3$ and extracted with ethyl acetate. The organic layer was dried over MgSO$_4$ and after filtration and removal of the solvent under reduced pressure, the crude was purified by column chromatography of silica gel affording 1.2 g of 4-benzyloxy-benzoic acid tert-butyl ester.

0.36 g of 10% palladium on activated carbon were added to a solution of 1.2 g (4.3 mmol) of 4-benzyloxy-benzoic acid tert-butyl ester in 45 mL of ethanol and this mixture was hydrogenated at 20 psi for 3 hours. After filtering over celite and removing the solvent under reduced pressure 0.79 g (95% yield) of 4-hydroxy-benzoic acid tert-butyl ester were obtained.

A mixture containing 0.79 g (4.1 mmol) of 4-hydroxy-benzoic acid tert-butyl ester, 1.13 g (8.14 mmol) of K$_2$CO$_3$ and 1.6 mL (16.3 mmol) of 1-bromo-2-chloro-ethane in 10 mL of isobutyl methyl ketone was refluxed for 5 hours. After filtering, the solvent was removed under reduced pressure affording 0.98 g (94% yield) of 4-(2-chloro-ethoxy)-benzoic acid tert-butyl ester.

B. Preparation of 4-(2-{4-[1-(2-ethoxy-ethyl)-1H-indol-3-yl]-piperidin-1-yl}-ethoxy)-benzoic acid 4-(2-{4-[1-(2-ethoxy-ethyl)-1H-indol-3-yl]-piperidin-1-yl}-ethoxy)-benzoic acid was prepared using the general procedure described in Example 1 (part D), starting with 0.1 g (0.5 mmol) of 3-piperidin-4-yl-1H-indole, 0.26 g (0.5 mmol) of 4-(2-chloro-ethoxy)-benzoic acid tert-butyl ester, 0.08 g (0.6 mmol) of potassium carbonate and 0.04 g (0.2 mmol) of potassium iodide in 1.5 mL of isobutyl methyl ketone for the first alkylation step affording 0.09 g (44% yield) of 4-{2-[4-(1H-indol-3-yl)-piperidin-1-yl]-ethoxy}-benzoic acid.

0.05 g (0.11 mmol) of 4-{2-[4-(1H-indol-3-yl)-piperidin-1-yl]ethoxy}-benzoic acid was submited to N-indol alkylation using 0.028 g (0.68 mmol) of 60% NaH and 0.02 mL (0.15 mmol) of 2-bromoethoxy-ethyl in 1 mL of anhydrous DMF affording 0.06 g (100% yield) of 4-(2-{4-[1-(2-ethoxy-ethyl)-1H-indol-3-yl]piperidin-1-yl}-ethoxy)-benzoic acid.

MS=437 [(M+1)$^+$, C26H32 N2 O4]

NMR (CDCl$_3$) d=1.11–1.16 (t, 3H), 2.27–2.45 (m, 4H), 2.96–3.10 (m, 4H), 3.41–3.45 (m, 2H), 3.71–3.80 (m, 6H), 4.10–4.25 (m, 2H), 4.40–4.60 (m, 2H), 6.84–7.85 (m, 9H)

EXAMPLE 138

Preparation of 2-(2-{4-[1-(2-ethoxy-ethyl)-1H-indol-3-yl]piperidin-1-yl}-ethoxy)-benzoic acid A. Preparation of methyl 2-{2-[4-(1H-indol-3-yl)-piperidin-1-yl]-ethoxy}-benzoate 10 g (0.05 mol) of 4-(3-indolyl)-piperidine, 16.1 g (0.075 mol) of 2-(2-chloro-ethoxy)-benzoic acid methyl ester both prepared in Example 1 (parts A and B), 31.1 g (0.225 mol) of potassium carbonate and 1.33 g (0.008 mol) of potassium iodide were suspended in 90 ml of methyl isobutyl ketone. This mixture was refluxed for 24 h. Once the reaction was completed, the inorganic salts were filtered and the liquid phase evaporated to dryness. The remaining material was redissolved in dichloromethane and water and worked-up as usual. The crude mixture was purified by flash-chromatography over silica gel affording 9.58 g (51% of yield) of methyl 2-{2-[4-(1H-indol-3-yl)-piperidin-1-yl]-ethoxy}-benzoate.

Melting point=124–125° C.

B. Preparation of methyl 2-(2-{4-[1-(2-ethoxy-ethyl)-1H-indol-3-yl]-piperidin-1-yl}-ethoxy)-benzoate 8.0 g (0.021 mol) of methyl 2-{2-[4-(1H-indol-3-yl)-piperidin-1-yl]-ethoxy}-benzoate were dissolved in 125 ml of DMF and, at room temperature, 1.12 g (0.028 mol) of 60% sodium hydride was carefully added. This mixture was stirred for half an hour. 2.9 ml (0.023 mol) of 2-bromoethyl ethyl ether were dropwise added and the stirring was continued for 4 h. The solvent was evaporated under reduced pressure and the residue was worked-up as usual. The crude mixture was purified by flash-chromatography over silica gel affording 4.12 g (54% of yield) of methyl 2-(2-{4-[1-(2-ethoxy-ethyl)-1H-indol-3-yl]-piperidin-1-yl}-ethoxy)-benzoate C. Preparation of 2-(2-{4-[1-(2-ethoxy-ethyl)-1H-indol-3-yl]-piperidin-1-yl}-ethoxy)-benzoic acid 1.05 g (2.33 mmol) of 2-(2-{4-[1-(2-ethoxy-ethyl)-1H-indol-3-yl]-piperidin-1-yl}-ethoxy)-benzoate was dissolved in 30 ml of ethanol. A solution of 0.19 g (4.66 mmol) of sodium hydroxide in 30 ml of water was added to the previous one and the whole mixture was heated at 60° C. for 2 h. After dilution with water and neutralisation with HCl 6N, the aqueous phase was extracted three times with chloroform. The organic solution was washed with brine, dried with sodium sulphate, filtered and evaporated to dryness. The 4.06 g of crude material was recrystallised in acetonitrile affording 2.54 g (64% of yield)of 2-(2-{4-[1-(2-ethoxy-ethyl)-1H-indol-3-yl]-piperidin-1-yl}-ethoxy)-benzoic acid Melting point=147.6–148.9° C.
MS=437 [(M+1)$^+$, C26H32 N2 O4]
RMN (CDCl$_3$) d=1.05 (t, 3H), 1.9 (m, 5H), 2.6 (t, 1H), 2.9 m, 3H), 3.2 (m, 2H), 3.4 (q, 2H), 3.7 (t, 2H), 4.3 (t, 2H), 5.5 (m, 1H), 4.5 (m, 2H), 7.0–7.7 (m, 8H)

EXAMPLE 139

Preparation of 2-(2-{4-[1-(3-methyl-butyl)-1H-indol-3-yl]-piperidin-1-yl}-ethoxy)-benzoic acid This compound was prepared following the procedure described in Example 138 (part B) starting with 3 g (7.9 mmol) of methyl 2-{2-[4-(1H-indol-3-yl)-piperidin-1-yl]-ethoxy}-benzoate, 0.54 g (13.5 mmol) of NaH in 60% of mineral oil and 1.67 g (11.08 mmol) of 3-methylbutyl iodide. The crude mixture was hydrolised following the procedure described in Example 138 (part C) and purified by chromatography over silica gel affording 2.7 g (77% of yield) of the desired product. Melting point=150–151° C.

ESI/MS m/e=435 [(M+1)$^+$, C27H34 N2 O3]
NMR (300 MHz, DMSO) d=0.91–0.93 (d, 6H), 1.48–1.67 (m, 3H), 1.92–1.98 (m, 4H), 2.62–2.66 (m, 2H), 2.88–2.99 (m, 3H), 3.21–3.25 (d, 2H), 4.09–4.14 (t, 2H), 4.42–4.54 (t, 2H), 4.90–5.10 (bs, 1H), 6.96–7.14 (m, 4H), 7.21–7.24 (d, 2H), 7.36–7.39 (m, 2H), 7.53–7.56 (dd, 1H), 7.63–7.66 (d, 1H)

EXAMPLE 140

Preparation of 2-(2-{4-[1-(2-methoxy-ethyl)-1H-indol-3-yl]-piperidin-1-yl}-ethoxy)-benzoic acid This compound was prepared following the procedure described in Example 138 (part B) starting with 3 g (7.9 mmol) of methyl 2-{2-[4-(1H-indol-3-yl)-piperidin-1-yl]-ethoxy}-benzoate, 0.54 g (13.5 mmol) of NaH in 60% of mineral oil and 1.04 mL (11.08 mmol) of bromoethylmethyl ether. The crude mixture was hydrolised following the procedure described in Example 138 (part C) and purified by chromatography over silica gel affording 1.3 g (39% of yield) of the desired product.

Melting point=139–140° C.
ESI/MS m/e=423 [(M+1)$^+$, C25H30 N2 O4]
NMR (300 MHz, DMSO) d=1.91–1.98 (m, 4H), 2.61–2.69 (m, 2H), 2.91–2.99 (m, 3H), 3.62–3.65 (t, 2H), 4.25–4.29 (t, 2H), 4.42–4.45 (t, 2H), 5.20–6.00 (bs, 1H), 6.97–7.14 (m, 4H), 7.22–7.24 (d, 1H), 7.36–7.42 (m, 2H), 7.53–7.55 (d, 1H), 7.63–7.66 (d, 1H)

EXAMPLE 141

Preparation of 2-{2-[4-(1-allyl-1H-indol-3-yl)-piperidin-1-yl]-ethoxy}-benzoic acid This compound was prepared following the procedure described in Example 138 (part B) starting with 2.8 g (7.4 mmol) of methyl 2-{2-[4-(1H-indol-3-yl)-piperidin-1-yl]-ethoxy}-benzoate, 0.38 g (9.6 mmol) of NaH in 60% of mineral oil and 0.77 mL (8.9 mmol) of allyl bromide. The crude mixture was hydrolised following the procedure described in Example 138 (part C) and purified by chromatography over silica gel affording 0.62 g (23% of yield) of the desired product.

Melting point=123–125° C.
ESI/MS m/e=405 [(M+1)$^+$, C25H28 N2 O3]
NMR (300 MHz, CDCl$_3$) d=1.96–2.32 (m, 4H), 2.34–2.41 (m, 2H), 2.83–2.91 (m, 3H), 3.12–3.16 (d, 2H), 4.40–4.35 (t, 2H), 4.66–4.68 (m, 2H), 5.08–5.21 (m, 2H), 5.93–6.92 (m, 3H), 7.00 (S, 1H), 7.03–7.31 (m, 5H), 7.40–7.46 (t, 1H), 7.57–7.60 (d, 1H), 7.88–7.91 (dd, 1H)

EXAMPLE 142

Preparation of 2-(2-{4-[1-(2-ethoxy-ethyl)-5-methoxy-1H-indol-3-yl]-piperidin-1-yl}-ethoxy)-5-methyl-benzoic acid A. Preparation of 2-(2-chloro-ethoxy)-5-methyl-benzoic acid ethyl ester This compound was prepared following the procedure described in Example 1 (part C) starting with 5 g (27.8 mmol) of 2-hydroxy-5-methyl-benzoic acid ethyl ester, 7.9 mL (55.5 mmol) of 1-bromo-2-chloro-ethane and 7.7 g (55.5 mmol) of potassium carbonate. After the work-up and purification, 4.5 g (68% of yield) of the desired product was obtained.

NMR (300 MHz, CDCl$_3$) d=1.37–1.42 (t, 3H), 2.31 (s, 3H), 3.82–3.86 (t, 2H), 4.24–4.28 (t, 2H), 4.32–4.39 (q, 2H), 6.86–6.89 (d, 1H), 7.23–7.26 (m, 1H), 7.59–7.60 (d, 1H)

B. Preparation of 5-methoxy-3-piperidin-4-yl-1H-indole

This compound was prepared following the procedure described in Example 1 (parts A and B) starting with 5 g (33.9 mmol) of 5-methoxyindol and 13.2 g (86.2 mmol) of 4-piperidone monohydrate hydrochloride. After the usual work-up 6.5 g (83% of yield) of the desired product were obtained.

ESI/MS m/e=231 [(M+1)$^+$, C14H18 N2 O]

C. Preparation of 2-(2-{4-[1-(2-ethoxyethyl)-5-methoxy-1H-indol-3-yl]-piperidin-1-yl}-ethoxy)-5-methyl-benzoic acid This compound was prepared following the procedure described in Example 138 (part B) starting with 1.4 g (3.2 mmol) of 2-{2-[4-(5-methoxy-1H-indol-3-yl)-piperidin-1-yl]-ethoxy}-5-methyl-benzoic acid ethyl ester (prepared as in Example 138, part A), 0.17 g (4.2 mmol) of NaH in 60% of mineral oil and 0.43 mL (3.8 mmol) of bromoethylethyl ether. The crude mixture was hydrolised following the procedure described in Example 138 (part C) and purified by chromatography over silica gel affording 0.470 g (35% of yield) of the desired product.

Melting point=144–146° C.
ESI/MS m/e=481 [(M+1)$^+$, C28H36 N2 O5]
NMR (300 MHz, CDCl$_3$) d=1.02–1.07 (m, 3H), 1.90–2.05 (m, 4H), 2.10–2.25 (m, 3H), 2.50–2.65 (m, 2H), 2.80–3.05 (m, 3H), 3.20–3.23 (d, 2H), 3.36–3.39 (m, 2H), 3.50–3.64 (m, 2H), 3.80 (S, 3H), 4.10–4.25 (m, 2H), 4.30–4.45 (m, 2H), 6.73–6.76 (d, 1H), 7.09–7.15 (m, 4H), 7.31–7.35 (m, 2H)

EXAMPLE 143

Preparation of 2-(2-{4-[7-bromo-1-(2-ethoxy-ethyl)-1H-indol-3-yl]-piperidin-1-yl}-ethoxy)-5-methyl-benzoic acid A. Preparation of 7-bromo-3-piperidin-4-yl-1H-indole This compound was prepared following the procedure described in Example 1 (parts A and B) starting with 0.95 g (4.8 mmol) of 7-bromoindol and 1.89 g (12.3 mmol) of 4-piperidone monohydrate hydrochloride. After the usual work-up 1.1 g (89% of yield) of the desired product were obtained.

ESI/MS m/e=280 [(M+1)$^+$, C13H15 Br N2]

B. Preparation of 2-(2-{4-[7-bromo-1-(2-ethoxy-ethyl)-1H-indol-3-yl]-piperidin-1-yl}-ethoxy)-5-methyl-benzoic acid This compound was prepared following the procedure described in Example 138 (part B) starting with 1.6 g (3.3 mmol) of 2-{2-[4-(7-bromo-1H-indol-3-yl)-piperidin-1-yl]-ethoxy}-5-methyl-benzoic acid methyl ester (prepared as in Example 138, part A), 0.17 g (4.2 mmol) of NaH in 60% of mineral oil and 0.45 mL (4 mmol) of bromoethylethyl ether. The crude mixture was hydrolised following the procedure described in Example 138 (part C) and purified by chromatography over silica gel affording 0.26 g (34% of yield) of the desired product.

ESI/MS m/e=530 [(M+1)$^+$, C27H33 Br N2 O4]

NMR (300 MHz, CDCl$_3$) d=1.12–1.18 (t, 3H), 1.97–2.00 (m, 4H), 2.32 (s, 3H), 2.73–3.09 (m, 5H), 3.09–3.13 (d, 2H), 3.41–3.48 (q, 2H), 3.76–3.80 (t, 2H), 4.38–4.41 (t, 2H), 4.66–4.70 (t, 2H), 6.88–6.97 (m, 3H), 7.23–7.25 (m, 1H), 7.50–7.52 (d, 1H), 7.73–7.74 (d, 1H)

EXAMPLE 144

Preparation of 2-(2-{4-[7- bromo-1-(2-ethoxy-ethyl)-1H-indol-3-yl]-piperidin-1-yl}-ethoxy)-benzoic acid This compound was prepared following the procedure described in Example 138 (part B) starting with 1.4 g (3.1 mmol) of 2-{2-[4-(7-bromo-1H-indol-3-yl)-piperidin-1-yl]-ethoxy}-benzoic acid methyl ester (prepared as in Example 138, part A), 0.16 g (3.7 mmol) of NaH in 60% of mineral oil and 0.42 mL (3.7 mmol) of bromoethylethyl ether. The crude mixture was hydrolised following the procedure described in Example 138 (part C) and purified by chromatography over silica gel affording 0.34 g (28% of yield) of the desired product.

ESI/MS m/e=516 [(M+1)$^+$, C26H31 Br N2 O4]

NMR (300 MHz, CDCl$_3$) d=1.13–1.52 (t, 3H), 1.98–2.04 (m, 4H) 2.32–2.38 (m, 2H), 2.78–2.88 (m, 3H), 3.11–3.14 (d, 2H), 3.40–3.48 (m, 2H), 3.72–4.42 (m, 2H), 4.42–4.45 (t, 2H), 4.66–4.70 (t, 2H), 5.75–5.84 (bs, 1H), 6.88–6.97 (m, 2H), 7.05–7.13 (m, 2H), 7.32–7.34 (d, 1H), 7.49–7.53 (m, 2H), 7.91–7.95 (d, 1H)

EXAMPLE 145

Preparation of 2-(2-{4-[1-(2-ethoxy-ethyl)-5-fluoro-1H-indol-3-yl]-piperidin-1-yl}-ethoxy)-5-methyl-benzoic acid A. Preparation of 5-fluoro-3-piperidin-4-yl-1H-indole This compound was prepared following the procedure described in Example 1 (parts A and B) starting with 0.7 g (5.5 mmol) of 5-fluoroindol and 2.1 g (13.6 mmol) of 4-piperidone monohydrate hydrochloride. After the usual work-up 0.8 g (67% of yield) of the desired product were obtained.

ESI/MS m/e=219 [(M+1)$^+$, C13H15 F N2]

B. Preparation of 2-(2-{4-[1-(2-ethoxyethyl)-5-fluoro-1H-indol-3-yl]-piperidin-1-yl}-ethoxy)-5-methyl-benzoic acid This compound was prepared following the procedure described in Example 138 (part B) starting with 0.014 g (0.034 mmol) of 2-{2-[4-(5-fluoro-1H-indol-3-yl)-piperidin-1-yl]-ethoxy}-5-methyl-benzoic acid methyl ester (prepared as in Example 138 (part A), 0.003 g (0.08 mmol) of NaH in 60% of mineral oil and 0.046 mL (0.044 mmol) of bromoethylethyl ether. The crude mixture was hydrolised following the procedure described in Example 138 (part C) and purified by chromatography over silica gel affording 0.005 g (33% of yield) of the desired product.

ESI/MS m/e=469 [(M+1)$^+$, C27H33 F N2 O4]

NMR (300 MHz, CDCl$_3$) d=1.02–1.06 (m, 3H), 1.87–2.05 (m, 4H), 2.15–2.25 (m, 3H), 2.60–2.73 (m, 2H), 2.87–3.10 (m, 3H), 3.20–3.24 (d, 2H), 3.35–3.38 (m, 2H), 3.64–3.67 (t, 2H), 4.25–4.29 (t, 2H), 4.35–4.42 (m, 2H), 6.95–7.49 (m, 7H)

EXAMPLE 146

Preparation of 2-(2-{4-[1-(2-ethoxy-ethyl)-5-fluoro-1H-indol-3-yl]-piperidin-1-yl}-ethoxy)-4-methoxy-benzoic acid A. Preparation of 2-(2-chloro-ethoxy)-4-methoxy-benzoic acid methyl ester This compound was prepared following the procedure described in Example 1 (part C) starting with 5 g (27.4 mmol) of 2-hydroxy-5-methyl-benzoic acid methyl ester, 9 mL (60.3 mmol) of 1-bromo-2-chloro-ethane and 5.9 g (42.8 mmol) of potassium carbonate. After the work-up and purification, 6.6 g (99% of yield) of the desired product was obtained.

NMR (300 MHz, CDCl$_3$) d=3.81–3.89 (m, 8H), 4.26–4.30 (t, 2H), 6.48–6.49 (d, 1H), 6.54–6.58 (dd, 1H), 7.85–7.88 (d, 1H)

B. Preparation of 2-(2-{4-[1-(2-ethoxy-ethyl)-5-fluoro-1H-indol-3-yl]-piperidin-1-yl}-ethoxy)-4-methoxy-benzoic acid This compound was prepared following the procedure described in Example 138 (part B) starting with 0.024 g (0.056 mmol) of 2-{2-[4-(5-fluoro-1H-indol-3-yl)-piperidin-1-yl]-ethoxy}-4-methoxy-benzoic acid methyl ester (prepared as in Example 138, part A), 0.005 g (0.12 mmol) of NaH in 60% of mineral oil and 0.076 mL (0.072 mmol) of bromoethylethyl ether. The crude mixture was hydrolised following the procedure described in Example 138 (part C) and purified by chromatography over silica gel affording 0.012 g (44% of yield) of the desired product.

ESI/MS m/e=485 [(M+1)$^+$, C27H33 F N2 O5]

NMR (300 MHz, DMSO) d=1.01–1.06 (t, 3H), 1.81–2.05 (m, 4H), 2.58–2.70 (m, 2H), 2.81–2.92 (m, 2H), 2.95–3.08 (m, 3H) 3.29–3.69 (m, 5H), 3.77 (s, 3H), 4.25–4.28 (t, 2H), 4.38–4.42 (t, 2H), 6.61–6.65 (dd, 1H), 6.77–6.78 (d, 1H), 7.21 (s, 1H), 7.36–7.40 (dd, 1H), 7.44–7.48 (dd, 1H), 7.63–7.66 (d, 1H)

EXAMPLE 147

Preparation of 2-(2-{4-[1-(2-ethoxy-ethyl)-7-methyl-1H-indol-3-yl]-piperidin-1-yl}-ethoxy)-benzoic acid A. Preparation of 7-methyl-3-piperidin-4-yl-1H-indole This compound was prepared following the procedure described in Example 1 (parts A and B) starting with 1 g (7.6 mmol) of 7-methylindol and 2.9 g (19 mmol) of 4-piperidone monohydrate hydrochloride. After the usual work-up 0.8 g (50% of yield) of the desired product were obtained.

ESI/MS m/e=215 [(M+1)+, C14H18 N2]

B. Preparation of 2-(2-{4-[1-(2-ethoxy-ethyl)-7-methyl-1H-indol-3-yl]-piperidin-1-yl}-ethoxy)-benzoic acid This compound was prepared following the procedure described in Example 138 (part B) starting with 0.068 g (0.172 mmol) of 2-{2-[4-(7-methyl-1H-indol-3-yl)-piperidin-1-yl]-ethoxy}-benzoic acid methyl ester (prepared as in Example 138, part A), 0.010 g (0.26 mmol) of NaH in 60% of mineral oil and 0.023 mL (0.22 mmol) of bromo-ethylethyl ether. The crude mixture was hydrolised following the procedure described in Example 138 (part C) and purified by chromatography over silica gel affording 0.074 g (93% of yield) of the desired product.

ESI/MS m/e=451 [(M+1)+, C27H34 N2 O4]

NMR (300 MHz, DMSO) d=1.02–1.07 (t, 3H), 1.92–2.11 (m, 4H), 2.65 (s, 3H), 2.60–2.78 (m, 2H), 2.81–3.04 (m, 3H), 3.24–3.28 (d, 2H), 3.32–3.40 (q, 2H), 3.62–3.66 (t, 2H), 4.43–4.47 (m, 4H), 5.00–5.18 (bs, 1H), 6.85–6.91 (m, 2H), 7.00–7.05 (m, 2H), 7.22–7.24 (d, 1H), 7.37–7.47 (m, 2H), 7.54–7.56 (d, 1H)

EXAMPLE 148

Preparation of 2-{2-[4-(1-butyl-1H-indol-3-yl)-piperidin-1-yl]-ethoxy}-benzoic acid This compound was prepared following the procedure described in Example 138 (part B) starting with 0.119 g (0.31 mmol) of 2-{2-[4-(1H-indol-3-yl)-piperidin-1-yl]-ethoxy}-benzoic acid methyl ester, 0.022 g (0.53 mmol) of NaH in 60% of mineral oil and 0.044 mL (0.41 mmol) of butyl iodide. The crude mixture was hydrolised following the procedure described in Example 138 (part C) and purified by chromatography over silica gel affording 0.054 g (42% of yield) of the desired product.

ESI/MS m/e=421 [(M+1)+, C26H32 N2 O3]

NMR (300 MHz, DMSO) d=0.86–0.91 (t, 3H), 1.21–1.29 (m, 2H), 1.68–1.96 (m, 6H), 2.32–2.43 (m, 2H), 2.80–2.84 (m, 3H), 3.12–3.16 (d, 2H), 4.08–4.12 (t, 2H), 4.22–4.26 (t, 2H), 6.85–7.25 (m, 6H), 7.31–7.33 (d, 1H), 7.39–7.42 (d, 1H), 7.59–7.61 (d, 1H)

EXAMPLE 149

Preparation of 2-{2-[4-(1-hexyl-1H-indol-3-yl)-piperidin-1-yl]-ethoxy}-benzoic acid This compound was prepared following the procedure described in Example 138 (part B) starting with 0.119 g (0.31 mmol) of 2-(2-[4-(1H-indol-3-yl)-piperidin-1-yl]-ethoxy}-benzoic acid methyl ester, 0.022 g (0.52 mmol) of NaH in 60% of mineral oil and 0.058 mL (0.41 mmol) of hexyl iodide. The crude mixture was hydrolised following the procedure described in Example 138 (part C) and purified by chromatography over silica gel affording 0.047 g (34% of yield) of the desired product.

ESI/MS m/e=449 [(M+1)+, C28H36 N2 O3]

NMR (300 MHz, DMSO) d 0.81–0.85 (m, 3H), 1.20–1.25 (m, 6H), 1.68–1.94 (m, 6H), 2.29–2.36 (m, 2H), 2.73–2.84 (m, 2H), 3.10–3.14 (d, 2H), 4.06–4.10 (t, 2H), 4.15–4.21 (m, 2H), 6.87–7.12 (m, 5H), 7.19–7.25 (m, 1H), 7.37–7.41 (m, 2H), 7.58–7.60 (d, 1H)

EXAMPLE 150

Preparation of 2-{2-[4-(1-cyclopropylmethyl-6-fluoro-1H-indol-3-yl)-piperidin-1-yl]-ethoxy}-benzoic acid A. Preparation of 2-{2-[4-(6-fluoro-1H-indol-3-yl)-piperidin-1-yl]-ethoxy}-benzoic acid methyl ester This compound was prepared following the procedure described in Example 138 (part A) starting with 1.2 g (5.5 mmol) of 6-fluoroindol, prepared as in Example 1 (parts A and B) and 1.53 g (7.2 mmol) of 2-(2-chloro-ethoxy)-benzoic acid methyl ester affording 2.1 g (96% of yield) of the desired product.

ESI/MS m/e=397 [(M+1)+, C23H25 F N2 O3]

B. Preparation of 2-{2-[4-(1-cyclopropylmethyl-6-fluoro-1H-indol-3-yl)-piperidin-1-yl]-ethoxy}-benzoic acid This compound was prepared following the procedure described in Example 138 (part B) starting with 2 g (5.1 mmol) of 2-{2-[4-(6-fluoro-1H-indol-3-yl)-piperidin-1-yl]-ethoxy}-benzoic acid methyl ester, 0.51 g (12.8 mmol) of NaH 60% in mineral oil and 0.99 mL (10.2 mmol) of cyclopropylmethyl bromide. The crude mixture was hydrolised following the procedure described in Example 138 (part C) and purified by flash chromatography over silica gel affording 0.32 g (18% of yield) of the desired product.

Melting point=97° C.

ESI/MS m/e=437[(M+1)+, C26H29 F N2 O3]

NMR (300 MHz, CDCl3) d=0.33–0.38 (m, 2H), 0.59–0.66 (m, 2H), 1.21–1.27 (m, 1H), 1.95–2.10 (m, 4H), 2.33–2.41 (m, 2H), 2.80–2.85 (m, 3H), 3.13–3.17 (m, 2H), 3.84–3.86 (m, 2H), 4.41–4.44 (t, 2H), 6.50 (bs, 1H), 6.80–6.87 (t, 1H), 6.96–7.12 (m, 4H), 7.41–7.47 (m, 2H), 7.90–7.93 (t, 1H)

EXAMPLE 151

Preparation of 2-{2-[4-(1H-indol-3-yl)-piperidin-1-yl]-ethoxy}-benzoic acid

A solution of 1.33 g (33 mmol) of sodium hydroxide in 120 mL of water was added to a suspension of 6.31 g (16.6 mmol) of 2-{2-[4-(1H-indol-3-yl)-piperidin-1-yl]-ethoxy}-benzoic acid methyl ester (prepared in Example 1, part D) in 120 mL of ethanol. This mixture was heated at 60° C. for 3 hours and the solvent was removed under reduced pressure. After addition of 50 mL of water, the crude mixture was neutralised with HCl 2N and the solid formed was isolated. After recrystallisation from acetonitrile, 2.6 g (43% of yield) of a white solid corresponding to the desired product were obtained.

Melting point=230° C.

ESI/MS m/e=365 [(M+1)+, C22H24 N2 O3]

NMR (300 MHz, CDCl$_3$) d=1.91–2.07 (m, 4H), 2.53–2.72 (m, 2H), 2.86–2.98 (m, 3H), 3.19–3.23 (d, 2H), 4.38–4.44 (m, 2H), 6.93–7.09 (m, 4H), 7.21–7.24 (d, 1H), 7.33–7.42 (m, 2H), 7.54–7.56 (d, 1H), 7.62–7.64 (d, 1H)

EXAMPLE 152

Preparation of 4-{2-[4-(1-(2-ethoxy-ethyl)-1H-indol-3-yl)-piperidin-1-yl]-ethoxy}-benzoic acid (alternative preparation)

A. Preparation of 4-(1H-indol-3-yl)-3,6-dihydro-2H-pyridine-1-carboxylic acid ethyl ester 5 g of 3-(1,2,3,6-tetrahydro-pyridin-4-yl)-1H-indole prepared in Example 1 (part A) were dissolved in 25 mL of dichloromethane and 3.22 g of triethylamine were added to the solution. Keeping the temperature between 20 and 25° C., 3.14 g of ethyl chloroformate were added dropwise. The mixture was stirred for 2 hours and 20 mL of water were added. The organic layer was separated and the solvent was was removed under reduced pressure affording 5.22 g of a colourless oil.

B. Preparation of 4-(1H-indol-3-yl)-piperidine-1-carboxylic acid ethyl ester

In a sealed steel vessel, 5.1 g of 4-(1H-indol-3-yl)-3,6-dihydro-2H-pyridine-1-carboxylic acid ethyl ester were dissolved in 13.5 mL of methanol. The solution was submited to hydrogenation at 8–10 Kp/cm$^2$ of pressure, using 0.8 g of palladium on carbon 10% as catalyst. The mixture was stirred at 20–25° C. for 12 hours. The catalyst was removed and the solvent distilled off. A mixture of methanol/water 85:15 was added and 4.12 g (80% yield) of a white solid were collected.

Melting point: 114–116° C.

C. Preparation of 4-[1-(2-ethoxy-ethyl)-1H-indol-3-yl]-piperidine-1-carboxylic acid ethyl ester 0.75 g of a60% suspension of sodium hydride in mineral oil were suspended in 20 mL of dry DMF and 4 g of 4-(1H-indol-3-yl)-piperidine-1-carboxylic acid ethyl ester were added to the mixture. 1.91 g of 2-chloroethyl ethyl ether were added dropwise at room temperature and the mixture was stirred for 16 hours at 20–25° C. Water was carefully added and ethyl acetate was used as solvent extractor. The organic layer was separated and washed with water. The solvent was removed under reduced pressure affording 4.58 g of a colorless oil. The product was then crystallised from methyl-t-butyl ether/hexane giving a off white solid.

Melting point: 56–58° C.

D. Preparation of 4-[1-(2-ethoxy-ethyl)-indol-3-yl]-piperidine 4 g of 4-[1-(2-ethoxy-ethyl)-1H-indol-3-yl]-piperidine-1-carboxylic acid ethyl ester and 3.81 g of potassium hydroxide 85% were added to 14 g of 2-propanol and the mixture was heated at 95–100° C. for 16 hours. The solvent was distilled off and water was added. The mixture was extracted with toluene and the organic layer was separated, washed with water and concentrated. The residue was disolved in a mixture of 10 mL of ethyl alcohol 96% and 6 mL of 2-propanol and 1.4 g of fumaric acid were added. The mixture was refluxed for 30 minutes. After cooling at 0–5° C. for 30 minutes the formed solid was isolated by suction filtration. 4.05 g of a white solid were recovered as a salt of the product with fumaric acid.

Melting point: 166–168° C.

E. Preparation of 4-{2-[4-(1-(2-ethoxy-ethyl)-1H-indol-3-yl)-piperidin-1-yl]-ethoxy}-benzoic acid 0.5 g (1.84 mmol) of 4-[1-(2-ethoxy-ethyl)-indol-3-yl]-piperidine and 0.55 g (2.4 mmol) of ethyl 4-chloro-ethoxy-benzoate were disolved in 6 mL of 4-methyl-2-butanone and 0.38 g (2.76 mmol) of potassium carbonate were added. The mixture was refluxed for 18 hours and after cooling, water was added, the organic layer separated, washed with water and brine. The solvent was distilled off. The obtained crude was disolved in 3 mL of ethyl alcohol 96% and 2 mL of a 2N aqueous sodium hydroxide solution were added. After stirring at room temperature for 18 hours the mixture was neutralised with a sulphuric acid solution 10%. The formed solid (0.390 g, 65% yield) was collected, washed with water and dried.

Melting point: 85° C.

EXAMPLE 153

Preparation of 3-{4-[1-(2-ethoxy-ethyl)-1H-indol-3-yl]-piperidin-1-yl}-propionic acid To a solution of 0.5 g (1.84 mmol) of 4-[1-(2-ethoxy-ethyl)-indol-3-yl)-piperidine prepared as in Example 152 (part D) in 6 mL of ethyl alcohol, 0.240 g (2.4 mmol) of ethyl acrylate were added. The mixture was refluxed for 18 hours and the solvent was removed under reduced pressure. The residue was extracted between water and ethyl acetate. The crude product obtained after removing the solvent was dissolved with 3 mL of ethyl alcohol and 2 mL of a 2N aqueous sodium hydroxide solution were added. The mixture was stirred at room temperature for 18 hours and then neutralised with HCl 6N. After extraction with chloroform and removal of the solvent, 0.420 g (67%) of a yellow oil were isolated.

ESI/MS m/e=345 [(M+1)$^+$, C20H28 N2 O3]

NMR (300 MHz, DMSO) d=1.01–1.06 (t, 3H), 1.83–2.05 (m, 4H), 2.61–2.75 (m, 4H), 2.95–3.15 (m, 3H), 3.29–3.41 (m, 4H), 3.63–3.67 (m, 2H), 4.21–4.27 (m, 2H), 6.93–7.07 (m, 1H), 7.11–7.15 (m, 2H), 7.43 (d, 1H), 7.59–7.61 (d, 1H)

EXAMPLE 154

Preparation of 2-(2-{4-[1-(2-ethoxy-ethyl)-1H-indol-3-yl]-piperidin-1-yl}-ethoxy)-5-methyl-benzoic acid This compound was prepared following the procedure described in Example 152 (parts D and E) starting with 0.85 g (3.1 mmol) of 1-(2-ethoxyethyl)-3-piperidin-4-yl-1H-indole, 0.97 g (4.0 mmol) of 2-(2-chloroethoxy)-5-methyl-benzoic acid methyl ester, 0.65 g (4.7 mmol) of potassium carbonate and 0.38 g (2.3 mmol) of potassium iodide. After the saponication and purification through silica gel 0.52 g (36%) of the corresponding carboxylic acid were obtained.

Melting point=109–112° C.

ESI/MS m/e=451 [(M+1)$^+$, C27H34 N2 O4]

NMR (300 MHz, CDCl$_3$) d=1.12–1.19 (t, 3H), 2.01–2.05 (m, 4H), 2.31 (s, 3H), 2.36–2.39 (m, 2H), 2.80–2.84 (t, 2H), 2.85–2.90 (m, 1H), 3.13–3.16 (d, 2H), 3.42–3.49 (q, 2H), 3.72–3.76 (t, 2H), 4.22–4.27 (t, 2H), 4.38–4.42 (t, 2H), 6.10–6.20 (bs, 1H), 6.94–7.26 (m, 5H), 7.33–7.36 (d, 1H), 7.56–7.59 (d, 1H), 7.71 (s, 1H)

EXAMPLE 155

Preparation of 2-[4-(4-{4-[1-(2-ethoxy-ethyl)-1H-indol-3-yl]-piperidin-1-yl}-butyryl)-phenyl]-2-methyl-propionic acid This compound was prepared following the procedure described in Example 152 (parts D and E) starting with 0.1 g (0.37 mmol) of 1-(2-ethoxyethyl)-3-piperidin-4-yl-1H-indole, 0.142 g (0.48 mmol) of 2-[4-(4-chlorobutyryl)-phenyl]-2-methyl-propionic acid methyl ester, 0.07 g (0.48 mmol) of potassium carbonate and 0.04 g (0.24 mmol) of potassium iodide.

ESI/MS m/e=505 [(M+1)$^+$, C31H40 N2 O4]

NMR (300 MHz, DMSO) d=1.02–1.06 (t, 3H), 1.51 (s, 6H), 1.98–2.50 (m, 6H), 2.73–2.96 (m, 5H), 3.10–3.14 (t, 2H), 3.31–3.42 (m, 4H), 3.64–3.67 (t, 2H), 4.24–4.27 (t, 2H), 6.97–7.02 (t, 1H), 7.09–7.14 (m, 2H), 7.43–7.62 (m, 3H), 7.62–7.64 (d, 1H), 7.94–7.96 (m, 2H)

EXAMPLE 156

Preparation of 1-(2-ethoxy-ethyl)-3-(1-{3-[4-(2H-tetrazol-5-yl)-phenoxy]-propyl}-piperidin-4-yl)-1H-indole A. Preparation of 4-(3-{4-[1-(2-ethoxyethyl)-1H-indol-3-yl]-piperidin-1-yl}-propoxy)-benzonitrile A solution of 0.32 g (1.34 mmol) of 4-(3-bromopropoxy)-benzonitrile in 1 mL of isobutylmethylketone was added to a mixture of 0.28 g (1.03 mmol) of 1-(2-ethoxyethyl)-3-piperidin-4-yl-1H-indole prepared as in Example 142 (part D), 0.21 g (1.6 mmol) of potassium carbonate and 0.13 g (0.8 mmol) of potassium iodide in 4.5 mL of isobutylmethylketone. The reaction mixture was refluxed for 16 hours and after filtering the inorganic salts, the solvent was removed under reduced pressure. The crude mixture was purified by flash chromatography over silica gel affording 0.31 g (70% yield) of 4-(3-{4-[1-(2-ethoxy-ethyl)-1H-indol-3-yl]-piperidin-1-yl}-propoxy)-benzonitrile.

NMR (300 MHz, CDCl$_3$) d=1.12–1.19 (t, 3H), 1.87–2.26 (m, 8H), 2.57–2.64 (t, 2H), 2.80–2.92 (m, 1H), 3.07–3.13 (d, 2H), 3.37–3.48 (q, 2H), 3.69–3.74 (t, 2H), 4.07–4.13 (t, 2H), 4.21–4.27 (t, 2H), 6.93–7.35 (m, 5H), 7.35–7.65 (m, 4H)

B. Preparation of 1-(2-ethoxy-ethyl)-3-(1-{3-[4-(2H-tetrazol-5-yl)-phenoxy]-propyl}-piperidin-4-yl)-1H-indole To a solution of 0.108 g (0.25 mmol) of 4-(3-{4-[1-(2-ethoxyethyl)-1H-indol-3-yl]-piperidin-1-yl}-propoxy)-benzonitrile in 1.5 mL of anhydrous DMF, 0.110 g (2 mmol) of ammonium chloride and 0.135 g (2 mmol) of sodium azide were added. The crude mixture was heated at 110° C. for 18 hours and after cooling at room temperature, 1 mL of an aqueous solution of 2N sodium hydroxide was added. The mixture was taken to pH=6 and the aqueous phase was extracted with ethyl acetate. After purification by flash cromatography over silica gel 0.05 g (41% yield) of the desired product were obtained.

ESI/MS m/e=475 [(M+1)$^+$, C27H34 N6 O2]

NMR (300 MHz, DMSO) d=1.02–1.07 (t, 3H), 1.92–2.11 (m, 2H), 2.14–2.49 (m, 4H), 2.94–3.02 (m, 3H), 3.11–3.16 (t, 2H), 3.47–3.51 (d, 2H), 3.64–3.68 (t, 2H), 4.12–4.16 (t, 2H), 4.25–4.29 (t, 2H), 6.98–7.18 (m, 5H), 7.44–7.47 (d, 1H), 7.62–7.64 (d, 1H), 7.94–7.97 (m, 2H)

EXAMPLE 157

Preparation of 2-{2-[4-(1-cyclopropylmethyl-1H-indol-3-yl)-piperidin-1-yl]-ethoxy}-benzoic acid A. Preparation of 4-(1H-indol-3-yl)-piperidine-1-carboxylic acid ethyl ester 17 mL (0.18 mol) of ethyl chloroformiate were added to a suspension of 30 g (0.15 mol) of 4-(3-indolyl)-piperidine and 28 mL (0.18 mol) of triethylamine in 185 mL of dichloromethane, keeping the temperature between 20 and 25° C. The mixture was stirred at room temperature for 2 hours and 150 mL of water were added. The organic layer was separated and the solvent was removed under reduced pressure affording 36 g (88% of yield) of the desired product.

B. Preparation of 4-(1-cyclopropylmethyl-1H-indol-3-yl)-piperidine-1-carboxylic acid ethyl ester To a suspension of 0.76 g (19 mmol) of a 60% suspension of sodium hydroxide, in mineral oil, in 15 mL of anhydrous DMF, a solution of 4 g (15 mmol) of 4-(1H-indol-3-yl)-piperidine-1-carboxylic acid ethyl ester in 5 mL of anhydrous DMF was added. After 30 minutes at room temperature, a solution of 1.71 mL (18 mmol) of cyclopropylmethyl bromide in 5 mL of DMF was added. The crude mixture was stirred at room temperature for 14 h and the solvent was removed under reduced pressure. The crude mixture was extracted between water and ethyl acetate. The organic layer was dried over magnesium sulfate, and after filtration the solvent was removed under reduced pressure affording 4.7 g of the desired product.

ESI/MS m/e=327 [(M+1)$^+$, C20H26 N2 O2]

C. Preparation of 1-cyclopropylmethyl-3-piperidin-4-yl-1H-indole

A solution of 4.95 g (75 mmol) of potassium hydroxide in 25 mL of iso-propanol was added to 4.7 g (15 mmol) of 4-(1-cyclopropylmethyl-1H-indol-3-yl)-piperidine-1-carboxylic acid ethyl ester and the mixture was heated at 95–100° C. for 16 hours. The solvent was removed under reduced pressure and the crude mixture was extracted between water and toluene. The organic layer was dried over sodium sulfate and after filtration the solvent was removed under reduced pressure affording 3.2 g (89% of yield) of the desired product.

ESI/MS m/e=255[(M+1)$^+$, C17H22 N2]

D. Preparation of 2-{2-[4-(1-cyclopropylmethyl-1H-indol-3-yl)-piperidin-1-yl]-ethoxy}-benzoic acid A suspension containing 3.6 g (14 mmol) of 1-cyclopropylmethyl-3-piperidin-4-yl-1H-indole, 3.7 g (18 mmol) of 2-(2-chloro-ethoxy)-benzoic acid methyl ester (prepared in Example 1, part C), 2.9 g (21 mmol) of potassium carbonate and 1.7 g (11 mmol) of potassium iodide in 70 mL of iso-butylmethylketone was heated at 90° degrees for 16 hours. The solvent was removed under reduced pressure and the crude mixture was extracted between water and dichloromethane. The organic layer was dried over sodium sulfate and after filtration the solvent was removed under reduced pressure affording 6.5 g of a colorless oil. This crude mixture was dissolved in 350 mL of ethanol and 14 mL of a 2N aqueous solution of sodium hydroxide. The mixture was stirred for 16 hours at room temperature and the solvent was removed under reduced pressure and 50 mL of water were added. The crude mixture was neutralised, extracted with cholorform and purified by flash chromatography over silica gel affording 2.27 g (39% of yield) of the desired product.

Melting point=145–147° C.

ESI/MS m/e=419 [(M+1)$^+$, C26H30 N2 O3]

NMR (300 MHz, DMSO) d=0.36–0.39 (m, 2H), 0.47–0.51 (m, 2H), 0.1.17–1.24 (m, 1H), 1.92–1.99 (m, 4H), 2.60–2.69 (m, 2H), 2.90–2.97 (m, 3H), 3.20–3.24 (d, 2H), 3.97–3.99 (d, 2H), 4.42–4.45 (t, 2H), 6.10 (bs, 1H), 6.97–7.04 (m, 2H), 7.09–7.14 (t, 1H), 7.20–7.24 (m, 2H), 7.36–7.47 (m, 2H), 7.52–7.54 (d, 1H), 7.64–7.66 (d, 1H)

EXAMPLE 158

Preparation of 3-[4-(1-cyclopropylmethyl-1H-indol-3-yl)-piperidin-1-ylmethyl]-benzoic acid This compound was prepared following the procedure described in Example 157 (part D) starting with 1.5 g (6 mmol) of 1-cyclopropylmethyl-3-piperidin-4-yl-1H-indole, 1.8 g (7.8 mmol) of 3-bromomethyl-benzoic acid methyl ester, 1.2 g (9 mmol) of potassium carbonate and 0.9 g (4.5 mmol) of potassium iodide in 25 mL of iso-butylmethylketone. The crude mixture was purified by flash chromatography over silica gel affording 0.63 g (27% of yield) of the desired product.

Melting point=207° C.

ESI/MS m/e=389 [(M+1)$^+$, C25H28 N2 O2]

NMR (300 MHz, DMSO) d=0.33–0.37 (m, 2H), 0.46–0.50 (m, 2H), 1.17–1.25 (m, 1H), 1.70–1.78 (m, 2H), 1.92–1.97 (d, 2H), 2.20–2.27 (t, 2H), 2.75–2.82 (m, 1H), 2.94–2.98 (d, 2H), 3.66 (s, 2H), 3.95–3.98 (d, 2H), 6.95–7.00 (t, 1H), 7.07–7.12 (t, 1H), 7.20 (s, 1H), 7.43–7.62 (m, 4H), 7.85–7.88 (d, 1H), 7.96 (s, 1H).

EXAMPLE 159

Preparation of (4-{3-[4-(1-cyclopropylmethyl-1H-indol-3-yl)-piperidin-1-yl]-propoxy}-phenyl)-acetic acid This compound was prepared following the procedure described in Example 157 (part D) starting with 1.5 g (6 mmol) of 1-cyclopropylmethyl-3-piperidin-4-yl-1H-indole, 2 g (6.6 mmol) of [4-(3-chloro-propoxy)-phenyl]-acetic acid ethyl ester, 1.7 g (12 mmol) of potassium carbonate and 1 g (6.15 mmol) of potassium iodide in 32 mL of iso-butylmethylketone. The crude mixture was purified by flash chromatography over silica gel affording 1.6 g (58% of yield) of the desired product.

Melting point=83–85° C.

ESI/MS m/e=447 [(M+1)⁺, C28H34 N2 O3]

NMR (300 MHz, DMSO) d=0.35–0.37 (m, 2H), 0.47–0.50 (m, 2H), 1.13–1.20 (m, 1H), 1.66–1.76 (m, 2H), 1.89–1.97 (m, 4H), 2.05–2.13 (t, 2H), 2.46–2.50 (m, 2H), 2.71–2.78 (m, 1H), 2.97–3.00 (d, 2H), 3.45 (s, 2H), 3.95–4.01 (m, 4H), 6.85–6.88 (m, 2H), 6.95–7.00 (t, 1H), 7.07–7.18 (m, 4H), 7.42–7.45 (d, 1H), 7.54–7.56 (d, 1H)

EXAMPLE 160

Preparation of a Pharmaceutical Composition: Syrup 1000 bottles (150 ml volume) each containing a solution of 750 mg of 2-(2-{4-[1-(4-fluoro-benzyl)-1H-indol-3-yl]-piperidin-1-yl}-ethoxy)-benzoic acid were prepared as follows:

| | |
|---|---|
| 2-(2-{4-[1-(4-flouro-benzyl)-1H-indol-3-yl]-piperidin-1-yl}-ethoxy)-benzoic acid | 750 g |
| glycerin | 15,000 g |
| hydrogenated castor oil-ethylene oxide | 1,500 g |
| sodium methyl p-hydroxybenzoate | 240 g |
| sodium propyl p-hydroxybenzoate | 60 g |
| sodium saccharin | 300 g |
| flavouring | q.s |
| sodium hydroxide q.s. | pH = 4 |
| demineralised water q.s. | 150 liters |

Procedure

To a solution of the sodium methyl (and propyl) p-hydroxybenzoates and sodium saccharin in 30 liters of demineralised water, an aqueous glycerin solution and hydrogenated castor oil-ethylene oxide was added. After stirring, the 2-(2-{4-[1-(4-fluoro-benzyl)-1H-indol-3-yl]-piperidin-1-yl}-ethoxy)-benzoic acid was added and homogenized to reach complete dissolution. After this, the flavouring agent was mixed into the solution with vigorous stirring, and the mixture was made up to final volume with demineralised water.

The resultant solution was filled into 150 ml bottles using an appropriate filling machine.

EXAMPLE 161

Preparation of a Pharmaceutical Composition: Capsules 50,000 capsules each containing 50 mg of 2-{2-[4-(1-pentyl-1H-indol-3-yl)-piperidin-1-yl]-ethoxy}-benzoic acid were prepared from the following formulation:

| | |
|---|---|
| 2-{2-[4-(1-pentyl-1H-indol-3-yl)-piperidin-1-yl]-ethoxy}-benzoic acid | 2,500 g |
| magnesium stearate | 225 g |
| lactose spray dried | 18,350 g |
| cross-linked sodium carboxymethylcellulose | 900 g |
| sodium lauryl sulphate | 450 g |

Procedure

The 2-{2-[4-(1-pentyl-1H-indol-3-yl)-piperidin-1-yl]-ethoxy}-benzoic acid, sodium lauryl sulphate, lactose and cross-linked sodium carboxymethylcellulose were mixed together and passed through a screen with an opening of 0.6 mm. The magnesium stearate was added and the mixture encapsulated into gelatine capsules of appropriate size.

EXAMPLE 162

Preparation of a Pharmaceutical Composition: Tablets 100,000 tablets each containing 25 mg of 2-(2-{4-[1-(2-ethoxy-ethyl)-1H-indol-3-yl]-piperidin-1-yl}-ethoxy)-benzoic acid were prepared from the following formulation:

| | |
|---|---|
| 2-(2-{4-[1-(2-ethoxyethyl)-1H-indol-3-yl]-piperidin-1-yl}-ethoxy)-benzoic acid | 2,500 g |
| microcrystalline cellulose | 1,650 g |
| lactose spray dried | 9,620 g |
| carboximethyl starch | 570 g |
| sodium stearyl fumarate | 80 g |
| colloidal silicon dioxide | 80 g |

Procedure

All the powders were passed through a screen with apertures of 0.6 mm. They were then all mixture in a suitable mixer for 30 minutes and compressed into 145 mg tablets using 6 mm discs and flat bevelled punches. The disintegration time of the tablets was about 60 seconds.

What is claimed is:

1. A compound of formula (I)

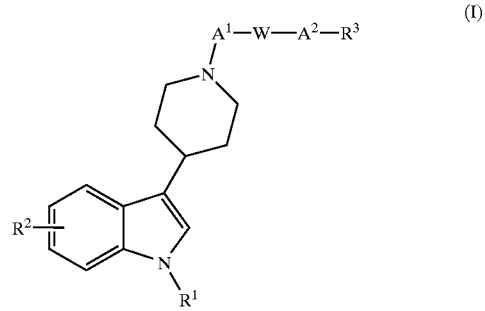

wherein:

$A^1$ represents an alkylene, alkyleneoxy, alkylenethio, alkanoyl or hydroxyalkylene group;

$A^2$ represents a single bond, an alkylene or alkenylene group;

W represents a single bond or a phenylene or furanylene group which is unsubstituted or substituted by one or more halogen atoms, alkoxy groups and/or alkyl groups;

$R^1$ represents a hydrogen atom or an alkyl, alkenyl, alkynyl, alkoxyalkyl, alkenyloxyalkyl, alkynyloxyalkyl alkoxy-alkoxyalkyl, phenylalkyl group wherein the phenyl ring is unsubstituted or substituted by one or more halogen atoms or alkyl, alkoxy or arylalkoxy groups, or a cycloalkylalkyl group wherein the cycloalkyl group is unsubstituted or substituted by one or more halogen atoms, alkyl groups or alkoxy groups;

$R^2$ represents a hydrogen halogen atom or an alkyl or alkoxy group; and $R^3$ represents a carboxyl group or a tetrazolyl group; and pharmaceutically acceptable salts thereof.

2. A compound according to claim 1 wherein the alkyl, alkylene, alkenylene, alkyleneoxy, alkylenethio, alkanoyl, hydroxyalkylene and alkoxy groups have up to 7 carbon atoms.

51

3. A compound according to claim 1 wherein $A^1$ represents an alkylene, alkyleneoxy, hydroxyalkylene or alkylenethio group.

4. A compound according to claim 3 wherein $A^1$ represents a methylene, ethylene, propylene, butylene, pentylene, hexylene, ethyleneoxy, propyleneoxy, hydroxybutylene, ethylsulfanyl or butylsulfanyl group.

5. A compound according to claim 1 wherein W represents a furanylene group or a phenylene group which is unsubstitued or substituted by one or two fluorine, chlorine or bromine atoms, methyl groups or methoxy groups.

6. A compound according to claim 5 wherein W represents an unsubstituted furanylene, unsubstituted phenylene, fluorophenylene, dibromophenylene, methylphenylene or methoxyphenylene group.

7. A compound according to claim 1 wherein $A^2$ represents a single bond, a $C_{1-4}$ alkylene group or a $C_{2-5}$ alkenylene group.

8. A compound according to claim 7 wherein $A^2$ represents a single bond or a methylene, ethylene, propylene, methylethylene, butylene or ethenylene group.

9. A compound according to claim 1 wherein $R^1$ represents a hydrogen atom or a $C_{1-7}$ alkyl, alkenyl or alkynyl group, a $C_{2-5}$ alkoxyalkyl group, a $C_{3-7}$ alkenoxy-alkyl group, a $C_{3-7}$ alkynoxy-alkyl group, a $C_{3-7}$ alkoxyalkoxyalkyl group, a benzyl or phenylethyl group which is unsubstituted or substituted by one or more halogen atoms, $C_{1-4}$ alkyl, methoxy or benzyloxy groups or a cycloalkylalkyl group wherein the cycloalkyl group is cyclopropyl, cyclobutyl, cyclopentyl, cyclohexyl, cycloheptyl or decalinyl which is unsubstituted or substituted by one or more halogen atoms, $C_{1-4}$ alkyl or methoxy groups and the alkyl part of the cycloalkylalkyl group is methylene, ethylene, propylene or butylene.

10. A compound according to claim 9 wherein $R^1$ represents a hydrogen atom or a propyl, butyl, isobutyl pentyl, hexyl, heptyl, 2-methylpropyl, 3-methylbutyl, allyl, propenyl, propynyl, methoxyethyl, methoxypropyl, ethoxyethyl, propoxyethyl, iso-propoxyethyl, prop-2-ynyloxyethyl, prop-2-enyloxyethyl, methoxyethoxyethyl, 4-fluorobenzyl, 4-methoxybenzyl, 4-(tert-butyl)-benzyl, 4-benzyloxybenzyl, 4-methoxyphenylethyl, cyclopropylmethyl, cyclopropylethyl, cyclopropylpropyl, cyclohexylmethyl, cyclohexylethyl or cyclohexylpropyl group.

11. A compound according to claim 1 wherein $R^2$ represents a hydrogen, fluorine, chlorine or bromine atom or a methyl or methoxy group.

12. A compound according to claim 1 which is
2-(2-{4-[1-(4-fluoro-benzyl)-1H-indol-3-yl]-piperidin-1-yl}-ethoxy)-benzoic acid
2-{2-[4-(1-pentyl-1H-indol-3-yl)-piperidin-1-yl]-ethoxy}-benzoic acid
4-{4-[1-(2-ethoxy-ethyl)-1H-indol-3-yl]-piperidin-1-yl}-butyric acid
3-(3-{4-[1-(4-fluoro-benzyl)-1H-indol-3-yl]-piperidin-1-yl}-propoxy)-benzoic acid
4-(3-[4-(1-pentyl-1H-indol-3-yl)-piperidin-1-yl]-propoxy}-benzoic acid
2-[2-(4-{1-[2-(2-methoxy-ethoxy)-ethyl]-1H-indol-3-yl}-piperidin-1-yl)-ethoxy]-benzoic acid
3-[2-(4-{1-[2-(2-methoxy-ethoxy)-ethyl]-1H-indol-3-yl}-piperidin-1-yl)-ethoxy]-benzoic acid

52

3-(2-{4-[1-(4-fluoro-benzyl)-1H-indol-3-yl]-piperidin-1-yl}-ethoxy)-benzoicacid
3-{2-[4-(1-pentyl-1H-indol-3-yl)-piperidin-1-yl]-ethoxy}-benzoic acid
3-(2-{4-[1-(2-ethoxy-ethyl)-1H-indol-3-yl]-piperidin-1-yl}-ethoxy)-benzoic acid
4-[2-(4-{1-[2-(2-methoxy-ethoxy)-ethyl]-1H-indol-3-yl}-piperidin-1-yl)-ethoxy]-benzoic acid
4-{2-[4-(1-pentyl-1H-indol-3-yl)-piperidin-1-yl]-ethoxy}-benzoic acid
2-[3-(4-{1-[2-(2-methoxy-ethoxy)-ethyl]-1H-indol-3-yl}-piperidin-1-yl)-propoxy]-benzoic acid
2-(3-{4-[1-(4-fluoro-benzyl)-1H-indol-3-yl]-piperidin-1-yl}-propoxy)-benzoic acid
2-{3-[4-(1-pentyl-1H-indol-3-yl)-piperidin-1-yl]-propoxy}-benzoic acid
2-(3-{4-[1-(2-ethoxy-ethyl)-1H-indol-3-yl]-piperidin-1-yl}-propoxy)-benzoic acid
3-[3-(4-{1-[2-(2-methoxy-ethoxy)-ethyl]-1H-indol-3-yl}-piperidin-1-yl)-propoxy]-benzoic acid
3-{3-[4-(1-pentyl-1H-indol-3-yl)-piperidin-1-yl]-propoxy}-benzoic acid
3-(3-{4-[1-(2-ethoxy-ethyl)-1H-indol-3-yl]-piperidin-1-yl}-propoxy)-benzoic acid
4-[3-(4-{1-[2-(2-methoxy-ethoxy)-ethyl]-1H-indol-3-yl}-piperidin-1-yl)-propoxy]-benzoic acid
4-(3-{4-[1-(2-ethoxy-ethyl)-1H-indol-3-yl]-piperidin-1-yl}-propoxy)-benzoic acid
3-(4-{1-[2-(2-methoxy-ethoxy)-ethyl]-1H-indol-3-yl}-piperidin-1-yl)-propionic acid
3-[4-(1-pentyl-1H-indol-3-yl)-piperidin-1-yl]-propionic acid
4-(4-{1-[2-(2-methoxy-ethoxy)-ethyl]-1H-indol-3-yl}-piperidin-1-yl)-butyric acid
4-(4-[1-(4-fluoro-benzyl)-1H-indol-3-yl]-piperidin-1-yl}-butyric acid
4-[4-(1-pentyl-1H-indol-3-yl)-piperidin-1-yl]-butyric acid
3-{4-[2-(4-{1-[2-(2-methoxy-ethoxy)-ethyl]-1H-indol-3-yl}-piperidin-1-yl)-ethyl]-phenyl}-propionic acid
3-{4-[1-(4-fluoro-benzyl)-1H-indol-3-yl]-piperidin-1-yl}-propionic acid
3-[4-(2-{4-[1-(2-ethoxy-ethyl)-1H-indol-3-yl]-piperidin-1-yl}-ethyl)-phenyl]-propionic acid
3-{4-[2-(4-{1-[2-(2-methoxy-ethoxy)-ethyl]-1H-indol-3-yl}-piperidin-1-yl)-ethyl]-phenyl}-acrylic acid
3-(4-{2-[4-(1-pentyl-1H-indol-3-yl)-piperidin-1-yl]-ethyl}-phenyl)-acrylic acid
3-[4-(2-(4-[1-(2-ethoxy-ethyl)-1H-indol-3-yl]-piperidin-1-yl}-ethyl)-phenyl]-acrylic acid
2-{4-[1-hydroxy-4-(4-{1-[2-(2-methoxy-ethoxy)-ethyl]-1H-indol-3-yl}-piperidin-1-yl)-butyl]-phenyl}-2-methyl-propionic acid
2-(4-{1-hydroxy-4-[4-(1-pentyl-1H-indol-3-yl)-piperidin-1-yl]-butyl}-phenyl)-2-methyl-propionic acid
2-[4-(4-{4-[1-(2-ethoxy-ethyl)-1H-indol-3-yl]-piperidin-1-yl}-1-hydroxy-butyl)-phenyl]-2-methyl-propionic acid
[2-(4-{1-[2-(2-methoxy-ethoxy)-ethyl]-1H-indol-3-yl}-piperidin-1-yl)-ethoxy]-acetic acid
(2-{4-[1-(4-fluoro-benzyl)-1H-indol-3-yl]-piperidin-1-yl}-ethoxy)-acetic acid {2-[4-(1-pentyl-1H-indol-3-yl)-piperidin-1-yl]-ethoxy}-acetic acid
(2-{4-[1-(2-ethoxy-ethyl)-1H-indol-3-yl]-piperidin-1-yl}-ethoxy)-acetic acid
5-(4-{1-[2-(2-methoxy-ethoxy)-ethyl]-1H-indol-3-yl}-piperidin-1-yl-methyl)-furan-2-carboxylic acid
5-[4-(1-pentyl-1H-indol-3-yl)-piperidin-1-yl-methyl]-furan-2-carboxylic acid
5-{4-[1-(2-ethoxy-ethyl)-1H-indol-3-yl]-piperidin-1-yl-methyl}-furan-2-carboxylic acid
5-{4-[1-(4-fluoro-benzyl)-1H-indol-3-yl]-piperidin-1-ylmethyl}-furan-2-carboxylic acid
2-[4-(4-{4-[1-(4-fluoro-benzyl)-1H-indol-3-yl]-piperidin-1-yl}-1-hydroxy-butyl)-phenyl]-2-methyl-propionic acid
2-(2-[4-(1-heptyl-1H-indol-3-yl)-piperidin-1-yl]-ethoxy}-benzoic acid
2-(2-{4-[1-(4-tert-butyl-benzyl)-1H-indol-3-yl]-piperidin-1-yl}-ethoxy)-benzoic acid
2-(2-{4-[1-(4-methoxy-benzyl)-1H-indol-3-yl]-piperidin-1-yl}-ethoxy)-benzoic acid
2-(2-{4-[1-(4-benzyloxy-benzyl)-1H-indol-3-yl]-piperidin-1-yl}-ethoxy)-benzoic acid
2-{2-[4-(1-iso-butyl-1H-indol-3-yl)-piperidin-1-yl]-ethoxy}-benzoic acid
2-[2-(4-{1-[2-(4-methoxy-phenyl)-ethyl]-1H-indol-3-yl}-piperidin-1-yl)-ethoxy]-benzoic acid
2-(4-{2-[4-(1H-indol-3-yl)-piperidin-1-yl]-ethyl}-phenyl)-2-methyl-propionic acid
2-(4-{4-[4-(1H-indol-3-yl)-piperidin-1-yl]-butyryl}-phenyl)-2-methyl-propionic acid
2-[4-(1H-indol-3-yl)-piperidin-1-ylmethyl]-benzoic acid
3-[4-(1H-indol-3-yl)-piperidin-1-ylmethyl]-benzoic acid
4-[4-(1H-indol-3-yl)-piperidin-1-ylmethyl]-benzoic acid
(3-{2-[4-(1H-indol-3-yl)-piperidin-1-yl]-ethoxy-phenyl)-acetic acid
(3-{3-[4-(1H-indol-3-yl)-piperidin-1-yl]-propoxy}-phenyl)-acetic acid
(4-{2-[4-(1H-indol-3-yl)-piperidin-1-yl]-ethoxy}-phenyl)-acetic acid
(4-{3-[4-(1H-indol-3-yl)-piperidin-1-yl]-propoxy)-phenyl)-acetic acid
3-(1-{3-[3-(1H-tetrazol-5-yl)-phenoxy]-propyl)-piperidin-4-yl)-1H-indole
2-methyl-2-[4-(2-{4-[1-(3-methyl-butyl)-1H-indol-3-yl]-piperidin-1-yl}-ethyl)-phenyl]-propionic acid
2-[4-(2-{4-[1-(2-ethoxy-ethyl)-1H-indol-3-yl]-piperidin-1-yl}-ethyl)-phenyl]-2-methyl-propionic acid
2-methyl-2-[4-(4-{4-[1-(3-methyl-butyl)-1H-indol-3-yl]-piperidin-1-yl}-butyryl)-phenyl]-propionic acid
2-{4-[1-(3-methyl-butyl)-1H-indol-3-yl]-piperidin-1-ylmethyl}-benzoic acid
2-{4-[1-(2-ethoxy-ethyl)-1H-indol-3-yl]-piperidin-1-ylmethyl}-benzoic acid
3-{4-[1-(2-ethoxy-ethyl)-1H-indol-3-yl]-piperidin-1-ylmethyl}-benzoic acid
4-{4-[1-(3-methyl-butyl)-1H-indol-3-yl]-piperidin-1-ylmethyl}-benzoic acid
[3-(2-{4-[1-(3-methyl-butyl)-1H-indol-3-yl]-piperidin-1-yl}-ethoxy)-phenyl]-acetic acid
[3-(2-{4-[1-(2-ethoxy-ethyl)-1H-indol-3-yl]-piperidin-1-yl}-ethoxy)-phenyl]-acetic acid
[3-(3-{4-[1-(3-methyl-butyl)-1H-indol-3-yl]-piperidin-1-yl}-propoxy)-phenyl]-acetic acid
[3-(3-{4-[1-(2-ethoxy-ethyl)-1H-indol-3-yl]-piperidin-1-yl}-propoxy)-phenyl]-acetic acid
[4-(2-{4-[1-(3-methyl-butyl)-1H-indol-3-yl]-piperidin-1-yl}-ethoxy)-phenyl]-acetic acid
[4-(2-{4-[1-(2-ethoxy-ethyl)-1H-indol-3-yl]-piperidin-1-yl}-ethoxy)-phenyl]-acetic acid
[4-(3-{4-[1-(3-methyl-butyl)-1H-indol-3-yl]-piperidin-1-yl}-propoxy)-phenyl]-acetic acid
[4-(3-{4-[1-(2-ethoxy-ethyl)-1H-indol-3-yl]-piperidin-1-yl}-propoxy)-phenyl]-acetic acid
2-{2-[4-(1-prop-2-ynyl-1H-indol-3-yl)-piperidin-1-yl]-ethoxy}-benzoic acid
2-methyl-2-[4-(4-{4-[1-(3-methyl-butyl)-1H-indol-3-yl]-piperidin-1-yl}-butyryl)-phenyl]-propionic acid
1-(2-ethoxy-ethyl)-3-(1-{3-[2-(2H-tetrazol-5-yl)-phenoxy]-propyl}-piperidin-4-yl)-1H-indole
1-(3-methyl-butyl)-3-(1-{3-[2-(2H-tetrazol-5-yl)-phenoxy]-propyl}-piperidin-4-yl)-1H-indole
1-(3-methyl-butyl)-3-(1-{3-[4-(2H-tetrazol-5-yl)-phenoxy]-propyl}-piperidin-4-yl)-1H-indole
2-(2-{4-[1-(2-ethoxy-ethyl)-5-methoxy-1H-indol-3-yl]-piperidin-1-yl}-ethoxy)-6-fluoro-benzoic acid
2-(2-{4-[1-(2-ethoxy-ethyl)-5-fluoro-1H-indol-3-yl]-piperidin-1-yl}-ethoxy)-6-fluoro-benzoic acid
2-(2-{4-[1-(2-ethoxy-ethyl)-6-fluoro-1H-indol-3-yl]-piperidin-1-yl}-ethoxy)-6-fluoro-benzoic acid
2-(2-{4-[5-bromo-1-(2-ethoxy-ethyl)-1H-indol-3-yl]-piperidin-1-yl}-ethoxy)-6-fluoro-benzoic acid
2-(2-{4-[7-bromo-1-(2-ethoxy-ethyl)-1H-indol-3-yl]-piperidin-1-yl}-ethoxy)-6-fluoro-benzoic acid
2-(2-{4-[5-chloro-1-(2-ethoxy-ethyl)-1H-indol-3-yl]-piperidin-1-yl}-ethoxy)-6-fluoro-benzoic acid
2-(2-{4-[1-(2-ethoxy-ethyl)-1H-indol-3-yl]-piperidin-1-yl}-ethoxy)-6-fluoro-benzoic acid
3,5-dibromo-2-(2-{4-[1-(2-ethoxy-ethyl)-5-methoxy-1H-indol-3-yl]-piperidin-1-yl}-ethoxy)-benzoic acid
3,5-dibromo-2-(2-{4-[1-(2-ethoxy-ethyl)-5-fluoro-1H-indol-3-yl]-piperidin-1-yl}-ethoxy)-benzoic acid
3,5-dibromo-2-(2-{4-[1-(2-ethoxy-ethyl)-6-fluoro-1H-indol-3-yl]-piperidin-1-yl}-ethoxy)-benzoic acid
3,5-dibromo-2-(2-{4-[5-bromo-1-(2-ethoxy-ethyl)-1H-indol-3-yl]-piperidin-1-yl}-ethoxy)-benzoic acid
3,5-dibromo-2-(2-{4-[7-bromo-1-(2-ethoxy-ethyl)-1H-indol-3-yl]-piperidin-1-yl}-ethoxy)-benzoic acid
3,5-dibromo-2-(2-(4-[1-(2-ethoxy-ethyl)-1H-indol-3-yl]-piperidin-1-yl}-ethoxy)-benzoic acid
2-(2-{4-[1-(2-ethoxy-ethyl)-6-fluoro-1H-indol-3-yl]-piperidin-1-yl}-ethoxy)-5-methyl-benzoic acid
2-(2-{4-[5-chloro-1-(2-ethoxy-ethyl)-1H-indol-3-yl]-piperidin-1-yl}-ethoxy)-5-methyl-benzoic acid
2-(2-{4-[1-(2-ethoxy-ethyl)-5-methoxy-1H-indol-3-yl]-piperidin-1-yl}-ethoxy)-4-methoxy-benzoic acid
2-(2-{4-[1-(2-ethoxy-ethyl)-6-fluoro-1H-indol-3-yl]-piperidin-1-yl}-ethoxy)-4-methoxy-benzoic acid
2-(2-{4-[5-bromo-1-(2-ethoxy-ethyl)-1H-indol-3-yl]-piperidin-1-yl}-ethoxy)-4-methoxy-benzoic acid
2-(2-{4-[7-bromo-1-(2-ethoxy-ethyl)-1H-indol-3-yl]-piperidin-1-yl}-ethoxy)-4-methoxy-benzoic acid
2-(2-(4-[5-chloro-1-(2-ethoxy-ethyl)-1H-indol-3-yl]-piperidin-1-yl}-ethoxy)-4-methoxy-benzoic acid 2-(2-{4-[1-(2-ethoxy-ethyl)-5-methoxy-1H-indol-3-yl]-piperidin-1-yl}-ethoxy)-benzoic acid
2-(2-{4-[1-(2-ethoxy-ethyl)-5-fluoro-1H-indol-3-yl]-piperidin-1-yl}-ethoxy)-benzoic acid
2-(2-{4-[1-(2-ethoxy-ethyl)-6-fluoro-1H-indol-3-yl]-piperidin-1-yl}-ethoxy)-benzoic acid
2-(2-{4-[5-bromo-1-(2-ethoxy-ethyl)-1H-indol-3-yl]-piperidin-1-yl}-ethoxy)-benzoic acid
2-(2-{4-[5-bromo-1-(2-ethoxy-ethyl)-1H-indol-3-yl]-piperidin-1-yl}-ethoxy)-5-methyl-benzoic acid
2-(2-{4-[5-chloro-1-(2-ethoxy-ethyl)-1H-indol-3-yl]-piperidin-1-yl}-ethoxy)-benzoic acid
2-{2-[4-(1-propyl-1H-indol-3-yl)-piperidin-1-yl]-ethoxy}-benzoic acid
2-(2-{4-[1-(2-iso-propoxy-ethyl)-1H-indol-3-yl]-piperidin-1-yl}-ethoxy)-benzoic acid
2-(2-{4-[1-(3-methoxy-propyl)-1H-indol-3-yl]-piperidin-1-yl}-ethoxy)-benzoic acid
2-(2-(4-[1-(2-ethoxy-ethyl)-4-fluoro-1H-indol-3-yl]-piperidin-1-yl}-ethoxy)-benzoic acid
2-(2-{4-[1-(2-ethoxy-ethyl)-4-fluoro-1H-indol-3-yl]-piperidin-1-yl}-ethoxy)-5-methyl-benzoic acid
2-(2-{4-[1-(2-ethoxy-ethyl)-4-fluoro-1H-indol-3-yl]-piperidin-1-yl}-ethoxy)-4-methoxy-benzoic acid
2-(2-{4-[4-fluoro-1-(2-methoxy-ethyl)-1H-indol-3-yl]-piperidin-1-yl}-ethoxy)-benzoic acid
2-(2-{4-[4-fluoro-1-(2-methoxy-ethyl)-1H-indol-3-yl]-piperidin-1-yl}-ethoxy)-5-methyl-benzoic acid
2-(2-{4-[4-fluoro-1-(2-methoxy-ethyl)-1H-indol-3-yl]-piperidin-1-yl}-ethoxy)-4-methoxy-benzoic acid
5-{4-[1-(2-ethoxy-ethyl)-1H-indol-3-yl]-piperidin-1-yl}-pentanoic acid
6-{4-[1-(2-ethoxy-ethyl)-1H-indol-3-yl]-piperidin-1-yl}-hexanoic acid
7-{4-[1-(2-ethoxy-ethyl)-1H-indol-3-yl]-piperidin-1-yl}-heptanoic acid
3-(3-{4-[1-(2-ethoxy-ethyl)-1H-indol-3-yl]-piperidin-1-yl}-propoxy)-propionic acid
2-(2-{4-[1-(2-ethoxy-ethyl)-7-methyl-1H-indol-3-yl]-piperidin-1-yl}-ethoxy)-5-methyl-benzoic acid
2-(2-{4-[6-bromo-1-(2-ethoxy-ethyl)-1H-indol-3-yl]-piperidin-1-yl}-ethoxy)-benzoic acid
2-(2-{4-[6-bromo-1-(2-ethoxy-ethyl)-1H-indol-3-yl]-piperidin-1-yl}-ethoxy)-5-methyl-benzoic acid
(2-{4-[1-(2-ethoxy-ethyl)-1H-indol-3-yl]-piperidin-1-yl}-ethylsulfanyl)-acetic acid
(4-{4-[1-(2-ethoxy-ethyl)-1H-indol-3-yl]-piperidin-1-yl}-butylsulfanyl)-acetic acid
(3-{3-[4-(1-cyclopropylmethyl-1H-indol-3-yl)-piperidin-1-yl]-propoxy}-phenyl)-acetic acid
(4-{2-[4-(1-cyclopropylmethyl-1H-indol-3-yl)-piperidin-1-yl]-ethoxy}-phenyl)-acetic acid
(3-{2-[4-(1-cyclopropylmethyl-1H-indol-3-yl)-piperidin-1-yl]-ethoxy}-phenyl)-acetic acid
3-[4-(1-pentyl-1H-indol-3-yl)-piperidin-1-ylmethyl]-benzoic acid
5-[4-(6-fluoro-1-pentyl-1H-indol-3-yl)-piperidin-1-ylmethyl]-furan-2-carboxylic acid
3-[4-(6-fluoro-1-pentyl-1H-indol-3-yl)-piperidin-1-ylmethyl]-benzoic acid
2-(4-{4-[4-(1-cyclopropylmethyl-1H-indol-3-yl)-piperidin-1-yl]-butyryl}-phenyl)-2-methyl-propionic acid
3-{3-[4-(1-cyclopropylmethyl-1H-indol-3-yl)-piperidin-1-yl]-propoxy}-benzoic acid
2-{2-[4-(1-cyclohexylmethyl-1H-indol-3-yl)-piperidin-1-yl]ethoxy}-benzoic acid
2-(2-(4-[1-(2-allyloxy-ethyl)-1H-indol-3-yl]-piperidin-1-yl}-ethoxy)-benzoic acid
2-(2-{4-[1-(2-prop-2-ynyloxy-ethyl)-1H-indol-3-yl]-piperidin-1-yl}-ethoxy)-benzoic acid
2-(2-{4-[1-(2-propoxy-ethyl)-1H-indol-3-yl]-piperidin-1-yl}-ethoxy)-benzoic acid
4-(2-{4-[1-(2-ethoxy-ethyl)-1H-indol-3-yl]-piperidin-1-yl}-ethoxy)-benzoic acid
2-(2-{4-[1-(2-ethoxy-ethyl)-1H-indol-3-yl]-piperidin-1-yl}-ethoxy)-benzoic acid
2-(2-{4-[1-(3-methyl-butyl)-1H-indol-3-yl]-piperidin-1-yl}-ethoxy)-benzoic acid
2-(2-{4-[1-(2-methoxy-ethyl)-1H-indol-3-yl]-piperidin-1-yl}-ethoxy)-benzoic acid
2-{2-[4-(1-allyl-1H-indol-3-yl)-piperidin-1-yl]-ethoxy}-benzoic acid
2-(2-{4-[1-(2-ethoxy-ethyl)-5-methoxy-1H-indol-3-yl]-piperidin-1-yl}-ethoxy)-5-methyl-benzoic acid
2-(2-{4-[7-bromo-1-(2-ethoxy-ethyl)-1H-indol-3-yl]-piperidin-1-yl}-ethoxy)-5-methyl-benzoic acid
2-(2-{4-[7-bromo-1-(2-ethoxy-ethyl)-1H-indol-3-yl]-piperidin-1-yl}-ethoxy)-benzoic acid
2-(2-{4-[1-(2-ethoxy-ethyl)-5-fluoro-1H-indol-3-yl]-piperidin-1-yl}-ethoxy)-5-methyl-benzoic acid
2-(2-{4-[1-(2-ethoxy-ethyl)-5-fluoro-1H-indol-3-yl]-piperidin-1-yl}-ethoxy)-4-methoxy-benzoic acid
2-(2-{4-[1-(2-ethoxy-ethyl)-7-methyl-1H-indol-3-yl]-piperidin-1-yl}-ethoxy)-benzoic acid
2-{2-[4-(1-butyl-1H-indol-3-yl)-piperidin-1-yl]-ethoxy}-benzoic acid
2-{2-[4-(1-hexyl-1H-indol-3-yl)-piperidin-1-yl]-ethoxy}-benzoic acid
2-{2-[4-(1-cyclopropylmethyl-6-fluoro-1H-indol-3-yl)-piperidin-1-yl]-ethoxy}-benzoic acid
2-{2-[4-(1H-indol-3-yl)-piperidin-1-yl]-ethoxy}-benzoic acid
3-{4-[1-(2-ethoxyethyl)-1H-indol-3-yl]-piperidin-1-yl}-propionic acid
2-(2-{4-[1-(2-ethoxy-ethyl)-1H-indol-3-yl]-piperidin-1-yl}-ethoxy)-5-methyl-benzoic acid
2-[4-(4-{4-[1-(2-ethoxy-ethyl)-1H-indol-3-yl]-piperidin-1-yl}-butyryl)-phenyl]-2-methyl-propionic acid
1-(2-ethoxy-ethyl)-3-(1-{3-[4-(2H-tetrazol-5-yl)-phenoxy]-propyl}-piperidin-4-yl)-1H-indole
2-{2-[4-(1-cyclopropylmethyl-1H-indol-3-yl)-piperidin-1-yl]-ethoxy}-benzoic acid
3-[4-(1-cyclopropylmethyl-1H-indol-3-yl)-piperidin-1-ylmethyl]-benzoic acid
(4-(3-[4-(1-cyclopropylmethyl-1H-indol-3-yl)-piperidin-1-yl]-propoxy}-phenyl)-acetic acid.

13. A process for preparing a compound as defined in claim 1, which process comprises a) hydrolysing a compound of formula (VI)

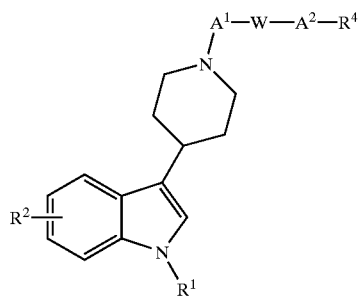

(VI)

wherein $R^1$, $R^2$, $A^1$, $A^2$ and W are as defined in claim 1 and $R^4$ is a —$COOR^5$ group where $R^5$ is $C_{1-4}$ alkyl group, or (b) reacting with an azide a compound of formula (VI) wherein $R^1$, $R^2$, $A^1$, $A^2$ and W are as defined in claim 1 and $R^4$ is a nitrite group.

14. 4-[1-(2-ethoxy-ethyl)-indol-3-yl]-piperidine.

15. A pharmaceutical composition comprising an effective amount of a compound according to claim 1 mixed with a pharmaceutically acceptable diluent or carrier.

16. A method of treating allergic diseases including bronchial asthma, rhinitis, conjunctivitis, dermatosis and urticaria which comprises administering to a human or animal subject in need of such treatment an effective amount of a compound according to claim 1 or a composition according to claim 15.

* * * * *